US012152020B2

(12) United States Patent
Kolleth Krieger et al.

(10) Patent No.: US 12,152,020 B2
(45) Date of Patent: Nov. 26, 2024

(54) PESTICIDALLY ACTIVE AZOLE-AMIDE COMPOUNDS

(71) Applicant: SYNGENTA PARTICIPATIONS AG, Basel (CH)

(72) Inventors: Amandine Kolleth Krieger, Stein (CH); Andrew Edmunds, Stein (CH); Daniel Emery, Stein (CH); Julien Daniel Henri Gagnepain, Stein (CH); Jürgen Harry Schaetzer, Stein (CH); Thomas Pitterna, Stein (CH); Sebastian Rendler, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 780 days.

(21) Appl. No.: 17/290,556

(22) PCT Filed: Oct. 17, 2019

(86) PCT No.: PCT/EP2019/078302
§ 371 (c)(1),
(2) Date: Apr. 30, 2021

(87) PCT Pub. No.: WO2020/094363
PCT Pub. Date: May 14, 2020

(65) Prior Publication Data

US 2021/0403462 A1 Dec. 30, 2021

(30) Foreign Application Priority Data

Nov. 5, 2018 (EP) .................................... 18204422
Feb. 12, 2019 (EP) .................................... 19156711

(51) Int. Cl.
*C07D 413/14* (2006.01)
*A01N 43/653* (2006.01)
*A01N 43/82* (2006.01)
*C07D 403/04* (2006.01)

(52) U.S. Cl.
CPC ......... *C07D 413/14* (2013.01); *A01N 43/653* (2013.01); *A01N 43/82* (2013.01); *C07D 403/04* (2013.01)

(58) Field of Classification Search
CPC .. C07D 413/14; C07D 403/04; A01N 43/653; A01N 43/82
See application file for complete search history.

(56) References Cited

U.S. PATENT DOCUMENTS

2003/0229050 A1 12/2003 Lahm et al.
2020/0404919 A1 12/2020 Schwarz et al.
2023/0028441 A1 1/2023 Jeschke et al.

FOREIGN PATENT DOCUMENTS

JP 2021516238 A 7/2021
JP 2022551309 A 12/2022
WO 2017174158 A1 10/2017
WO 2017192385 A1 11/2017

OTHER PUBLICATIONS

Extended European Search Report for EP18204422.2, mailed on Dec. 19, 2018.
Written Opinion of the International Searching Authority and International Search Report for PCT/EP2019/078302, mailed on Nov. 14, 2019.

*Primary Examiner* — Alma Pipic
(74) *Attorney, Agent, or Firm* — BakerHostetler; Toni-Junell Herbert

(57) ABSTRACT

Compounds of formula I wherein the substituents are as defined in claim 1, and the agrochemically acceptable salts, stereoisomers, enantiomers, tautomers and N-oxides of those compounds, can be used as insecticides.

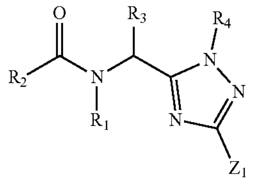

I

14 Claims, No Drawings

1

PESTICIDALLY ACTIVE AZOLE-AMIDE COMPOUNDS

CROSS-REFERENCE TO RELATED APPLICATIONS

This application is a 371 National Stage application of International Application No. PCT/EP2019/078302 filed Oct. 17, 2019, which claims priority to EP 18204422.2, filed Nov. 5, 2018, and EP 19156711.4, filed Feb. 12, 2019, the entire contents of these applications are hereby incorporated by reference.

The present invention relates to pesticidally active, in particular insecticidally active azole-amide compounds, to processes for their preparation, to compositions comprising those compounds, and to their use for controlling animal pests, including arthropods and in particular insects or representatives of the order *Acarina*.

WO2017192385 describes certain heteroaryl-1,2,4-triazole and heteroaryl-tetrazole compounds for use for controlling ectoparasites in animals (such as a mammal and a non-mammal animal). There have now been found novel pesticidally active-azole azine compounds.

The present invention accordingly relates, in a first aspect, to a compound of the formula I

I

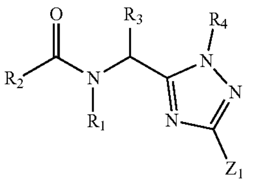

wherein:

- $R_1$ is hydrogen, $C_1$-$C_6$alkyl, $C_1$-$C_6$cyanoalkyl, aminocarbonyl$C_1$-$C_6$alkyl, hydroxycarbonyl$C_1$-$C_6$alkyl, $C_1$-$C_6$nitroalkyl, trimethylsilane$C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl; $C_3$-$C_4$cycloalkyl$C_1$-$C_2$alkyl- wherein the $C_3$-$C_4$cycloalkyl is optionally substituted with 1 or 2 halo atoms; oxetan-3-yl-$CH_2$—; or benzyl optionally substituted with halo or $C_1$-$C_6$haloalkyl;
- $R_2$ is phenyl, pyridine, pyrimidine, pyrazine or pyridazine, wherein the phenyl, pyridine, pyrimidine, pyrazine or pyridazine is optionally substituted with one to three substituents, provided the substituent(s) are not on either carbon adjacent to the carbon C═O is attached, and each substituent is independently selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, halogen, $NO_2$, $SF_5$, CN, $CONH_2$, COOH and $C(S)NH_2$;
- $R_3$ is $C_1$-$C_3$alkyl or $C_1$-$C_3$haloalkyl;
- $R_4$ is pyridine, pyrimidine, pyrazine or pyridazine, wherein the pyridine, pyrimidine, pyrazine or pyridazine is optionally substituted with one substituent selected from $C_1$-$C_3$alkyl, $C_1$-$C_3$haloalkyl, $C_1$-$C_3$alkoxy, $C_3$-$C_4$cycloalkyl, halogen or hydroxy;
- $Z_1$ is halogen, CN, $NH_2C(O)$, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, $C_1$-$C_3$alkoxy-$C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, ($C_1$-$C_3$alkyl)C(O), HC(O), diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxy; or a stereoisomer, enantiomer, tautomer and N-oxide of the compound of formula I, or agrochemically acceptable salt thereof.

2

Compounds of formula I which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

In each case, the compounds of formula I according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The compounds of formula I according to the invention also include hydrates which may be formed during the salt formation.

The term "$C_1$-$C_n$alkyl" as used herein refers to a saturated straight-chain or branched hydrocarbon radical attached via any of the carbon atoms having 1 to n carbon atoms, for example, any one of the radicals methyl, ethyl, n-propyl, 1-methylbutyl, 2-methylbutyl, 3-methylbutyl, 2,2-dimethylpropyl, 1-ethylpropyl, n-hexyl, n-pentyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_1$-$C_n$haloalkyl" as used herein refers to a straight-chain or branched saturated alkyl radical attached via any of the carbon atoms having 1 to n carbon atoms (as mentioned above), where some or all of the hydrogen atoms in these radicals may be replaced by fluorine, chlorine, bromine and/or iodine, i.e., for example, any one of chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. According a term "$C_1$-$C_2$fluoroalkyl" would refer to a $C_1$-$C_2$alkyl radical which carries 1, 2, 3, 4, or 5 fluorine atoms, for example, any one of difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "$C_1$-$C_n$alkoxy" as used herein refers to a straight-chain or branched saturated alkyl radical having 1 to n carbon atoms (as mentioned above) which is attached via an oxygen atom, i.e., for example, any one of the radicals methoxy, ethoxy, n-propoxy, 1-methylethoxy, n-butoxy, 1-methylpropoxy, 2-methylpropoxy or 1,1-dimethylethoxy. The term "halo$C_1$-$C_n$alkoxy" as used herein refers to a $C_1$-$C_n$alkoxy radical where one or more hydrogen atoms on the alkyl radical is replaced by the same or different halo atom(s)—examples include trifluoromethoxy, 2-fluoroethoxy, 3-fluoropropoxy, 3,3,3-trifluoropropoxy, 4-chlorobutoxy.

The term "$C_1$-$C_n$cyanoalkyl" as used herein refers to a straight chain or branched saturated $C_1$-$C_n$alkyl radical having 1 to n carbon atoms (as mentioned above), where one of the hydrogen atoms in these radicals is be replaced by a cyano group: for example, cyanomethyl, 2-cyanoethyl, 2-cyanopropyl, 3-cyanopropyl, 1-(cyanomethyl)-2-ethyl, 1-(methyl)-2-cyanoethyl, 4-cyanobutyl, and the like.

The term "$C_3$-$C_n$cycloalkyl" as used herein refers to 3-n membered cycloalkyl groups such as cyclopropane, cyclobutane, cyclopropane, cyclopentane and cyclohexane.

The term "$C_3$-$C_4$cycloalkyl-$C_1$-$C_2$alkyl-" as used herein refers to 3 or 4 membered cycloalkyl group with either a methylene or ethylene group, which methylene or ethylene group is connected to the rest of the molecule. In the instance, the $C_3$-$C_4$cycloalkyl-$C_1$-$C_2$alkyl- group is substituted, the substituent(s) is on the cycloalkyl group.

The term "aminocarbonyl$C_1$-$C_n$alkyl" as used herein refers to an alkyl radical where one of the hydrogen atoms in the radical is replaced by CONH2 group.

The term "hydroxycarbonyl$C_1$-$C_n$alkyl" as used herein refers to an alkyl radical where one of the hydrogen atoms in the radical is replaced by COOH group.

The term "$C_1$-$C_n$nitroalkyl" as used herein refers to an alkyl radical where one of the hydrogen atoms in the radical is replaced by $NO_2$ group.

The term "$C_1$-$C_n$haloalkylthio" as used herein refers to a $C_1$-$C_3$haloalkyl moiety linked through a sulfur atom.

The term "trimethylsilane$C_1$-$C_n$alkyl" as used herein refers to an alkyl radical where one of the hydrogen atoms in the radical is replaced by a —$Si(CH_3)_3$ group.

The term "$C_2$-$C_n$alkenyl" as used herein refers to a straight or branched alkenyl chain having form two to n carbon atoms and one or two double bonds, for example, ethenyl, prop-I-enyl, but-2-enyl.

The term "$C_2$-$C_n$haloalkenyl" as used herein refers to a $C_2$-$C_n$alkenyl moiety substituted with one or more halo atoms which may be the same or different.

The term "$C_2$-$C_n$alkynyl" as used herein refers to a straight or branched alkynyl chain having from two to n carbon atoms and one triple bond, for example, ethynyl, prop-2-ynyl, but-3-ynyl, The term "$C_2$-$C_n$haloalkynyl" as used herein refers to a $C_2$-$C_n$alkynyl moiety substituted with one or more halo atoms which may be the same or different.

Halogen is generally fluorine, chlorine, bromine or iodine. This also applies, correspondingly, to halogen in combination with other meanings, such as haloalkyl The term "($C_1$-$C_n$alkyl)sulfonylamino" as used herein refers to a $C_1$-$C_n$alkyl group connected to a sulfur atom of a $S(O)_2$ moiety, which sulfur is also connected to a nitrogen atom of an amino (i.e. NH) moiety, wherein the nitrogen atom of the amino moiety is bonded to the rest of the molecule, such as $CH_3S(O)_2NH$—.

The term "($C_1$-$C_n$alkyl)sulfonyl($C_1$-$C_n$alkyl)amino" as used herein refers to a ($C_1$-$C_n$alkyl)sulfonylamino group wherein the hydrogen atom of the amino group is substituted with a $C_1$-$C_n$alkyl group, such as $CH_3S(O)_2N(CH_3)$—.

The term "($C_1$-$C_3$alkyl)C(O)($C_1$-$C_3$alkyl)N" as used herein refers to a $C_1$-$C_n$alkyl group connected to a carbon atom of a C(═O) moiety, which carbon is also connected to a nitrogen atom, which nitrogen atom is connected also to $C_1$-$C_3$alkyl group, and which nitrogen atom is bonded to the rest of the molecule, such as $CH_3C(O)N(CH_3)$—.

Examples of a 5 membered heteroaromatic ring include pyrazolyl, furyl, thienyl, imidazolyl, isoxazolyl, oxazolyl, thiazolyl, isothiazolyl, triazolyl, oxadiazolyl, thiadiazolyl, tetrazolyl; preferred is pyrazolyl.

The pyridine, pyrimidine, pyrazine and pyridazine groups (unsubstituted or substituted) for $R_2$ and $R_4$ are each connected via a carbon atom on the respective ring to the rest of the compound.

As used herein, the term "controlling" refers to reducing the number of pests, eliminating pests and/or preventing further pest damage such that damage to a plant or to a plant derived product is reduced.

The staggered line as used herein, for example, in $Y_1$; and $R_4$-1, represent the point of connection/attachment to the rest of the compound.

As used herein, the term "pest" refers to insects, and molluscs that are found in agriculture, horticulture, forestry, the storage of products of vegetable origin (such as fruit, grain and timber); and those pests associated with the damage of man-made structures. The term pest encompasses all stages in the life cycle of the pest.

As used herein, the term "effective amount" refers to the amount of the compound, or a salt thereof, which, upon single or multiple applications provides the desired effect.

An effective amount is readily determined by the skilled person in the art, by the use of known techniques and by observing results obtained under analogous circumstances. In determining the effective amount a number of factors are considered including, but not limited to: the type of plant or derived product to be applied; the pest to be controlled & its lifecycle; the particular compound applied; the type of application; and other relevant circumstances.

As one of ordinary skill in the art will appreciate, compounds of formula I contain a stereogenic centre which is indicated with an asterisk in the structure below:

I*

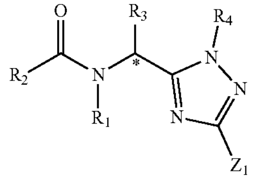

where $R_1$, $R_2$, $R_3$, $R_4$, and Z, are as defined in the first aspect.

The present invention contemplates both racemates and individual enantiomers. Compounds having preferred stereochemistry are set out below.

Particularly preferred compounds of the present invention are compounds of formula I'a:

I'a

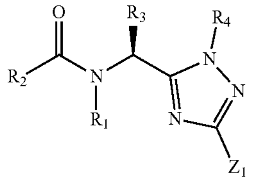

where $R_1$, $R_2$, $R_3$, $R_4$, and $Z_1$ are as defined in the first aspect, and stereoisomers, enantiomers, tautomers and N-oxides of the compounds of formula (I'a), and agrochemically acceptable salts thereof.

The term "optionally substituted" as used herein means that the group referenced is is either unsubstituted or is substituted by a designated substitutent, for example, "$C_3$-$C_4$cycloalkyl is optionally substituted with 1 or 2 halo atoms" means $C_3$-$C_4$cycloalkyl, $C_3$-$C_4$cycloalkyl substituted with 1 halo atom and $C_3$-$C_4$cycloalkyl substituted with 2 halo atoms.

Embodiments according to the invention are provided as set out below.

In an embodiment of each aspect of the invention, $R_1$ is

A. hydrogen; $C_1$-$C_6$alkyl optionally substituted with one substituent selected from: CN, $CONH_2$, COOH, $NO_2$, and —$Si(CH_3)_3$; $C_1$-$C_6$haloalkyl; $C_2$-$C_6$alkenyl; $C_2$-$C_6$alkynyl; $C_2$-$C_6$haloalkynyl; $C_3$-$C_4$cycloalkyl-$C_1$-$C_2$alkyl—wherein the $C_3$-$C_4$cycloalkyl- is optionally substituted with 1 or 2 halo atoms; oxetan-3-yl-$CH_2$—; or benzyl optionally substituted with halo or $C_1$-$C_3$haloalkyl; or B. hydrogen; $C_1$-$C_6$haloalkyl; $C_1$-$C_6$alkyl optionally substituted with CN or $Si(CH_3)_3$; $C_3$-$C_6$alkynyl; $C_3$-$C_4$cycloalkyl-$C_1$-$C_2$alkyl wherein the $C_3$-$C_4$cycloalkyl is optionally substituted with 1 or 2 halo atoms; oxetan-3-yl-$CH_2$—; or benzyl optionally substituted with halo; or C. hydrogen, $C_1$-$C_6$alkyl, $C_3$-$C_4$cycloalkyl$C_1$-$C_2$alkyl- wherein the $C_3$-$C_4$cycloalkyl is optionally substituted with 1 or 2 halo atoms, or oxetan-3-yl-$CH_2$—; or D. hydrogen, $C_1$-$C_6$alkyl, or $C_3$-$C_4$cycloalkyl$C_1$-$C_2$alkyl-; or E. hydrogen; $C_1$-$C_6$haloalkyl; $C_1$-$C_6$alkyl optionally substituted with CN or $Si(CH_3)_3$; $C_3$-$C_6$alkynyl; or $C_3$-$C_4$cycloalkyl-$C_1$-$C_2$alkyl wherein the $C_3$-$C_4$cycloalkyl is optionally substituted with 1 or 2 halo atoms; or F. hydrogen; $C_1$-$C_6$haloalkyl; $C_1$-$C_6$alkyl; $C_3$-$C_6$alkynyl; or $C_3$-$C_4$cycloalkyl-$C_1$-$C_2$alkyl wherein the $C_3$-$C_4$cycloalkyl is optionally substituted with 1 or 2 halo atoms; or G. cyclopropyl-$CH_2$—, n-propyl, CH≡$CCH_2$—, $CF_3CH_2CH_2$—, $FCH_2CH_2$—, $FCH_2CH_2CH_2$—, 2,2-difluorocyclopropyl-$CH_2$—, 2,2-dichlorocyclopropyl-$CH_2$—, hydrogen, $CH_3$, $(CH_3)_3SiCH_2$—, $CH_3CH_2$—, or $CNCH_2$—; or H. cyclopropyl-$CH_2$—, n-propyl, CH≡$CCH_2$—, $CF_3CH_2CH_2$—, $FCH_2CH_2$—, $FCH_2CH_2CH_2$—, 2,2-difluorocyclopropyl-$CH_2$— or 2,2-dichlorocyclopropyl-$CH_2$—; or I. cyclopropyl-$CH_2$—, n-propyl, CH≡$CCH_2$—, $CF_3CH_2CH_2$—, $FCH_2CH_2$—, $FCH_2CH_2CH_2$—, 2,2-difluorocyclopropyl-$CH_2$—, hydrogen, $CH_3$, $(CH_3)_3SiCH_2$—, or $CH_3CH_2$—; or J. cyclopropyl-$CH_2$—, n-propyl, CH≡$CCH_2$—, $CF_3CH_2CH_2$—, $FCH_2CH_2$—, $FCH_2CH_2CH_2$—, or 2,2-difluorocyclopropyl-$CH_2$—; or K. cyclopropyl-$CH_2$—, n-propyl, CH≡$CCH_2$—, $CF_3CH_2CH_2$—, $FCH_2CH_2$—, or $FCH_2CH_2CH_2$—; or L. cyclopropyl-$CH_2$—, CH≡$CCH_2$—, hydrogen or $CH_3$; or M. CH≡$CCH_2$— or cyclopropyl-$CH_2$—; or N. cyclopropyl-$CH_2$—; or O. cyclopropyl-$CH_2$—, hydrogen or $CH_3$; or P. hydrogen.

In an embodiment of each aspect of the invention, $R_2$ is

A. phenyl, pyridine, pyrimidine, pyrazine or pyridazine, wherein the phenyl, pyridine, pyrimidine, pyrazine or pyridazine is optionally substituted with one to three substituents, provided the substituent(s) are not on either carbon adjacent to the carbon bonded to the —C(O)— group, each independently selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, halo, $NO_2$, $SF_5$, CN, $CONH_2$, COOH and $C(S)NH_2$; or B. phenyl, pyridine, pyrimidine, pyrazine or pyridazine, wherein the phenyl, pyridine, pyrimidine, pyrazine or pyridazine is optionally substituted with one to two substituents, provided the substituent(s) are not on either carbon adjacent to the carbon C═O is attached too, and each substituent is independently selected from: $C_1$-$C_3$alkyl, $C_1$-$C_3$haloalkyl, $C_1$-$C_3$alkoxy, $C_1$-$C_3$haloalkoxy, halogen or CN; or C. phenyl, 3-pyridine or 4-pyridine substituted with one or two substituents independently selected from: $C_1$-$C_3$haloalkyl, $C_1$-$C_3$haloalkoxy, halo, CN, or $C(S)NH_2$, provided the substituent(s) are not on either carbon adjacent to the carbon bonded to the —C(O)— group; or D. phenyl, 3-pyridine or 4-pyridine substituted with one or two substituents independently selected from: $C_1$-$C_3$haloalkyl, $C_1$-$C_3$haloalkoxy, halo, or CN, provided the substituent(s) are not on either carbon adjacent to the carbon bonded to the —C(O)— group; or E. phenyl, or 3-pyridine substituted with one or two substituents independently selected from: $C_1$-$C_3$haloalkyl, $C_1$-$C_3$haloalkoxy, halo, or CN, provided the substituent(s) are not on either carbon adjacent to the carbon bonded to the —C(O)— group; or F. 3,5-bis(trifluoromethyl)phenyl, 3,5-dichlorophenyl, 3-trifluoromethoxyphenyl, 3-chloro-5-trifluoromethylphenyl, 3-cyanophenyl, 3-chloro-5-trifluoromethoxyphenyl, 5-trifluoromethylpyridin-3-yl, 3-bromo-5-trifluoromethylphenyl, 3-cyano-5-trifluoromethylphenyl or 2,6-bis(trifluoromethyl)pyridin-4-yl; or G. 3,5-bis(trifluoromethyl)phenyl, 3,5-dichlorophenyl, 3-trifluoromethoxyphenyl, 3-chloro-5-trifluoromethylphenyl, 3-cyanophenyl, 3-chloro-5-trifluoromethoxyphenyl, 5-trifluoromethylpyridi-3-yl, 3-bromo-5-trifluoromethylphenyi or 3-cyano-5-trifluoromethyl-phenyl; or H. 3,5-bis(trifluoromethyl)phenyl, 3,5-dichlorophenyl, 3-trifluoromethoxyphenyl, 3-chloro-5-trifluoromethylphenyl, 3-cyanophenyl, 3-chloro-5-trifluoromethoxyphenyl, or 5-trifluoromethylpyridin-3-yl; or I. is 3,5-bis(trifluoromethyl)phenyl, 3-chloro-5-trifluoromethylphenyl, 3-cyanophenyL 3-chloro-5-trifluoromethoxyphenyl, 5-trifluoromethylpyridin-3-yl or 3-cyano-5-trifluoromethylphenyl; or J. 3,5-bis(trifluoromethyl)phenyl, 3-chloro-5-trifluoromethylphenyl, 3-chloro-5-trifluoromethoxyphenyl or 5-trifluoromethpyridin-3-yl; or K. 3,5-bis(trifluoromethyl)phenyl; or L. one of $Y_1$ to $Y_{21}$; or $Y_1$

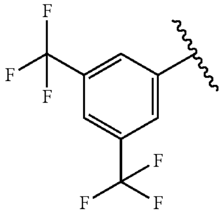

$Y_2$

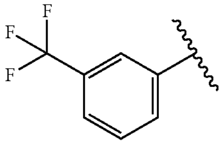

$Y_3$

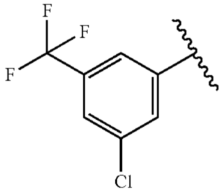

$Y_4$

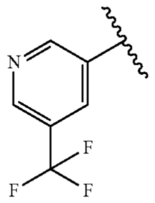

$Y_5$

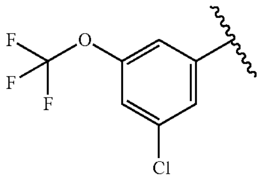

-continued $Y_6$

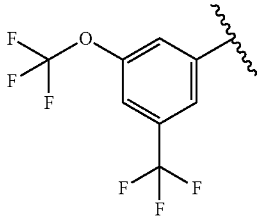

$Y_7$

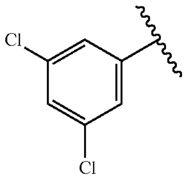

$Y_8$

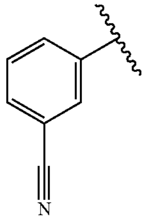

$Y_9$

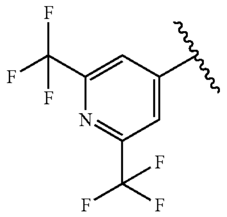

$Y_{10}$

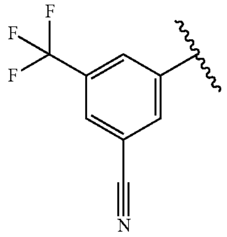

$Y_{11}$

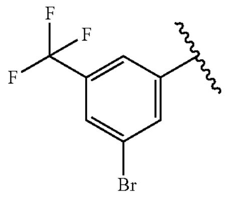

$Y_{12}$

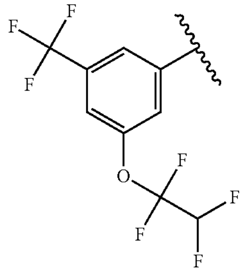

-continued

Y13

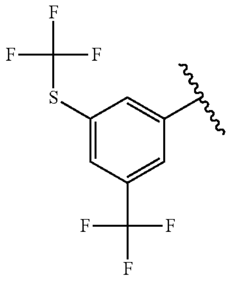

Y14

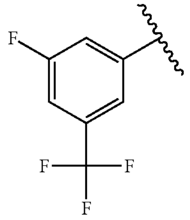

Y15

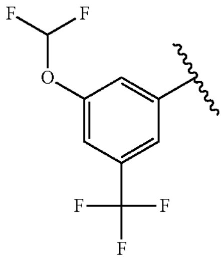

Y16

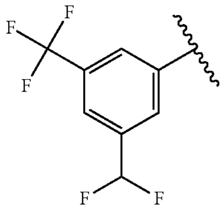

Y17

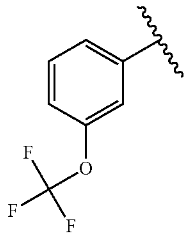

Y18

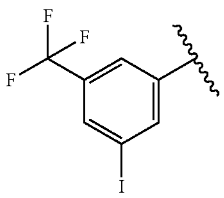

-continued

Y19

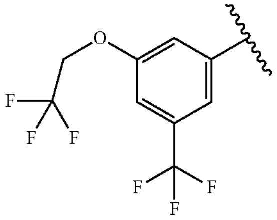

Y20

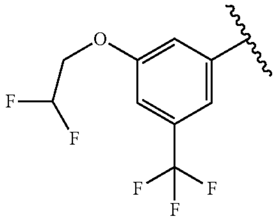

Y21

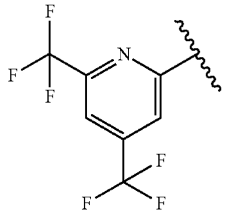

M. one of $Y_1$, $Y_2$, $Y_3$, $Y_5$, $Y_6$, $Y_7$, $Y_{11}$, $Y_{13}$ or $Y_{15}$; or
N. one of $Y_1$, $Y_3$, $Y_5$, $Y_6$, $Y_{11}$, $Y_{13}$ or $Y_{15}$; or
O. one of $Y_1$, $Y_3$, or $Y_{11}$; or
P. one of $Y_1$, $Y_5$, $Y_6$, $Y_{11}$, $Y_{13}$, $Y_{15}$, $Y_{19}$, or $Y_{20}$;
Q. one of $Y_1$, $Y_6$, $Y_{11}$, $Y_{15}$, $Y_{19}$, or $Y_{20}$;
R. one of $Y_1$, $Y_{15}$, or $Y_{20}$
S. $Y_1$.

In an embodiment of each aspect of the invention, $R_3$ is
A. $C_1$-$C_3$alkyl or $C_1$-$C_3$haloalkyl; or
B. $C_1$-$C_3$alkyl; or
C. methyl.

In an embodiment of each aspect of the invention, $R_4$ is
A. pyridine or pyrimidine, wherein the pyridine, pyrimidine, is optionally substituted with one $C_1$-$C_3$alkoxy or halogen; or
B. 2-pyridine, 2-pyrimidine, 2-pyrazine or 2-pyridazine, each optionally substituted with $C_1$-$C_3$alkoxy or halo; or
C. pyridine or pyrimidine, wherein the pyridine, pyrimidine, is optionally substituted with one halogen;
D. 2-pyridine or 2-pyrimidine, each optionally substituted with $C_1$-$C_3$alkoxy or halo; or
E. selected from $J_1$ to $J_8$; or $J_1$

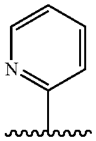

-continued $J_2$

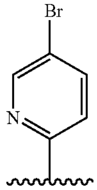

$J_3$

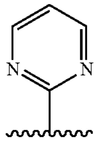

$J_4$

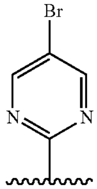

$J_5$

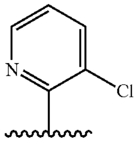

$J_6$

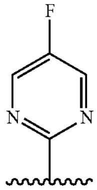

$J_7$

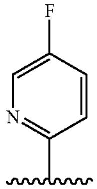

$J_8$

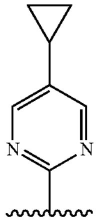

F. selected from $J_1$, $J_2$, $J_3$, $J_4$, $J_6$, and $J_7$ and $J_8$ or
G. selected from $J_2$, $J_3$, $J_4$ and $J_7$; or
H. $J_3$ or $J_7$; or
I. $J_2$ or $J_4$; or
J. 2-pyridine (i.e $J_1$), or 2-pyrimidine (i.e $J_3$); or
K. 2-pyrimidine.

In an embodiment of each aspect of the invention, Z, is

A. halogen, CN, $NH_2C(O)$, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, $C_1$-$C_3$alkoxy-$C_1$-$C_3$alkoxy, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, ($C_1$-$C_3$alkyl)C(O), HC(O), diphenylmethanimine, $C_1$-$C_3$haloalkoxy, phenyl or a 5-membered heteroaromatic ring selected from pyrazolyl, furyl, thienyl, imidazolyl, isoxazolyl, oxazolyl, thiazolyl, isothiazolyl, triazolyl, oxadiazolyl, thiadiazolyl, and tetrazolyl, wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxy B. halogen, CN, $NH_2C(O)$, amino, ($C_1$-$C_3$alkyl)amino, di($C_1$-$C_3$alkyl)amino, hydroxyl, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, $C_1$-$C_3$alkoxy-$C_1$-$C_3$alkoxy, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, $C_1$-$C_3$haloalkoxy, ($C_1$-$C_3$alkyl)C(O), HC(O), or diphenylmethanimine; or C. halogen, CN, amino, di($C_1$-$C_3$alkyl)amino, hydroxyl, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, $C_1$-$C_3$haloalkoxy, or diphenylmethanimine; or D. halogen, CN, amino, di($C_1$-$C_3$alkyl)amino, hydroxyl, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH. $C_1$-$C_3$haloalkoxy, or diphenylmethanimine; or E. halogen, CN, amino, di($C_1$-$C_3$alkyl)amino, hydroxyl, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, $C_1$-$C_3$haloalkoxy, or diphenylmethanimine; or F. halogen, CN, amino, di($C_1$-$C_3$alkyl)amino, hydroxyl, $C_3$-$C_4$halocycloalkyl, $C_3$-$C_4$cyanocycloalkyl, $C_1$-$C_4$haloalkylsulfanyl, $C_1$-$C_4$haloalkylsulfinyl, $C_1$-$C_4$haloalkylsulfonyl, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, $C_1$-$C_3$haloalkoxy, or diphenylmethanimine; or G. halogen, CN, amino, di($C_1$-$C_3$alkyl)amino, hydroxyl, $C_3$-$C_4$halocycloalkyl, $C_3$-$C_4$cyanocycloalkyl, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, $C_1$-$C_3$haloalkoxy, or diphenylmethanimine; or H. halogen, CN, amino, di($C_1$-$C_3$alkyl)amino, hydroxyl, $C_3$-$C_4$halocycloalkyl, $C_1$-$C_3$haloalkoxy, or $C_3$-$C_4$cyanocycloalkyl; or I. halogen, CN, amino, $C_3$-$C_4$halocycloalkyl, $C_1$-$C_3$haloalkoxy, or $C_3$-$C_4$cyanocycloalkyl; or J. halogen, amino, $C_3$-$C_4$halocycloalkyl, $C_1$-$C_3$haloalkoxy, or $C_3$-$C_4$cyanocycloalkyl; or K. halogen, amino or $C_1$-$C_3$haloalkoxy; or L. trifluoromethoxy, 2,2-difluoroethoxy, difluoromethoxy, chloro, fluoro, amino, 2,2,2-trifluoroethoxy, bromo, or iodo; or M. trifluoromethoxy, 2,2-difluoroethoxy, difluoromethoxy, chloro, 2,2,2-trifluoroethoxy, bromo, iodo or amino; or N. bromo, chloro, iodo, difluoromethoxy, trifluoromethoxy, or amino; or O. bromo, chloro, iodo, difluoromethoxy, or trifluoromethoxy; or P. bromo, chloro, or iodo.

The present invention, accordingly, makes available a compound of formula I having the substituents $R_1$, $R_2$, $R_3$, $R_4$, and $Z_1$ as defined above in all combinations/each permutation. Accordingly, made available, for example, is a compound of formula I with $R_1$ being embodiment D (i.e. hydrogen, $C_1$-$C_6$alkyl, or $C_3$-$C_4$cycloalkyl$C_1$-$C_2$alkyl-); $R_2$ being an embodiment H (i.e. 3,5-bis(trifluoromethyl)phenyl, 3,5-dichlorophenyl, 3-trifluoromethoxyphenyl, 3-chloro-5-trifluoromethylphenyl, 3-cyanophenyl, 3-chloro-5-trifluoromethoxyphenyl, or 5-trifluoromethylpyridin-3-yl); $R_3$ being embodiment C (i.e. methyl); $R_4$ being embodiment A (i.e. pyridine or pyrimidine, wherein the pyridine, pyrimidine, is optionally substituted with one $C_1$-$C_3$alkoxy or halogen); and $Z_1$ being embodiment E (i.e. halogen, CN, amino, di($C_1$-$C_3$alkyl)amino, hydroxyl, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, $C_1$-$C_3$haloalkoxy, or diphenylmethanimine).

In an embodiment of each aspect of the invention, the compound of formula I has as $R_1$ hydrogen, $C_1$-$C_6$alkyl, $C_2$-$C_6$alkenyl, $C_2$-$C_6$alkynyl, $C_3$-$C_4$cycloalkyl$C_1$-$C_2$alkyl- wherein the $C_3$-$C_4$cycloalkyl is optionally substituted with 1 or 2 halo atoms, or oxetan-3-yl-$CH_2$—; as $R_2$ phenyl, pyridine, pyrimidine, pyrazine or pyridazine, wherein the phenyl, pyridine, pyrimidine, pyrazine or pyridazine is optionally substituted with one to two substituents, provided the substituent(s) are not on either carbon adjacent to the carbon C═O is attached too, and each substituent is independently selected from: $C_1$-$C_3$alkyl, $C_1$-$C_3$haloalkyl, $C_1$-$C_3$alkoxy, $C_1$-$C_3$haloalkoxy, halogen or CN; as $R_3$$C_1$-$C_3$alkyl; as $R_4$ pyridine or pyrimidine, wherein the pyridine, pyrimidine, is optionally substituted with one $C_1$-$C_3$alkoxy or halogen; and as $Z_1$ halogen, CN, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxyl.

In an embodiment of each aspect of the invention, the compound of formula I has as $R_1$ hydrogen, methyl, allyl, proparyl, or cyclopropmethyl-; as $R_2$ phenyl, pyridine, pyrimidine, pyrazine or pyridazine, wherein the phenyl, pyridine, pyrimidine, pyrazine or pyridazine is optionally substituted with one to two substituents, provided the substituent(s) are not on either carbon adjacent to the carbon C═O is attached too, and each substituent is independently selected from: $C_1$-$C_3$alkyl, $C_1$-$C_3$haloalkyl, $C_1$-$C_3$alkoxy, $C_1$-$C_3$haloalkoxy, halogen or CN; as $R_3$$C_1$-$C_3$alkyl; as $R_4$ pyridine or pyrimidine, wherein the pyridine, pyrimidine, is optionally substituted with one $C_1$-$C_3$alkoxy or halogen; and as $Z_1$ halogen, CN, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxyl.

In an embodiment of each aspect of the invention, the compound of formula I has as $R_1$ hydrogen, methyl, or cyclopropmethyl-; as $R_2$ one of $Y_1$ to $Y_{21}$; as $R_3$$C_1$-$C_3$alkyl; as $R_4$ pyridine or pyrimidine, wherein the pyridine, pyrimidine, is optionally substituted with one $C_1$-$C_3$alkoxy or halogen; and as $Z_1$ halogen, CN, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxyl.

In an embodiment of each aspect of the invention, the compound of formula I has as $R_1$ hydrogen, methyl, or cyclopropmethyl-; as $R_2$ one of selected from $Y_1$, $Y_5$, $Y_6$, $Y_{11}$, $Y_{13}$, $Y_{15}$, $Y_{19}$, and $Y_{20}$; as $R_3$$C_1$-$C_3$alkyl; as $R_4$ pyridine or pyrimidine, wherein the pyridine, pyrimidine, is optionally substituted with one $C_1$-$C_3$alkoxy or halogen; and as $Z_1$ halogen, CN, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxyl.

In an embodiment of each aspect of the invention, the compound of formula I has as $R_1$ hydrogen, methyl, or cyclopropmethyl-; as $R_2$ one of $Y_1$, $Y_5$, $Y_6$, $Y_{11}$, $Y_{13}$, $Y_{15}$, $Y_{19}$, or $Y_{20}$; as $R_3$$C_1$-$C_3$alkyl; as $R_4$ pyridine or pyrimidine, wherein the pyridine, pyrimidine, is optionally substituted with one $C_1$-$C_3$alkoxy or halogen; and as $Z_1$ halogen, CN, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxyl.

In an embodiment of each aspect of the invention, the compound of formula I has as $R_1$ hydrogen, methyl, or cyclopropmethyl-; as $R_2$ one of $Y_1$, $Y_6$, $Y_{11}$, $Y_{15}$, $Y_{19}$, or $Y_{20}$; as $R_3$$C_1$-$C_3$alkyl; as $R_4$ pyridine or pyrimidine, wherein the pyridine, pyrimidine, is optionally substituted with one $C_1$-$C_3$alkoxy or halogen; and as $Z_1$ halogen, CN, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl ($C_1$-$C_3$alkyl)amino, ($C_1$-$C_3$alkyl)NHC(O), ($C_1$-$C_3$alkyl)$_2$ NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxyl.

In an embodiment of each aspect of the invention, the compound of formula I has as $R_1$ hydrogen, methyl, or cyclopropmethyl-; as $R_2$$Y_1$; as $R_3$$C_1$-$C_3$alkyl; as $R_4$ pyridine or pyrimidine, wherein the pyridine, pyrimidine, is optionally substituted with one $C_1$-$C_3$alkoxy or halogen; and as $Z_1$ halogen, CN, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxyl.

In an embodiment of each aspect of the invention, the compound of formula I has as $R_1$ hydrogen, methyl, or cyclopropmethyl-; as $R_2$ one of $Y_1$, $Y_6$, $Y_{11}$, $Y_{15}$, $Y_{19}$, or $Y_{20}$; as $R_3$ methyl; as $R_4$ pyridine or pyrimidine, wherein the pyridine, pyrimidine, is optionally substituted with one $C_1$-$C_3$alkoxy or halogen; and as Z, halogen, CN, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl ($C_1$-$C_3$alkyl)amino, ($C_1$-$C_3$alkyl)NHC(O), ($C_1$-$C_3$alkyl)$_2$ NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxyl.

In an embodiment of each aspect of the invention, the compound of formula I has as $R_1$ hydrogen, methyl, or cyclopropmethyl-; as $R_2$ one of $Y_1$, $Y_6$, $Y_{11}$, $Y_{15}$, $Y_{19}$, or $Y_{20}$; as $R_3$ methyl; as $R_4$ 2-pyridine or 2-pyrimidine, each optionally substituted with $C_1$-$C_3$alkoxy or halo; and as $Z_1$ halogen, CN, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxyl.

In an embodiment of each aspect of the invention, the compound of formula I has as $R_1$ hydrogen, methyl, or cyclopropmethyl-; as $R_2$ one of $Y_1$, $Y_6$, $Y_{11}$, $Y_{15}$, $Y_{19}$, or $Y_{20}$; as $R_3$ methyl; as $R_4$ selected from $J_1$ to $J_8$; and as $Z_1$ halogen, CN, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxyl.

In an embodiment of each aspect of the invention, the compound of formula I has as $R_1$ hydrogen, methyl, or cyclopropmethyl-; as $R_2$ one of $Y_1$, $Y_6$, $Y_{11}$, $Y_{15}$, $Y_{19}$, or $Y_{20}$; as $R_3$ methyl; as $R_4$ selected from $J_1$ to $J_8$; and as $Z_1$ halogen, CN, amino (i.e $NH_2$), ($C_1$-$C_3$alkyl)amino, di($C_1$-$C_3$alkyl)amino, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxyl.

In an embodiment of each aspect of the invention, the compound of formula I has as $R_1$ hydrogen, methyl, or cyclopropmethyl-; as $R_2$ one of $Y_1$, $Y_6$, $Y_{11}$, $Y_{15}$, $Y_{19}$, or $Y_{20}$; as $R_3$ methyl; as $R_4$ selected from $J_1$ or $J_3$; and as $Z_1$ halogen, CN, amino (i.e $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, diphenylmethanimine, $C_1$-$C_3$haloalkoxy, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxyl.

In an embodiment of each aspect of the invention, the compound of formula I has as $R_1$ hydrogen, methyl, or cyclopropmethyl-; as $R_2$ one of $Y_1$ to $Y_{21}$; as $R_3$ methyl; as $R_4$ selected from $J_1$ to $J_8$; and as $Z_1$ halogen, amino, or $C_1$-$C_3$haloalkoxy.

In an embodiment of each aspect of the invention, the compound of formula I has as $R_1$ hydrogen, methyl, or cyclopropmethyl-; as $R_2$ one of $Y_1$, $Y_6$, $Y_{11}$, $Y_{15}$, $Y_{19}$, or $Y_{20}$; as $R_3$ methyl; as $R_4$ selected from $J_1$ to $J_8$; and as $Z_1$ halogen, amino, or $C_1$-$C_3$haloalkoxy.

In an embodiment of each aspect of the invention, the compound of formula I has as $R_1$ hydrogen, methyl, or cyclopropmethyl-; as $R_2$ one of $Y_1$, $Y_6$, $Y_{11}$, $Y_{15}$, $Y_{19}$, or $Y_{20}$; as $R_3$ methyl; as $R_4$ selected from $J_1$ to $J_8$; and as $Z_1$ trifluoromethoxy, 2,2-difluoroethoxy, difluoromethoxy, chloro, 2,2,2-trifluoroethoxy, bromo, iodo or amino.

In an embodiment of each aspect of the invention, the compound of formula I has as $R_1$ hydrogen, methyl, or cyclopropmethyl-; as $R_2$ one of $Y_1$, to $Y_{21}$; as $R_3$ methyl; as $R_4$ selected from $J_1$ to $J_8$; and as $Z_1$ trifluoromethoxy, 2,2-difluoroethoxy, difluoromethoxy, chloro, 2,2,2-trifluoroethoxy, bromo, iodo or amino.

In an embodiment of each aspect of the invention, the compound of formula I has as $R_1$ hydrogen, methyl, or cyclopropmethyl-; as $R_2$ one of $Y_1$, to $Y_{21}$; as $R_3$ methyl; as $R_4$ selected from $J_1$ to $J_8$; and as $Z_1$ trifluoromethoxy, difluoromethoxy, chloro, bromo, iodo or amino.

In an embodiment of each aspect of the invention, the compound of formula I has as $R_1$ hydrogen, methyl, or cyclopropmethyl-; as $R_2$ one of $Y_1$ to $Y_{21}$; as $R_3$ methyl; as $R_4$ selected from $J_2$, $J_3$, $J_4$ and $J_7$; and as $Z_1$ halogen, amino, or $C_1$-$C_3$haloalkoxy.

In an embodiment of each aspect of the invention, the compound of formula I has as $R_1$ hydrogen, methyl, or cyclopropmethyl-; as $R_2$ one of $Y_1$, $Y_6$, $Y_{11}$, $Y_{15}$, $Y_{19}$, or $Y_{20}$; as $R_3$ methyl; as $R_4$ selected from $J_2$, $J_3$, $J_4$ and $J_7$; and as $Z_1$ halogen, amino, or $C_1$-$C_3$haloalkoxy.

In an embodiment of each aspect of the invention, the compound of formula I has as $R_1$ hydrogen, methyl, or cyclopropmethyl-; as $R_2$ one of $Y_1$, $Y_6$, $Y_{11}$, $Y_{15}$, $Y_{19}$, or $Y_{20}$; as $R_3$ methyl; as $R_4$ selected from $J_2$, $J_3$, $J_4$ and $J_7$; and as $Z_1$ trifluoromethoxy, 2,2-difluoroethoxy, difluoromethoxy, chloro, 2,2,2-trifluoroethoxy, bromo, iodo or amino.

In an embodiment of each aspect of the invention, the compound of formula I has as $R_1$ hydrogen, methyl, or cyclopropmethyl-; as $R_2$ one of $Y_1$, to $Y_{21}$; as $R_3$ methyl; as $R_4$ selected from $J_2$, $J_3$, $J_4$ and $J_7$; and as $Z_1$ trifluoromethoxy, 2,2-difluoroethoxy, difluoromethoxy, chloro, 2,2,2-trifluoroethoxy, bromo, iodo or amino.

In an embodiment of each aspect of the invention, the compound of formula I has as $R_1$ hydrogen, methyl, or cyclopropmethyl-; as $R_2$ one of $Y_1$, to $Y_{21}$; as $R_3$ methyl; as $R_4$ selected from $J_2$, $J_3$, $J_4$ and $J_7$; and as $Z_1$ trifluoromethoxy, difluoromethoxy, chloro, bromo, iodo or amino.

In an embodiment of each aspect of the invention, the compound of formula I has as $R_1$ hydrogen, methyl, or cyclopropmethyl-; as $R_2$ one of $Y_1$ to $Y_{21}$; as $R_3$ methyl; as $R_4$ $J_1$ or $J_3$; and as $Z_1$ halogen, amino, or $C_1$-$C_3$haloalkoxy.

In an embodiment of each aspect of the invention, the compound of formula I has as $R_1$ hydrogen, methyl, or cyclopropmethyl-; as $R_2$ one of $Y_1$, $Y_6$, $Y_{11}$, $Y_{15}$, $Y_{19}$, or $Y_{20}$; as $R_3$ methyl; as $R_4$ $J_1$ or $J_3$; and as Z, halogen, amino, or $C_1$-$C_3$haloalkoxy.

In an embodiment of each aspect of the invention, the compound of formula I has as $R_1$ hydrogen, methyl, or cyclopropmethyl-; as $R_2$ one of $Y_1$, $Y_6$, $Y_{11}$, $Y_{15}$, $Y_{19}$, or $Y_{20}$; as $R_3$ methyl; as $R_4$ $J_1$ or $J_3$; and as Z, trifluoromethoxy, 2,2-difluoroethoxy, difluoromethoxy, chloro, 2,2,2-trifluoroethoxy, bromo, iodo or amino.

In an embodiment of each aspect of the invention, the compound of formula I has as $R_1$ hydrogen, methyl, or cyclopropmethyl-; as $R_2$ one of $Y_1$, to $Y_{21}$; as $R_3$ methyl; as $R_4$ $J_1$ or $J_3$; and as $Z_1$ trifluoromethoxy, 2,2-difluoroethoxy, difluoromethoxy, chloro, 2,2,2-trifluoroethoxy, bromo, iodo or amino.

In an embodiment of each aspect of the invention, the compound of formula I has as $R_1$ hydrogen, methyl, or cyclopropmethyl-; as $R_2$ one of $Y_1$, to $Y_{21}$; as $R_3$ methyl; as $R_4$ $J_1$ or $J_3$; and as $Z_1$ trifluoromethoxy, difluoromethoxy, chloro, bromo, iodo or amino.

In a second aspect, the present invention makes available a composition comprising a compound of formula I as defined in the first aspect, one or more auxiliaries and diluent, and optionally one more other active ingredient.

In a third aspect, the present invention makes available a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound as defined in the first aspect or a composition as defined in the second aspect.

In a fourth aspect, the present invention makes available a method for the protection of plant propagation material from the attack by insects, acarines, nematodes or molluscs, which comprises treating the propagation material or the site, where the propagation material is planted, with an effective amount of a compound of formula I as defined in the first aspect or a composition as defined in the second aspect.

In a fifth aspect, the present invention makes available a plant propagation material, such as a seed, comprising, or treated with or adhered thereto, a compound of formula I as defined in the first aspect or a composition as defined in the second aspect.

The present invention in a further aspect provides a method of controlling parasites in or on an animal in need thereof comprising administering an effective amount of a compound of the first aspect. The present invention further provides a method of controlling ectoparasites on an animal in need thereof comprising administering an effective amount of a compound of formula I as defined om the first aspect. The present invention further provides a method for preventing and/or treating diseases transmitted by ectoparasites comprising administering an effective amount of a compound of formula I as defined in the first aspect, to an animal in need thereof.

Compounds of formula I can be prepared by those skilled in the art following known methods. More specifically compounds of formulae I, and I'a, and intermediates therefor can be prepared as described below in the schemes and examples. Certain stereogenic centers have been left unspecified for the clarity and are not intended to limit the teaching of the schemes in any way.

The process according to the invention for preparing compounds of formula I is carried out by methods known to those skilled in the art. Compounds of formula I (I)

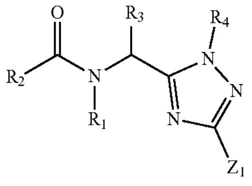

can be prepared by reaction of an amine of formula II (II)

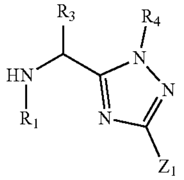

Wherein $R_1$, $R_3$, $R_4$, $Z_1$, are as described in formula I, with a carboxylic acid derivative of formula III (III)

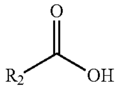

wherein $R_2$ is described as above under formula I. The chemistry is described in more detail in Scheme 1.

Scheme 1

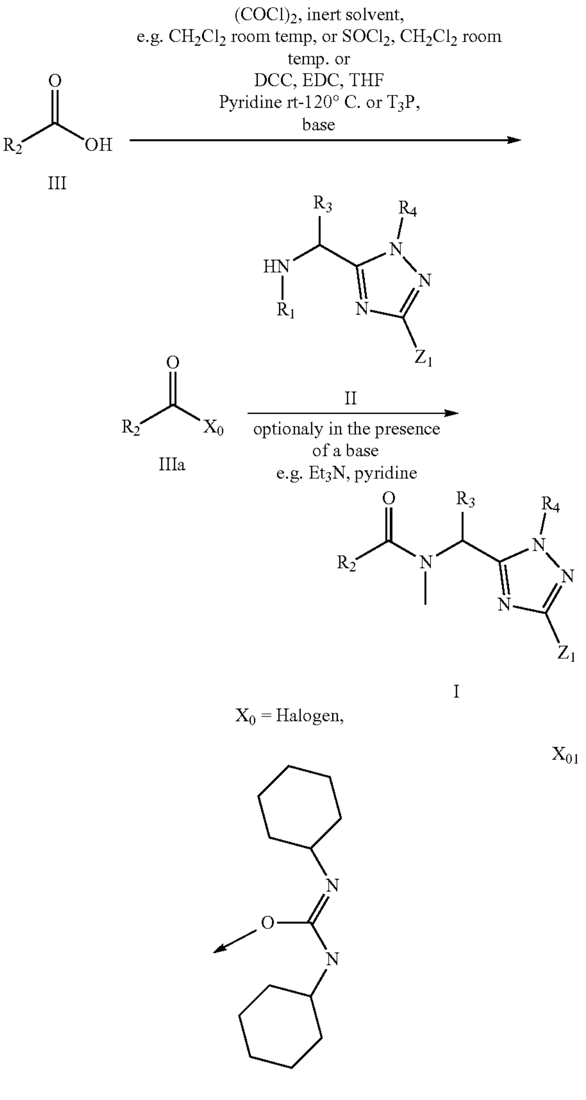

-continued

X02

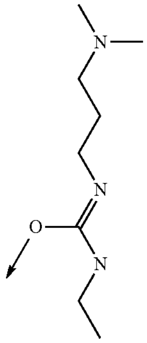

X03

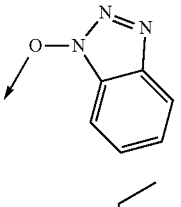

X04

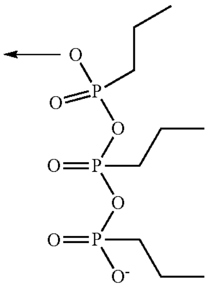

In Scheme 1, compounds of formula III wherein $R_2$ is described in formula I, are activated to compounds of formula IIIa by methods known to those skilled in the art and described for example in *Tetrahedron,* 61 (46), 10827-10852, 2005. For example, compounds where $X_0$ is halogen are formed by treatment of compounds of formula III with for example, oxalyl chloride or thionyl chloride in the presence of catalytic quantities of DMF in inert solvents such as methylene dichloride or THE at temperatures between 20° C. to 100° C., preferably 25° C. Treatment of IIIa with compounds of formula II wherein $R_1$, $R_3$, $R_4$ and $Z_1$ are defined as above, optionally in the presence of a base, e.g. triethylamine or pyridine leads to compounds of formula I. Alternatively, compounds of formula I can be prepared by treatment of compounds of formula III with dicyclohexyl carbodiimide (DCC), 1-Ethyl-3-(3-dimethylaminopropyl) carbodiimide (EDC) or (1-[Bis(dimethylamino)methylene]-1H-1,2,3-triazolo[4,5-b]pyridinium 3-oxide hexafluorophosphate (HATU) to give the activated species IIIa, wherein $X_0$ is $X_{01}$, $X_{02}$ and $X_{03}$ respectively, in an inert solvent, e.g. pyridine, DMF, acetonitrile, $CH_2Cl_2$ or THE optionally in the presence of a base, e.g. triethylamine, at temperatures between 30-180° C. Finally, an acid of the formula III can also be activated by reaction with a coupling reagent such as propanephosphonic acid anhydride (T3P®) to provide compounds of formula IIIa wherein $X_0$ is $X_{04}$ as described for example in *Synthesis* 2013, 45, 1569. Further reaction with an amine of the formula II provides compounds of formula I.

Compounds of formula II, wherein $R_1$, $R_3$, $R_4$ and $Z_1$ are defined as above, are generally known or can be easily prepared by those skilled in the art. A typical example of such a synthesis is shown in scheme 2.

Scheme 2.

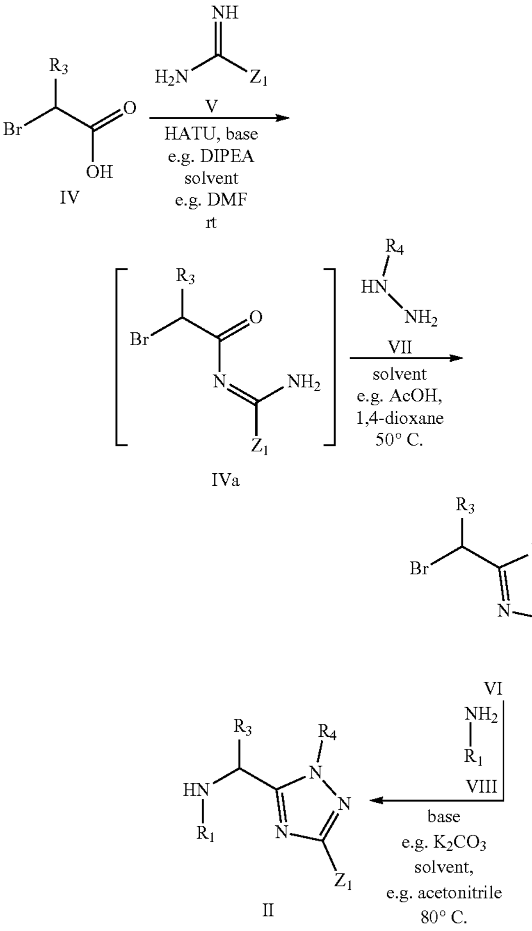

For example, compounds of formula II may be prepared by reaction between compounds of formula VI, wherein $R_3$, $R_4$ and $Z_1$ are as defined in formula I, and compounds of formula VIII, wherein $R_1$ is defined in formula I, in suitable solvents that may include, for example, acetonitrile or dioxane, in the presence of a suitable base, such as sodium, potassium or cesium carbonate (or sodium or potassium hydrogene carbonate), usually upon heating at temperatures between room temperature and 200° C., preferably between 40° C. to the boiling point of the reaction mixture, optionally under microwave heating conditions.

Compounds of formula VI wherein $R_3$, $R_4$ and $Z_1$ are defined as above, may be prepared by reaction between compounds of formula IVa, wherein $R_3$ and $Z_1$ are as defined in formula I, and compounds of formula VII, wherein $R_4$ is defined in formula I, in suitable solvents that may include, for example, mixture of acetic acid and 1,4-dioxane, usually upon heating at temperatures between room temperature and 200° C., preferably between 40° C. to the boiling point of the reaction mixture, optionally under microwave heating conditions. Such processes have been described previously, for example, in *Tetrahedron* 2017, 73, 750.

Compounds of formula IVa wherein $R_3$ and $Z_1$ are defined as above, may be prepared by reaction between compounds of formula IV, wherein $R_3$ is as defined in formula I, and compounds of formula V, wherein $Z_1$ is as defined in formula I, in suitable solvents that may include, for example, DMF, in the presence of a suitable base, such as DIPEA upon heating at temperatures between room temperature and 200°

C., preferably between 20° C. to the boiling point of the reaction mixture. Such processes have been described previously, for example, in *Journal of Organic Chemistry*, 2011, 76, 1177.

Alternatively, compounds of formula I, wherein $R_1$, $R_2$, $R_3$, $R_4$ and $Z_1$ are defined as above, may also be prepared by the process shown in scheme 3.

Scheme 3.

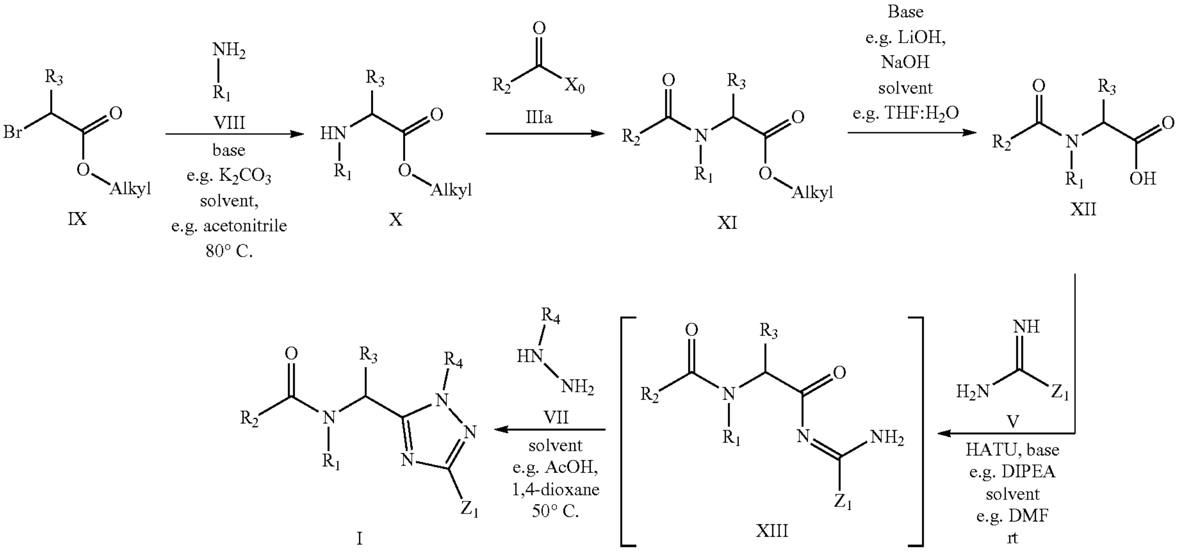

For example, compounds of formula I wherein, $R_1$, $R_2$, $R_3$, $R_4$ and $Z_1$ are defined as above, may be prepared by reaction between compounds of formula XIII wherein, $R_1$, $R_2$, $R_3$ and $Z_1$ are defined as above, and compounds of formula VII, wherein $R_4$ is defined in formula I, in suitable solvents that may include, for example, mixture of acetic acid and 1,4-dioxane, usually upon heating at temperatures between room temperature and 200° C., preferably between 40° C. to the boiling point of the reaction mixture, optionally under microwave heating conditions. Such processes have been described previously, for example, in Tetrahedron 2017, 73, 750.

Compounds of formula XIII wherein, $R_1$, $R_2$, $R_3$ and $Z_1$ are defined as above, may be prepared by reaction between compounds of formula XII wherein, $R_1$, $R_2$ and $R_3$ are defined as above, and compounds of formula V, wherein $Z_1$ is as defined in formula I, in suitable solvents that may include, for example, DMF, in the presence of a suitable base, such as DIPEA upon heating at temperatures between room temperature and 200° C., preferably between 40 to the boiling point of the reaction mixture. Such processes have been described previously, for example, in J. Org. Chem., 2011, 76, 1177.

Compounds of formula XII wherein, $R_1$, $R_2$ and $R_3$ are defined as above, may be prepared by reaction between compounds of formula XI, wherein $R_1$, $R_2$ and $R_3$ are defined as above, and a base, for example lithium hydroxide or sodium hydroxide in suitable solvents that may include, a mixture of THF/$H_2O$ usually upon heating at temperatures between room temperature and 200° C.

Compounds of formula XI wherein, $R_1$, $R_2$ and $R_3$ are defined as above, may be prepared by reaction between compounds of formula IIIa, wherein $R_2$ and $X_0$ are defined as above, and compounds of formula X, wherein $R_1$ and $R_3$ are as defined in formula I, in suitable inert solvents that may include, for example, pyridine, DMF, acetonitrile, $CH_2Cl_2$ or THF, optionally in the presence of a base, e.g. triethylamine or pyridine, usually upon heating at temperatures between room temperature and 200° C. Compounds of formula X, wherein $R_1$ and $R_3$ are defined as above, may be prepared by reaction between compounds of formula IX, wherein $R_3$ is as defined in formula I, and compounds of formula VIII, wherein $R_1$ is defined in formula I, in suitable solvents that may include, for example, acetonitrile or dioxane, in the presence of a suitable base, such as sodium, potassium or caesium carbonate (or sodium or potassium hydrogen carbonate), usually upon heating at temperatures between room temperature and 200° C., preferably between 40° C. to the boiling point of the reaction mixture, optionally under microwave heating conditions.

Alternatively, compounds of formula I, wherein $R_1$, $R_2$, $R_3$, $R_4$ and $Z_1$ are defined as above, may also be prepared by the process shown in scheme 4.

Scheme 4.

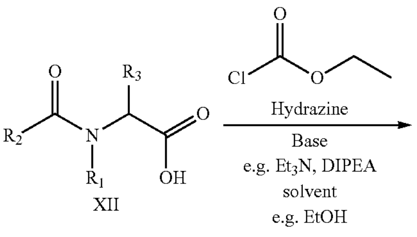

-continued

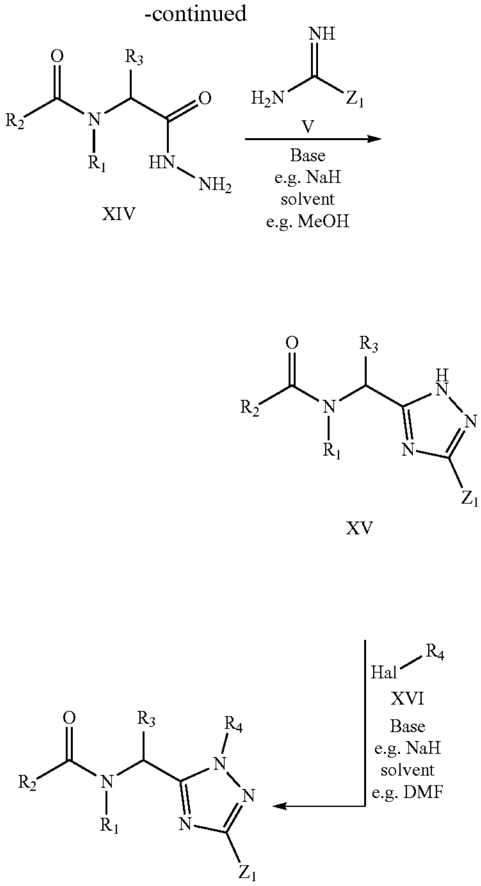

XIV

XV

I

For example, compounds of formula I wherein, $R_1$, $R_2$, $R_3$, $R_4$ and $Z_1$ are defined as above, may be prepared by reaction between compounds of formula XV wherein, $R_1$, $R_2$, $R_3$ and $Z_1$ are defined as above, and compounds of formula XVI, wherein $R_4$ is defined in formula I and wherein Hal is a halogen such as, for example, chlorine, bromine or iodine, optionally in the presence of a copper catalyst, for example, CuI, of a suitable solvent, such as DMF or NMP, in the presence of a suitable base, such as sodium hydride, potassium or caesium carbonate usually upon heating at temperatures between room temperature and 200° C., preferably between 20° C. to the boiling point of the reaction mixture, optionally under microwave heating conditions. Such processes have been described previously, for example, in *Chem. Asian J.* 2014, 9, 166; also in WO2013161904 and WO2009131173.

Compounds of formula XV wherein, $R_1$, $R_2$, $R_3$ and $Z_1$ are defined as above, may be prepared by reaction between compounds of formula XIV, wherein $R_1$, $R_2$ and $R_3$ are defined as above, and compounds of formula V, wherein $Z_1$ is defined as above in the presence of a base, for example sodium hydride in suitable solvents, for example DMF usually upon heating at temperatures between room temperature and 200° C.

Compounds of formula XIV wherein, $R_1$, $R_2$ and $R_3$ are defined as above, may be prepared by reaction between compounds of formula XII, wherein $R_1$, $R_2$ and $R_3$ are defined as above, ethylchloroformate and hydrazine in the presence of a base, for example trimethylamine or DIPEA in suitable solvents, for example methanol or ethanol usually upon heating at temperatures between room temperature and 200° C. Such processes have been described previously, for example, in WO2008055013

Compounds of formula Ia, wherein $R_1$, $R_2$, $R_3$ and $R_4$ are defined as above and Xa is an halogen such as chlorine, bromine or iodine, may be prepared by the process shown in scheme 5.

Scheme 5.

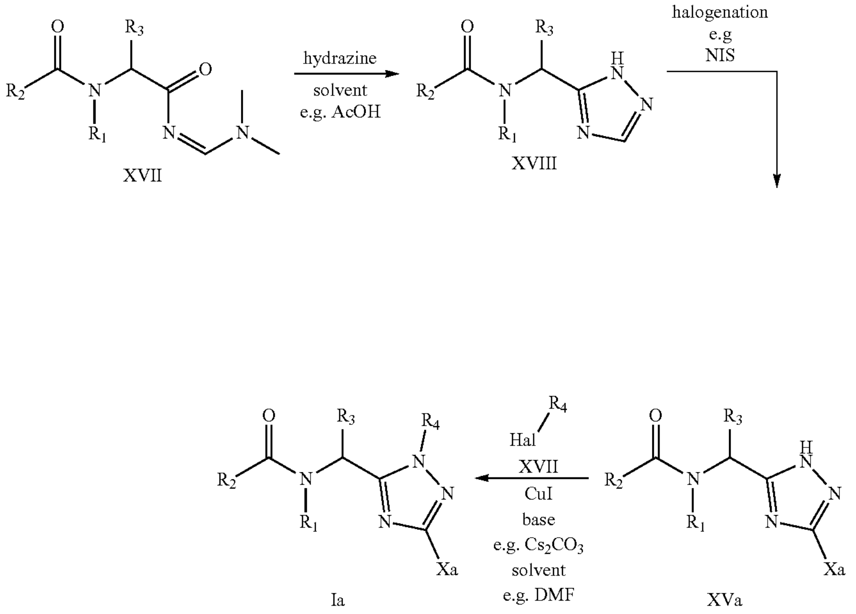

XVII

XVIII

Ia

XVa

For example, compounds of formula Ia, wherein $R_1$, $R_2$, $R_3$ and $R_4$ are defined as above, and Xa is an halogen such as chlorine, bromine or iodine, may be prepared by reaction between compounds of formula XVa wherein, $R_1$, $R_2$ and $R_3$ are defined as above and Xa is an halogen such as chlorine, bromine or iodine, and compounds of formula XVI wherein, $R_4$ is defined as above, and wherein Hal is a halogen such as, for example, chlorine, bromine or iodine, optionally in the presence of a copper catalyst, for example, CuI, of a suitable solvent, such as DMF or NMP, in the presence of a suitable base, such as sodium hydride, potassium or caesium carbonate usually upon heating at temperatures between room temperature and 200° C., preferably between 20° C. to the boiling point of the reaction mixture, optionally under microwave heating conditions. Such processes have been described previously, for example, in *Chem. Asian J.* 2014, 9, 166; also in WO2013161904 and WO2009131173.

Compounds of formula XVa, wherein $R_1$, $R_2$, $R_3$ and Xa are defined as above, may be prepared by halogenation of compounds of formula XVIII wherein, $R_1$, $R_2$ and $R_3$ are defined as above, with a halogenating agent such as, for example, benzyltrimethylammonium tribromide, N-iodosuccinimide in suitable solvents that may include, for example, $CH_2Cl_2$, in the presence of a suitable base, such as sodium, potassium or lithium hydroxide, usually upon heating at temperatures between room temperature and 200° C., preferably between 20° C. to the boiling point of the reaction mixture, optionally under microwave heating conditions. Such processes have been described previously, for example, in US2014206700 (see pages 37-38).

Compounds of formula XVIII, wherein $R_1$, $R_2$ and $R_3$ are defined as above, may be prepared by reaction of compounds of formula XVII wherein, $R_1$, $R_2$ and $R_3$ are defined as above, with hydrazine in suitable solvents that may include, for example, acetic acid, mixture of acetic acid and 1,4-dioxane or mixture of acetic acid and toluene, usually upon heating at temperatures between room temperature and 200° C., preferably between 40° C. to the boiling point of the reaction mixture, optionally under microwave heating conditions. Such processes have been described previously, for example, in *J. Heterocyclic Chem.* 2008, 45, 887; *Bioorg. Med. Chem. Lett.* 2015, 25, 5121.

Intermediates of formula XVII, wherein $R_1$, $R_2$ and $R_3$ are defined as above, may be prepared by the process shown in scheme 6.

Scheme 6.

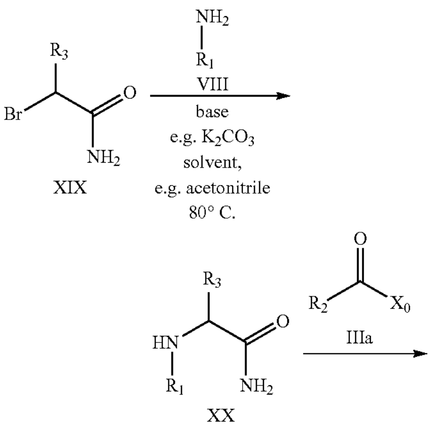

XIX

XX

-continued

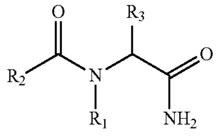

XXI

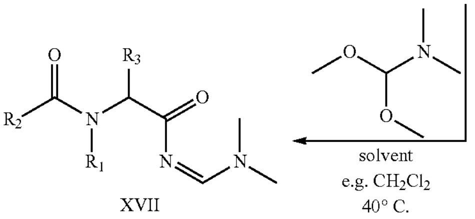

XVII

Compounds of formula XVII wherein, $R_1$, $R_2$ and $R_3$ are defined as above, may be prepared by reaction between compounds of formula XXI wherein, $R_1$, $R_2$ and $R_3$ are defined as above, and N,N-dimethylformamide dimethyl acetal (DMF-DMA), in suitable solvents that may include, for example, dichloromethane, usually upon heating at temperatures between room temperature and 200° C., preferably between 40° C. to the boiling point of the reaction mixture. Such processes have been described previously, for example, in *Tetrahedron* 2017, 73, 750, and US2016296501, preparation 7, page 29.

Compounds of formula XXI wherein, $R_1$, $R_2$ and $R_3$ are defined as above, may be prepared by reaction between compounds of formula XX, wherein $R_1$ and $R_3$ are defined as above, and compounds of formula IIIa, wherein $R_2$ and $X_0$ are defined as in Scheme 1, in suitable inert solvents that may include, for example, pyridine, DMF, acetonitrile, $CH_2Cl_2$ or THF, optionally in the presence of a base, e.g. triethylamine or pyridine, usually upon heating at temperatures between room temperature and 200° C.

Compounds of formula XX, wherein $R_1$ and $R_3$ are defined as above, may be prepared by reaction between compounds of formula XIX, wherein $R_3$ is as defined in formula I, and compounds of formula VIII, wherein $R_1$ is defined in formula I, in suitable solvents that may include, for example, acetonitrile or dioxane, in the presence of a suitable base, such as sodium, potassium or caesium carbonate (or sodium or potassium hydrogen carbonate), usually upon heating at temperatures between room temperature and 200° C., preferably between 40° C. to the boiling point of the reaction mixture, optionally under microwave heating conditions.

Alternatively, Compounds of formula I wherein, $R_1$, $R_2$, $R_3$, $R_4$ are defined as above and $Z_{1a}$ is diphenylmethanimine, $C_3$-$C_4$halocycloalkyl, $C_3$-$C_4$cyanocycloalkyl, $C_2$-$C_6$alkenyl, $C_2$-$C_6$alkoxyalkenyl, $C_2$-$C_6$haloalkenyl, $C_2$-$C_6$alkynyl, $C_2$-$C_6$haloalkynyl, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxy, may be prepared by the process shown in scheme 7.

Scheme 7

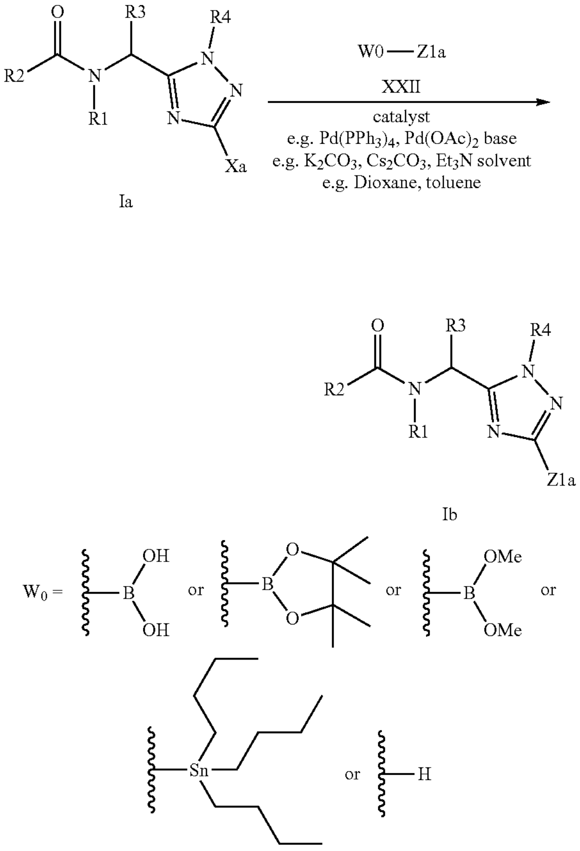

Ia

Ib

Compounds of formula I wherein, $R_1$, $R_2$, $R_3$, $R_4$ are defined as above and Zia is diphenylmethanimine, $C_3$-$C_4$halocycloalkyl, $C_3$-$C_4$cyanocycloalkyl, $C_2$-$C_6$alkenyl, $C_2$-$C_6$alkoxyalkenyl, $C_2$-$C_6$haloalkenyl, $C_2$-$C_6$alkynyl, $C_2$-$C_6$haloalkynyl, phenyl or a 5-membered heteroaromatic ring wherein the phenyl or the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxy; may be prepared by reaction of compounds of formula Ia wherein $R_1$, $R_2$, $R_3$, $R_4$ and $X_a$ are previously described and compounds of formula XXII wherein $Z_{1a}$ is described above and $W_0$ is a boronic acid or a boronate ester or a tin compound or hydrogen as depicted in scheme 7. This reaction is carried on in the presence of a palladium catalyst, for example, $Pd(PPh_3)_4$, of a suitable solvent, such as dioxane or toluene, in the presence of a suitable base, such as potassium or caesium carbonate usually upon heating at temperatures between room temperature and 200° C., preferably between 20° C. to the boiling point of the reaction mixture, optionally under microwave heating conditions. Such processes have been described previously, for example, in WO2016006523 or *J. Med. Chem.*, 2014, 57, 3687-3706.

Compounds of formula Ic, wherein $R_1$, $R_2$, $R_3$, $R_4$ are defined as above and $Z_{1b}$ is amino, ($C_1$-$C_3$alkyl)sulfonylamino, ($C_1$-$C_3$alkyl)sulfonyl($C_1$-$C_3$alkyl)amino, ($C_1$-$C_3$alkyl)C(O)($C_1$-$C_3$alkyl)N or ($C_1$-$C_3$alkyl)C(O)NH, may be prepared by the process shown in scheme 8.

Scheme 8.

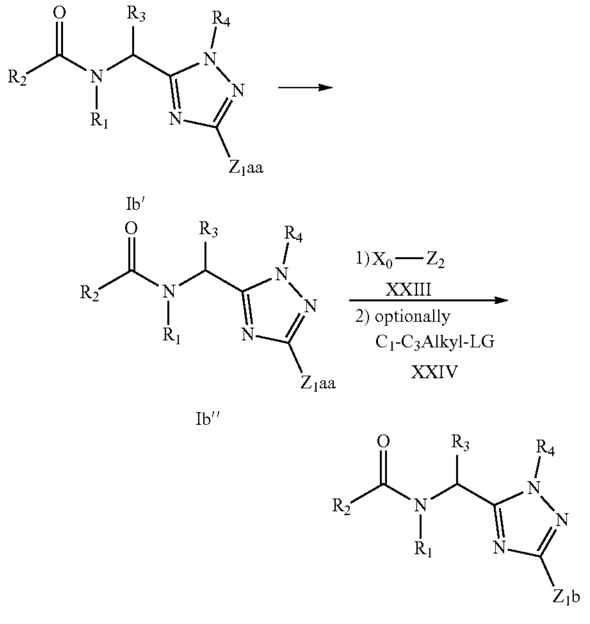

Ib'

Ib''

Ic

Compounds of formula Ic, wherein $R_1$, $R_2$, $R_3$, $R_4$ are defined as above and $Z_{1b}$ is ($C_1$-$C_3$alkyl)amino, ($C_1$-$C_3$alkyl)sulfonylamino, ($C_1$-$C_3$alkyl)sulfonyl($C_1$-$C_3$alkyl)amino, ($C_1$-$C_3$alkyl)C(O)($C_1$-$C_3$alkyl)N or ($C_1$-$C_3$alkyl)C(O)NH, may be prepared by reaction between compound Ib" wherein $R_1$, $R_2$, $R_3$, $R_4$ are defined as above and compound XXIII wherein $X_0$ is described in scheme 1 and can also be $X_{01}$, $X_{02}$, $X_{03}$ and $X_{04}$ as described in scheme 1 and $Z_2$ is ($C_1$-$C_3$alkyl), ($C_1$-$C_3$alkyl)sulfonyl or ($C_1$-$C_3$alkyl)C(O). The reaction is carried on in a suitable solvent, such as dichloromethane or DMF, in the presence of a suitable base, such as trimethylamine or pyridine usually upon heating at temperatures between room temperature and 200° C., preferably between 20° C. to the boiling point of the reaction mixture. The resulting compound can be optionally alkylated in a second step by treatment of this later with compound XXIV wherein LG is a leaving group such as chlorine, mesyloxy or tosyloxy in a suitable solvent, such as THE or DMF, in the presence of a suitable base, such as sodium hydride usually upon heating at temperatures between room temperature and 200° C., preferably between 20° C. to the boiling point of the reaction mixture. Such transformation are easily made by those skilled in the art or care described in WO2010010186 or *Eur. J. Med. Chem,* 2013, 67, 243-251.

Compounds of formula Ib" wherein $R_1$, $R_2$, $R_3$, $R_4$ are defined as above, can be prepared by transformation of compound Ib' wherein $R_1$, $R_2$, $R_3$, $R_4$ are defined as above and $Z_{1aa}$ is diphenylmethanimine. This reaction is carried on in a suitable solvent, such as THF, in the presence of an acid, such as hydrogen chloride or citric acid, usually upon heating at temperatures between room temperature and 200° C., preferably between 20° C. to the boiling point of the reaction mixture. Such processes have been described previously, for example, in WO2018067432 or *Eur. J. Med. Chem,* 2018, 144, 151-163.

Compounds of formula Id wherein, $R_1$, $R_2$, $R_3$, $R_4$ are defined as above and $Z_{1c}$ is an halogen such as chlorine, bromine or iodine, CN, ($C_1$-$C_3$alkyl)amino, $C_2$-$C_6$alkenyl, or $C_1$-$C_4$alkylsulfanyl, may be prepared by the process shown in Scheme 9.

Scheme 9.

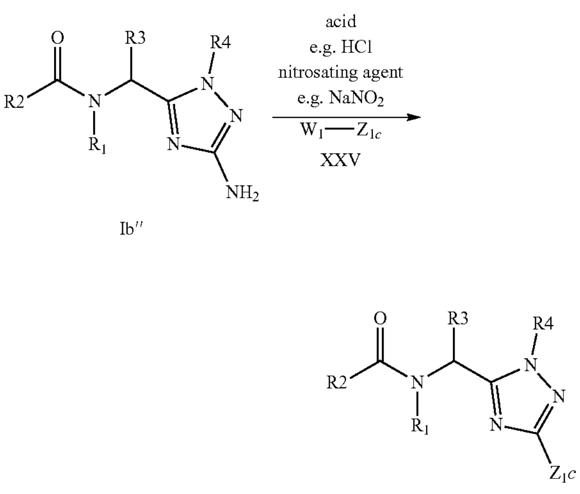

Ib''

Id

Compounds of formula Id wherein $R_1$, $R_2$, $R_3$, $R_4$ are defined as above and $Z_{1c}$ is an halogen such as chlorine, bromine or iodine, CN, ($C_1$-$C_3$alkyl)amino, $C_2$-$C_6$alkenyl, or $C_1$-$C_4$alkylsulfanyl, may be prepared by reaction between compounds of formula Ib' wherein $R_1$, $R_2$, $R_3$ and $R_4$ are previously described and compounds of formula XXV wherein $Z_{1c}$ is described above and $W_1$ is a hydrogen, an alkali metal or copper. The reaction is carried by treating compounds of formula Ib' with a suitable nitrosating agent such as sodium nitrite, tert-butyl nitrite or isoamyl nitrite in presence of a suitable acid such as hydrochloric acid, sulfuric acid or tetrafluoroboric acid in a suitable solvent such as acetonitrile or water, usually at temperature between 0° and room temperature. The diazonium intermediate is treated with a compound of formula XXV wherein $Z_{1c}$ and $W_1$ are described above usually upon heating at temperatures between room temperature and 200° C., preferably between 20° C. to the boiling point of the reaction mixture. Such processes have been described previously, for example, in WO2010141796 or J. Med. Chem. 1990, 33, 1230-41.

Compounds of formula Ie wherein, $R_1$, $R_2$, $R_3$, $R_4$ are defined as above and $Z_{1d}$ is hydroxy, $C_1$-$C_3$alkoxy-$C_1$-$C_3$alkyl or $C_1$-$C_3$haloalkoxy may be prepared by the process shown in Scheme 10.

Scheme 10.

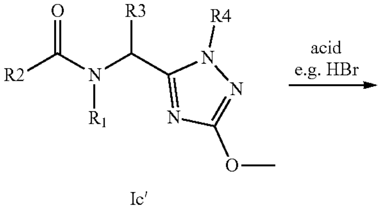

Ic'

-continued

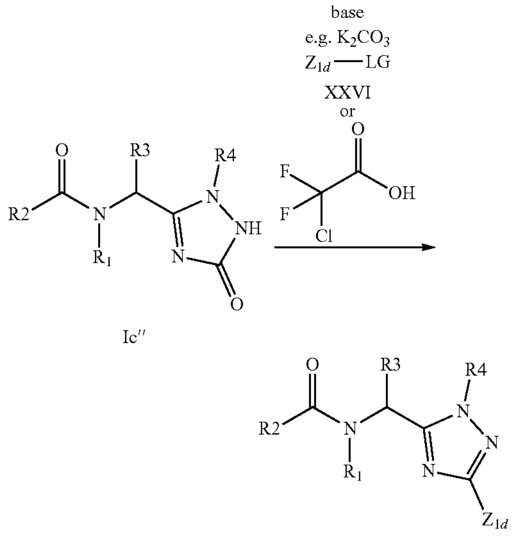

Ic''

Ie

Compounds of formula Ie wherein $R_1$, $R_2$, $R_3$, $R_4$ are defined as above and $Z_{1d}$ is hydroxy, $C_1$-$C_3$alkoxy-$C_1$-$C_3$alkyl or $C_1$-$C_3$haloalkoxy may be prepared by reaction between compounds of formula Ic" wherein $R_1$, $R_2$, $R_3$ and $R_4$ are previously described and compounds of formula XXVI wherein $Z_{1d}$ is described above and LG is a leaving group such as chlorine, triflate, mesyloxy or tosyloxy, or alternatively by reaction between compounds Ic" described above and 2-chloro-2,2-difluoro-acetic acid. The reaction is carried on in a suitable solvent, such as acetonitrile or DMF, in the presence of a suitable base, such as triethylamine or potassium carbonate usually upon heating at temperatures between room temperature and 200° C., preferably between 20° C. to the boiling point of the reaction mixture.

Compounds of formula Ic" may be prepared by treating compound of formula Ic' wherein $R_1$, $R_2$, $R_3$ and $R_4$ are previously described with a suitable acid such as hydrobromic acid or hydrochloric acid in a suitable solvent such as acetic acid or water usually upon heating at temperatures between room temperature and 200° C., preferably between 20° C. to the boiling point of the reaction mixture. Such processes have been described previously, for example, in US20090291967 or Bioorganic & Medicinal Chemistry 2018, 26, 3321-3344.

Compounds of formula $III_1$ wherein $R_2$ is $Y_1$, $Y_3$, $Y_5$ or $Y_{11}$ are commercially available and were not prepared by our self.

Compound of formula $III_2$ wherein $R_2$ is $Y_6$, may be prepared by the process shown in scheme 11

Scheme 11.

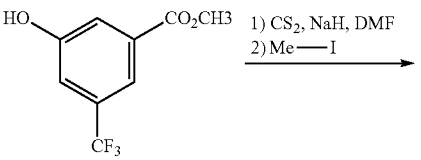

XXVII

-continued

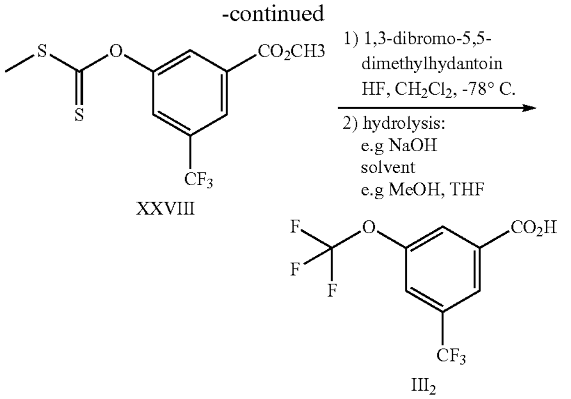

XXVIII $III_2$

Compound of formula $III_2$ wherein $R_2$ is Ye may be prepared by transformation of compound XXVIII by treatment with 1,3-dibromo-5,5-dimethylhydanthoin and hydrogen fluoride, in suitable solvents that may include, for example, dichloromethane, usually at low temperature between −78° C. and 0° C. The resulting compound is then hydrolyzed into the corresponding carboxylic acid by using classical conditions known by those skilled in the art (sodium or lithium hydroxide, MeOH/THF/$H_2O$).

Compound of formula XXVIII may be prepared by reaction of compound XXVII with carbon disulfide in suitable solvents that may include, for example, DMF, in the presence of a suitable base, such as sodium, hydride, usually upon heating at temperatures between room temperature and 200° C., followed by a methylation step involving methyl iodide as methylation agent. Such processes have been described previously, for example, in Bioorg. Med. Chem. 2007, 17, 4308 and other conditions can be found, for example, in J. Fluorine Chem. 2015, 179, 48 or Chem. Soc. Jp. 2000, 73, 471.

Compound of formula $III_3$ wherein $R_2$ is $Y_{13}$, may be prepared by the process shown in scheme 12

Scheme 12.

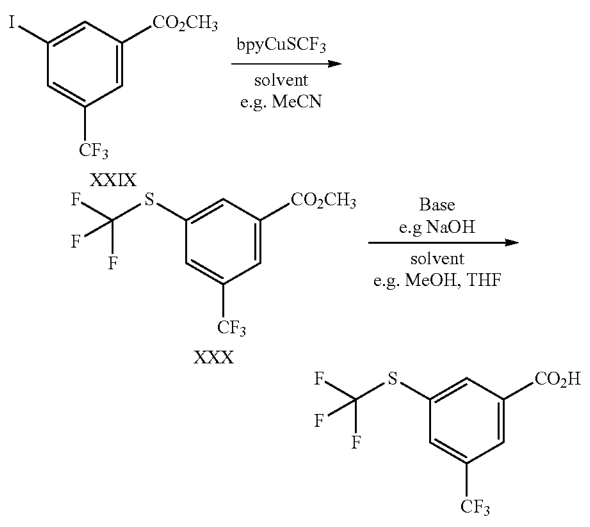

XXIX

XXX $III_3$

Compound of formula $III_3$ wherein $R_2$ is $Y_{13}$, may be prepared by reaction of compound XXX with a suitable base such as, sodium or lithium hydroxide, in a suitable solvent like MeOH, THF, $H_2O$ or a mix of the 3, usually upon heating at temperatures between room temperature and reflux.

Compound of formula XXX, may be prepared by reaction of compound XXIX with a suitable trifluoromethylthiolation copper reagent such as, (bpy)CuSCF3, in suitable solvents that may include, for example, acetonitrile, usually upon heating at temperatures between room temperature and 200° C., preferably between 40° C. to the boiling point of the reaction mixture. Such processes have been described previously, for example, in *Angew. Chem. Int. Ed.* 2013, 52, 1548-1552.

Compound of formula $III_4$ wherein $R_2$ is $Y_{15}$, may be prepared by the process shown in scheme 13

Scheme 13.

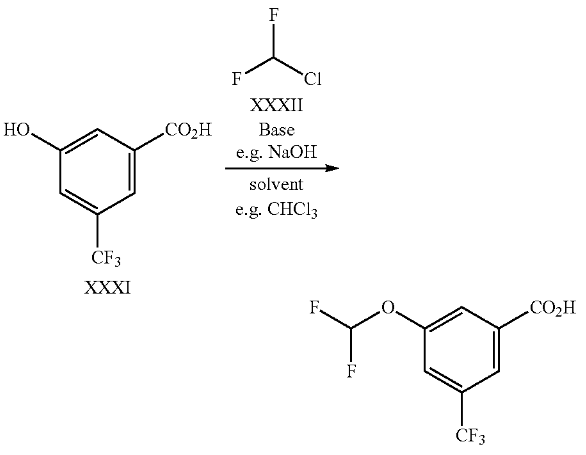

XXXI $III_4$

Compound of formula $III_4$ wherein $R_2$ is $Y_{15}$, may be prepared by reaction of compound XXXI with compound XXXII in suitable solvents that may include, for example, chloroform, in the presence of a suitable base, such as sodium hydroxide, usually upon heating at temperatures between room temperature and reflux. Such processes have been described previously, for example, in WO2002044145.

Depending on the procedure or the reaction conditions, the reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reactions are advantageously carried out in a temperature range from approximately −80° C. to approximately +140° C., preferably from approximately −30° C. to approximately +100° C., in many cases in the range between ambient temperature and approximately +80° C.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.*, 32 (12), 2561-73, 1989 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

In a further aspect, the present invention makes available compounds of formula XV

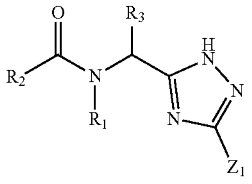

(XV)

wherein $R_1$, $R_2$, $R_3$ and $Z_1$ are as defined in the first aspect for formula (I); or a stereoisomer, enantiomer, tautomer and N-oxide of the compound of formula I, or agrochemically acceptable salt thereof. The embodiments described for $R_1$, $R_2$, $R_3$ and $Z_1$ in respect of formula (I) are also applicable to formula (XV).

In a preferred embodiment, compound of formula XV has as $R_2$ embodiment L; as $R_1$ embodiment L, as $R_3$ embodiment C; and as $Z_1$ one of embodiments A to M.

In a further aspect, the present invention makes available compounds of formula II

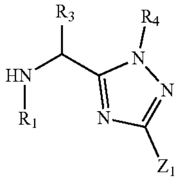

(II)

wherein $R_1$, $R_3$, $R_4$ and $Z_1$ are as defined in the first aspect for formula (I); or a stereoisomer, enantiomer, tautomer and N-oxide of the compound of formula I, or agrochemically acceptable salt thereof. The embodiments described for $R_1$, $R_2$, $R_3$ and $Z_1$ in respect of formula (I) are also applicable to formula (II).

In a preferred embodiment, compound of formula II has as $R_1$ embodiment L, as $R_3$ embodiment C; as $R_4$ embodiment G; and as Z, one of embodiments A to P.

The compounds of formula I according to the following Tables A-1 to A-92 can be prepared according to the methods described above. The examples which follow are intended to illustrate the invention and show preferred compounds of formula I, in the form of a compound of formula Ia Iaa

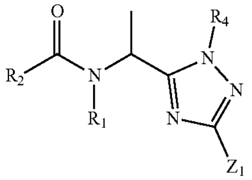

Table A-1 provides 45 compounds A-1.001 to A-1.045 of formula Iaa wherein $R_1$ is H, $R_2$ is [3,5-bis(trifluoromethyl)phenyl], $R_4$ is 2-pyridyl and $Z_1$ is as defined in table Z. For example, A-1.009 is

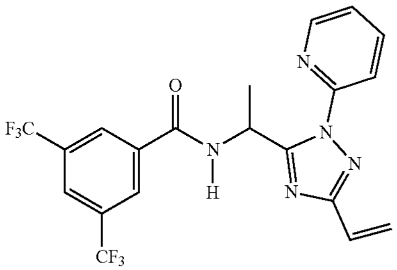 [SMILES: C=Cc1nc(C(C)NC(=O)c2cc(C(F)(F)F)cc(C(F)(F)F)c2)n(-c2ccccn2)n1]

TABLE Z

| Substituent definitions of Z1: | |
|---|---|
| Index | Z1 |
| 1 | Br |
| 2 | Cl |
| 3 | CN |
| 4 | $NH_2$ |

TABLE Z-continued

| Substituent definitions of Z1: | |
|---|---|
| Index | Z1 |
| 5 | $NHCH_3$ |
| 6 | OH |
| 7 | 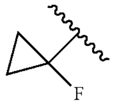 [SMILES: *C1(F)CC1] |
| 8 | 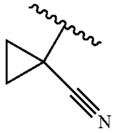 [SMILES: *C1(C#N)CC1] |
| 9 | 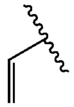 |
| 10 | 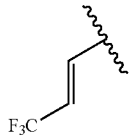 |
| 11 | 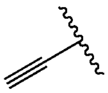 [SMILES: *C#C] |
| 12 | 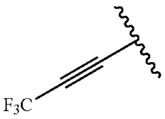 [SMILES: *C#CC(F)(F)F] |
| 13 | $SCF_3$ |
| 14 | 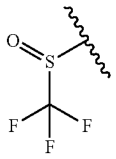 [SMILES: *S(=O)C(F)(F)F] |
| 15 | 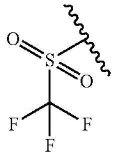 |
| 16 | $SCH_3$ |
| 17 | 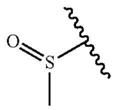 [SMILES: *S(C)=O] |
| 18 | 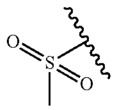 [SMILES: *S(C)(=O)=O] |

TABLE Z-continued
| Substituent definitions of Z1: | |
|---|---|
| Index | Z1 |
| 19 | 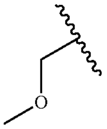 [SMILES: *COC] |
| 20 | 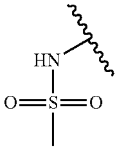 [SMILES: *NS(C)(=O)=O] |
| 21 | 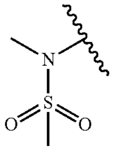 [SMILES: *N(C)S(C)(=O)=O] |
| 22 | 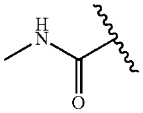 [SMILES: *C(=O)NC] |
| 23 | 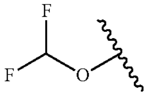 [SMILES: *OC(F)F] |
| 24 | 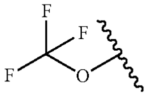 [SMILES: *OC(F)(F)F] |
| 25 | 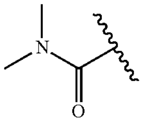 [SMILES: *C(=O)N(C)C] |
| 26 | 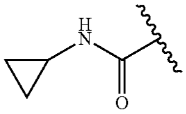 [SMILES: *C(=O)NC1CC1] |
| 27 | 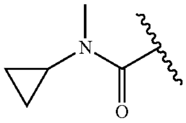 [SMILES: *C(=O)N(C)C1CC1] |
| 28 | 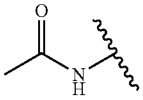 [SMILES: *NC(C)=O] |
| 29 | 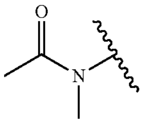 [SMILES: *N(C)C(C)=O] |
TABLE Z-continued
| Substituent definitions of Z1: | |
|---|---|
| Index | Z1 |
| 30 | 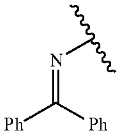 |
| 31 | 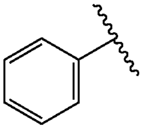 [SMILES: *c1ccccc1] |
| 32 | 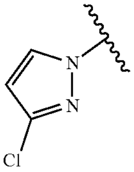 [SMILES: *n1ccc(Cl)n1] |
| 33 | 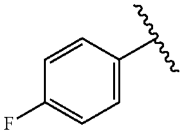 [SMILES: *c1ccc(F)cc1] |
| 34 | 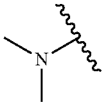 [SMILES: *N(C)C] |
| 35 | 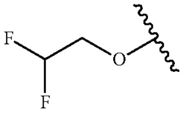 |
| 36 | 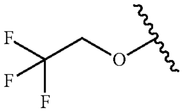 [SMILES: *OCC(F)(F)F] |
| 37 | 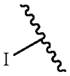 |
| 38 | 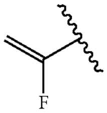 [SMILES: *C(=C)F] |
| 39 | 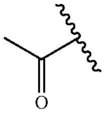 [SMILES: *C(C)=O] |
| 40 | 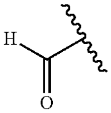 |

TABLE Z-continued

| Substituent definitions of Z1: | |
|---|---|
| Index | Z1 |
| 41 | 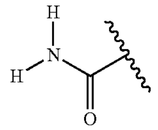 |
| 42 | 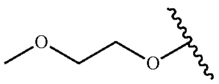 [SMILES: *OCCOC] |
| 43 | 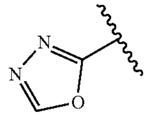 [SMILES: *c1nnco1] |
| 44 | 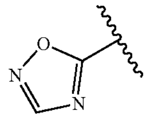 [SMILES: *c1ncno1] |
| 45 | 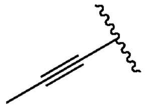 [SMILES: *C#CC] |

Table A-2 provides 45 compounds A-2.001 to A-2.045 of formula Iaa wherein $R_1$ is H, $R_2$ is [3,5-bis(trifluoromethyl) phenyl], $R_4$ is (5-bromo-2-pyridyl) and $Z_1$ is as defined in table Z.

Table A-3 provides 45 compounds A-3.001 to A-3.045 of formula Iaa wherein $R_1$ is H, $R_2$ is [3,5-bis(trifluoromethyl) phenyl], $R_4$ is pyrimidin-2-yl and $Z_1$ is as defined in table Z.

Table A-4 provides 45 compounds A-4.001 to A-4.045 of formula Iaa wherein $R_1$ is H, $R_2$ is [3,5-bis(trifluoromethyl) phenyl], $R_4$ is (5-bromopyrimidin-2-yl) and $Z_1$ is as defined in table Z.

Table A-5 provides 45 compounds A-5.001 to A-5.045 of formula Iaa wherein $R_1$ is H, $R_2$ is [3-chloro-5-(trifluoromethyl)phenyl], $R_4$ is 2-pyridyl and $Z_1$ is as defined in table Z.

Table A-6 provides 45 compounds A-6.001 to A-6.045 of formula Iaa wherein $R_1$ is H, $R_2$ is [3-chloro-5-(trifluoromethyl)phenyl], $R_4$ is (5-bromo-2-pyridyl) and $Z_1$ is as defined in table Z.

Table A-7 provides 45 compounds A-7.001 to A-7.045 of formula Iaa wherein $R_1$ is H, $R_2$ is [3-chloro-5-(trifluoromethyl)phenyl], $R_4$ is pyrimidin-2-yl and $Z_1$ is as defined in table Z.

Table A-8 provides 45 compounds A-8.001 to A-8.045 of formula Iaa wherein $R_1$ is H, $R_2$ is [3-chloro-5-(trifluoromethyl)phenyl], $R_4$ is (5-bromopyrimidin-2-yl) and $Z_1$ is as defined in table Z.

Table A-9 provides 45 compounds A-9.001 to A-9.045 of formula Iaa wherein $R_1$ is H, $R_2$ is [3-chloro-5-(trifluoromethoxy)phenyl], $R_4$ is 2-pyridyl and $Z_1$ is as defined in table Z.

Table A-10 provides 45 compounds A-10.001 to A-10.045 of formula Iaa wherein $R_1$ is H, $R_2$ is [3-chloro-5-(trifluoromethoxy)phenyl], $R_4$ is (5-bromo-2-pyridyl) and $Z_1$ is as defined in table Z.

Table A-11 provides 45 compounds A-11.001 to A-11.045 of formula Iaa wherein $R_1$ is H, $R_2$ is [3-chloro-5-(trifluoromethoxy)phenyl], $R_4$ is pyrimidin-2-yl and $Z_1$ is as defined in table Z.

Table A-12 provides 45 compounds A-12.001 to A-12.045 of formula Iaa wherein $R_1$ is H, $R_2$ is [3-chloro-5-(trifluoromethoxy)phenyl], $R_4$ is (5-bromopyrimidin-2-yl) and $Z_1$ is as defined in table Z.

Table A-13 provides 45 compounds A-13.001 to A-13.045 of formula Iaa wherein $R_1$ is H, $R_2$ is [3-(trifluoromethoxy)-5-(trifluoromethyl)phenyl], $R_4$ is 2-pyridyl and $Z_1$ is as defined in table Z.

Table A-14 provides 45 compounds A-14.001 to A-14.045 of formula Iaa wherein $R_1$ is H, $R_2$ is [3-(trifluoromethoxy)-5-(trifluoromethyl)phenyl], $R_4$ is (5-bromo-2-pyridyl) and $Z_1$ is as defined in table Z.

Table A-15 provides 45 compounds A-15.001 to A-15.045 of formula Iaa wherein $R_1$ is H, $R_2$ is [3-(trifluoromethoxy)-5-(trifluoromethyl)phenyl], $R_4$ is pyrimidin-2-yl and Z, is as defined in table Z.

Table A-16 provides 45 compounds A-16.001 to A-16.045 of formula Iaa wherein $R_1$ is H, $R_2$ is [3-(trifluoromethoxy)-5-(trifluoromethyl)phenyl], $R_4$ is (5-bromopyrimidin-2-yl) and $Z_1$ is as defined in table Z.

Table A-17 provides 45 compounds A-17.001 to A-17.045 of formula Iaa wherein $R_1$ is H, $R_2$ is [3-bromo-5-(trifluoromethyl)phenyl], $R_4$ is 2-pyridyl and $Z_1$ is as defined in table Z.

Table A-18 provides 45 compounds A-18.001 to A-18.045 of formula Iaa wherein $R_1$ is H, $R_2$ is [3-bromo-5-(trifluoromethyl)phenyl], $R_4$ is (5-bromo-2-pyridyl) and $Z_1$ is as defined in table Z.

Table A-19 provides 45 compounds A-19.001 to A-19.045 of formula Iaa wherein $R_1$ is H, $R_2$ is [3-bromo-5-(trifluoromethyl)phenyl], $R_4$ is pyrimidin-2-yl and $Z_1$ is as defined in table Z.

Table A-20 provides 45 compounds A-20.001 to A-20.045 of formula Iaa wherein $R_1$ is H, $R_2$ is [3-bromo-5-(trifluoromethyl)phenyl], $R_4$ is (5-bromopyrimidin-2-yl) and $Z_1$ is as defined in table Z.

Table A-21 provides 45 compounds A-21.001 to A-21.045 of formula Iaa wherein $R_1$ is H, $R_2$ is [3-(trifluoromethyl)-5-(trifluoromethylsulfanyl)phenyl], $R_4$ is 2-pyridyl and $Z_1$ is as defined in table Z.

Table A-22 provides 45 compounds A-22.001 to A-22.045 of formula Iaa wherein $R_1$ is H, $R_2$ is [3-(trifluoromethyl)-5-(trifluoromethylsulfanyl)phenyl], $R_4$ is (5-bromo-2-pyridyl) and $Z_1$ is as defined in table Z.

Table A-23 provides 45 compounds A-23.001 to A-23.045 of formula Iaa wherein $R_1$ is H, $R_2$ is [3-(trifluoromethyl)-5-(trifluoromethylsulfanyl)phenyl], $R_4$ is pyrimidin-2-yl and $Z_1$ is as defined in table Z.

Table A-24 provides 45 compounds A-24.001 to A-24.045 of formula Iaa wherein $R_1$ is H, $R_2$ is [3-(trifluoromethyl)-5-(trifluoromethylsulfanyl)phenyl], $R_4$ is (5-bromopyrimidin-2-yl) and $Z_1$ is as defined in table Z.

Table A-25 provides 45 compounds A-25.001 to A-25.045 of formula Iaa wherein $R_1$ is H, $R_2$ is [3-(difluoromethoxy)-5-(trifluoromethyl)phenyl], $R_4$ is 2-pyridyl and $Z_1$ is as defined in table Z.

Table A-26 provides 45 compounds A-26.001 to A-26.045 of formula Iaa wherein $R_1$ is H, $R_2$ is [3-(difluoromethoxy)-5-(trifluoromethyl)phenyl], $R_4$ is (5-bromo-2-pyridyl) and $Z_1$ is as defined in table Z.

Table A-27 provides 45 compounds A-27.001 to A-27.045 of formula Iaa wherein $R_1$ is H, $R_2$ is [3-(difluoromethoxy)-5-(trifluoromethyl)phenyl], $R_4$ is pyrimidin-2-yl and $Z_1$ is as defined in table Z.

Table A-28 provides 45 compounds A-28.001 to A-28.045 of formula Iaa wherein $R_1$ is H, $R_2$ is [3-(difluoromethoxy)-

5-(trifluoromethyl)phenyl], $R_4$ is (5-bromopyrimidin-2-yl) and $Z_1$ is as defined in table Z.

Table A-29 provides 45 compounds A-29.001 to A-29.045 of formula Iaa wherein $R_1$ is $CH_3$, $R_2$ is [3,5-bis(trifluoromethyl)phenyl], $R_4$ is 2-pyridyl and $Z_1$ is as defined in table Z.

Table A-30 provides 45 compounds A-30.001 to A-30.045 of formula Iaa wherein $R_1$ is $CH_3$, $R_2$ is [3,5-bis(trifluoromethyl)phenyl], $R_4$ is (5-bromo-2-pyridyl) and $Z_1$ is as defined in table Z.

Table A-31 provides 45 compounds A-31.001 to A-31.045 of formula Iaa wherein $R_1$ is $CH_3$, $R_2$ is [3,5-bis(trifluoromethyl)phenyl], $R_4$ is pyrimidin-2-yl and $Z_1$ is as defined in table Z.

Table A-32 provides 45 compounds A-32.001 to A-32.045 of formula Iaa wherein $R_1$ is $CH_3$, $R_2$ is [3,5-bis(trifluoromethyl)phenyl], $R_4$ is (5-bromopyrimidin-2-yl) and Z, is as defined in table Z.

Table A-33 provides 45 compounds A-33.001 to A-33.045 of formula Iaa wherein $R_1$ is $CH_3$, $R_2$ is [3-chloro-5-(trifluoromethyl)phenyl], $R_4$ is 2-pyridyl and $Z_1$ is as defined in table Z.

Table A-34 provides 45 compounds A-34.001 to A-34.045 of formula Iaa wherein $R_1$ is $CH_3$, $R_2$ is [3-chloro-5-(trifluoromethyl)phenyl], $R_4$ is (5-bromo-2-pyridyl) and $Z_1$ is as defined in table Z.

Table A-35 provides 45 compounds A-35.001 to A-35.045 of formula Iaa wherein $R_1$ is $CH_3$, $R_2$ is [3-chloro-5-(trifluoromethyl)phenyl], $R_4$ is pyrimidin-2-yl and $Z_1$ is as defined in table Z.

Table A-36 provides 45 compounds A-36.001 to A-36.045 of formula Iaa wherein $R_1$ is $CH_3$, $R_2$ is [3-chloro-5-(trifluoromethyl)phenyl], $R_4$ is (5-bromopyrimidin-2-yl) and $Z_1$ is as defined in table Z.

Table A-37 provides 45 compounds A-37.001 to A-37.045 of formula Iaa wherein $R_1$ is $CH_3$, $R_2$ is [3-chloro-5-(trifluoromethoxy)phenyl], $R_4$ is 2-pyridyl and $Z_1$ is as defined in table Z.

Table A-38 provides 45 compounds A-38.001 to A-38.045 of formula Iaa wherein $R_1$ is $CH_3$, $R_2$ is [3-chloro-5-(trifluoromethoxy)phenyl], $R_4$ is (5-bromo-2-pyridyl) and $Z_1$ is as defined in table Z.

Table A-39 provides 45 compounds A-39.001 to A-39.045 of formula Iaa wherein $R_1$ is $CH_3$, $R_2$ is [3-chloro-5-(trifluoromethoxy)phenyl], $R_4$ is pyrimidin-2-yl and $Z_1$ is as defined in table Z.

Table A-40 provides 45 compounds A-40.001 to A-40.045 of formula Iaa wherein $R_1$ is $CH_3$, $R_2$ is [3-chloro-5-(trifluoromethoxy)phenyl], $R_4$ is (5-bromopyrimidin-2-yl) and $Z_1$ is as defined in table Z.

Table A-41 provides 45 compounds A-41.001 to A-41.045 of formula Iaa wherein $R_1$ is $CH_3$, $R_2$ is [3-(trifluoromethoxy)-5-(trifluoromethyl)phenyl], $R_4$ is 2-pyridyl and $Z_1$ is as defined in table Z.

Table A-42 provides 45 compounds A-42.001 to A-42.045 of formula Iaa wherein $R_1$ is $CH_3$, $R_2$ is [3-(trifluoromethoxy)-5-(trifluoromethyl)phenyl], $R_4$ is (5-bromo-2-pyridyl) and $Z_1$ is as defined in table Z.

Table A-43 provides 45 compounds A-43.001 to A-43.045 of formula Iaa wherein $R_1$ is $CH_3$, $R_2$ is [3-(trifluoromethoxy)-5-(trifluoromethyl)phenyl], $R_4$ is pyrimidin-2-yl and $Z_1$ is as defined in table Z.

Table A-44 provides 45 compounds A-44.001 to A-44.045 of formula Iaa wherein $R_1$ is $CH_3$, $R_2$ is [3-(trifluoromethoxy)-5-(trifluoromethyl)phenyl], $R_4$ is (5-bromopyrimidin-2-yl) and $Z_1$ is as defined in table Z.

Table A-45 provides 45 compounds A-45.001 to A-45.045 of formula Iaa wherein $R_1$ is $CH_3$, $R_2$ is [3-bromo-5-(trifluoromethyl)phenyl], $R_4$ is 2-pyridyl and $Z_1$ is as defined in table Z.

Table A-46 provides 45 compounds A-46.001 to A-46.045 of formula Iaa wherein $R_1$ is $CH_3$, $R_2$ is [3-bromo-5-(trifluoromethyl)phenyl], $R_4$ is (5-bromo-2-pyridyl) and $Z_1$ is as defined in table Z.

Table A-47 provides 45 compounds A-47.001 to A-47.045 of formula Iaa wherein $R_1$ is $CH_3$, $R_2$ is [3-bromo-5-(trifluoromethyl)phenyl], $R_4$ is pyrimidin-2-yl and $Z_1$ is as defined in table Z.

Table A-48 provides 45 compounds A-48.001 to A-48.045 of formula Iaa wherein $R_1$ is $CH_3$, $R_2$ is [3-bromo-5-(trifluoromethyl)phenyl], $R_4$ is (5-bromopyrimidin-2-yl) and $Z_1$ is as defined in table Z.

Table A-49 provides 45 compounds A-49.001 to A-49.045 of formula Iaa wherein $R_1$ is $CH_3$, $R_2$ is [3-(trifluoromethyl)-5-(trifluoromethylsulfanyl)phenyl], $R_4$ is 2-pyridyl and $Z_1$ is as defined in table Z.

Table A-50 provides 45 compounds A-50.001 to A-50.045 of formula Iaa wherein $R_1$ is $CH_3$, $R_2$ is [3-(trifluoromethyl)-5-(trifluoromethylsulfanyl)phenyl], $R_4$ is (5-bromo-2-pyridyl) and $Z_1$ is as defined in table Z.

Table A-51 provides 45 compounds A-51.001 to A-51.045 of formula Iaa wherein $R_1$ is $CH_3$, $R_2$ is [3-(trifluoromethyl)-5-(trifluoromethylsulfanyl)phenyl], $R_4$ is pyrimidin-2-yl and $Z_1$ is as defined in table Z.

Table A-52 provides 45 compounds A-52.001 to A-52.045 of formula Iaa wherein $R_1$ is $CH_3$, $R_2$ is [3-(trifluoromethyl)-5-(trifluoromethylsulfanyl)phenyl], $R_4$ is (5-bromopyrimidin-2-yl) and $Z_1$ is as defined in table Z.

Table A-53 provides 45 compounds A-53.001 to A-53.045 of formula Iaa wherein $R_1$ is $CH_3$, $R_2$ is [3-(difluoromethoxy)-5-(trifluoromethyl)phenyl], $R_4$ is 2-pyridyl and $Z_1$ is as defined in table Z.

Table A-54 provides 45 compounds A-54.001 to A-54.045 of formula Iaa wherein $R_1$ is $CH_3$, $R_2$ is [3-(difluoromethoxy)-5-(trifluoromethyl)phenyl], $R_4$ is (5-bromo-2-pyridyl) and $Z_1$ is as defined in table Z.

Table A-55 provides 45 compounds A-55.001 to A-55.045 of formula Iaa wherein $R_1$ is $CH_3$, $R_2$ is [3-(difluoromethoxy)-5-(trifluoromethyl)phenyl], $R_4$ is pyrimidin-2-yl and $Z_1$ is as defined in table Z.

Table A-56 provides 45 compounds A-56.001 to A-56.045 of formula Iaa wherein $R_1$ is $CH_3$, $R_2$ is [3-(difluoromethoxy)-5-(trifluoromethyl)phenyl], $R_4$ is (5-bromopyrimidin-2-yl) and $Z_1$ is as defined in table Z.

Table A-57 provides 45 compounds A-57.001 to A-57.045 of formula Iaa wherein $R_1$ is cylopropylmethyl, $R_2$ is [3,5-bis(trifluoromethyl)phenyl], $R_4$ is 2-pyridyl and $Z_1$ is as defined in table Z.

Table A-58 provides 45 compounds A-58.001 to A-58.045 of formula Iaa wherein $R_1$ is cylopropylmethyl, $R_2$ is [3,5-bis(trifluoromethyl)phenyl], $R_4$ is (5-bromo-2-pyridyl) and $Z_1$ is as defined in table Z.

Table A-59 provides 45 compounds A-59.001 to A-59.045 of formula Iaa wherein $R_1$ is cylopropylmethyl, $R_2$ is [3,5-bis(trifluoromethyl)phenyl], $R_4$ is pyrimidin-2-yl and $Z_1$ is as defined in table Z.

Table A-60 provides 45 compounds A-60.001 to A-60.045 of formula Iaa wherein $R_1$ is cylopropylmethyl, $R_2$ is [3,5-bis(trifluoromethyl)phenyl], $R_4$ is (5-bromopyrimidin-2-yl) and $Z_1$ is as defined in table Z.

Table A-61 provides 45 compounds A-61.001 to A-61.045 of formula Iaa wherein $R_1$ is cylopropylmethyl, $R_2$ is [3-chloro-5-(trifluoromethyl)phenyl], $R_4$ is 2-pyridyl and $Z_1$ is as defined in table Z.

Table A-62 provides 45 compounds A-62.001 to A-62.045 of formula Iaa wherein $R_1$ is cylopropylmethyl, $R_2$ is [3-chloro-5-(trifluoromethyl)phenyl], $R_4$ is (5-bromo-2-pyridyl) and $Z_1$ is as defined in table Z.

Table A-63 provides 45 compounds A-63.001 to A-63.045 of formula Iaa wherein $R_1$ is cylopropylmethyl, $R_2$ is [3-chloro-5-(trifluoromethyl)phenyl], $R_4$ is pyrimidin-2-yl and $Z_1$ is as defined in table Z.

Table A-64 provides 45 compounds A-64.001 to A-64.045 of formula Iaa wherein $R_1$ is cylopropylmethyl, $R_2$ is [3-chloro-5-(trifluoromethyl)phenyl], $R_4$ is (5-bromopyrimidin-2-yl) and $Z_1$ is as defined in table Z.

Table A-65 provides 45 compounds A-65.001 to A-65.045 of formula Iaa wherein $R_1$ is cylopropylmethyl, $R_2$ is [3-chloro-5-(trifluoromethoxy)phenyl], $R_4$ is 2-pyridyl and $Z_1$ is as defined in table Z.

Table A-66 provides 45 compounds A-66.001 to A-66.045 of formula Iaa wherein $R_1$ is cylopropylmethyl, $R_2$ is [3-chloro-5-(trifluoromethoxy)phenyl], $R_4$ is (5-bromo-2-pyridyl) and $Z_1$ is as defined in table Z.

Table A-67 provides 45 compounds A-67.001 to A-67.045 of formula Iaa wherein $R_1$ is cylopropylmethyl, $R_2$ is [3-chloro-5-(trifluoromethoxy)phenyl], $R_4$ is pyrimidin-2-yl and $Z_1$ is as defined in table Z.

Table A-68 provides 45 compounds A-68.001 to A-68.045 of formula Iaa wherein $R_1$ is cylopropylmethyl, $R_2$ is [3-chloro-5-(trifluoromethoxy)phenyl], $R_4$ is (5-bromopyrimidin-2-yl) and $Z_1$ is as defined in table Z.

Table A-69 provides 45 compounds A-69.001 to A-69.045 of formula Iaa wherein $R_1$ is cylopropylmethyl, $R_2$ is [3-(trifluoromethoxy)-5-(trifluoromethyl)phenyl], $R_4$ is 2-pyridyl and $Z_1$ is as defined in table Z.

Table A-70 provides 45 compounds A-70.001 to A-70.045 of formula Iaa wherein $R_1$ is cylopropylmethyl, $R_2$ is [3-(trifluoromethoxy)-5-(trifluoromethyl)phenyl], $R_4$ is (5-bromo-2-pyridyl) and $Z_1$ is as defined in table Z.

Table A-71 provides 45 compounds A-71.001 to A-71.045 of formula Iaa wherein $R_1$ is cylopropylmethyl, $R_2$ is [3-(trifluoromethoxy)-5-(trifluoromethyl)phenyl], $R_1$ is pyrimidin-2-yl and $Z_1$ is as defined in table Z.

Table A-72 provides 45 compounds A-72.001 to A-72.045 of formula Iaa wherein $R_1$ is cylopropylmethyl, $R_2$ is [3-(trifluoromethoxy)-5-(trifluoromethyl)phenyl], $R_4$ is (5-bromopyrimidin-2-yl) and $Z_1$ is as defined in table Z.

Table A-73 provides 45 compounds A-73.001 to A-73.045 of formula Iaa wherein $R_1$ is cylopropylmethyl, $R_2$ is [3-bromo-5-(trifluoromethyl)phenyl], $R_4$ is 2-pyridyl and $Z_1$ is as defined in table Z.

Table A-74 provides 45 compounds A-74.001 to A-74.045 of formula Iaa wherein $R_1$ is cylopropylmethyl, $R_2$ is [3-bromo-5-(trifluoromethyl)phenyl], $R_4$ is (5-bromo-2-pyridyl) and $Z_1$ is as defined in table Z.

Table A-75 provides 45 compounds A-75.001 to A-75.045 of formula Iaa wherein $R_1$ is cylopropylmethyl, $R_2$ is [3-bromo-5-(trifluoromethyl)phenyl], $R_4$ is pyrimidin-2-yl and $Z_1$ is as defined in table Z.

Table A-76 provides 45 compounds A-76.001 to A-76.045 of formula Iaa wherein $R_1$ is cylopropylmethyl, $R_2$ is [3-bromo-5-(trifluoromethyl)phenyl], $R_4$ is (5-bromopyrimidin-2-yl) and $Z_1$ is as defined in table Z.

Table A-77 provides 45 compounds A-77.001 to A-77.045 of formula Iaa wherein R, is cylopropylmethyl, $R_2$ is [3-(trifluoromethyl)-5-(trifluoromethylsulfanyl)phenyl], $R_4$ is 2-pyridyl and $Z_1$ is as defined in table Z.

Table A-78 provides 45 compounds A-78.001 to A-78.045 of formula Iaa wherein $R_1$ is cylopropylmethyl, $R_2$ is [3-(trifluoromethyl)-5-(trifluoromethylsulfanyl)phenyl], $R_4$ is (5-bromo-2-pyridyl) and $Z_1$ is as defined in table Z.

Table A-79 provides 45 compounds A-79.001 to A-79.045 of formula Iaa wherein $R_1$ is cylopropylmethyl, $R_2$ is [3-(trifluoromethyl)-5-(trifluoromethylsulfanyl)phenyl], $R_4$ is pyrimidin-2-yl and $Z_1$ is as defined in table Z.

Table A-80 provides 45 compounds A-80.001 to A-80.045 of formula Iaa wherein $R_1$ is cylopropylmethyl, $R_2$ is [3-(trifluoromethyl)-5-(trifluoromethylsulfanyl)phenyl], $R_4$ is (5-bromopyrimidin-2-yl) and $Z_1$ is as defined in table Z.

Table A-81 provides 45 compounds A-81.001 to A-81.045 of formula Iaa wherein $R_1$ is cylopropylmethyl, $R_2$ is [3-(difluoromethoxy)-5-(trifluoromethyl)phenyl], $R_4$ is 2-pyridyl and $Z_1$ is as defined in table Z.

Table A-82 provides 45 compounds A-82.001 to A-82.045 of formula Iaa wherein $R_1$ is cylopropylmethyl, $R_2$ is [3-(difluoromethoxy)-5-(trifluoromethyl)phenyl], $R_4$ is (5-bromo-2-pyridyl) and $Z_1$ is as defined in table Z.

Table A-83 provides 45 compounds A-83.001 to A-83.045 of formula Iaa wherein $R_1$ is cylopropylmethyl, $R_2$ is [3-(difluoromethoxy)-5-(trifluoromethyl)phenyl], $R_4$ is pyrimidin-2-yl and $Z_1$ is as defined in table Z.

Table A-84 provides 45 compounds A-84.001 to A-84.045 of formula Iaa wherein $R_1$ is cylopropylmethyl, $R_2$ is [3-(difluoromethoxy)-5-(trifluoromethyl)phenyl], $R_4$ is (5-bromopyrimidin-2-yl) and $Z_1$ is as defined in table Z.

Table A-85 provides 45 compounds A-85.001 to A-85.045 of formula Iaa wherein $R_1$ is H, $R_2$ is [3-(2,2-difluoroethoxy)-5-(trifluoromethyl)phenyl], $R_4$ is 2-pyridyl and $Z_1$ is as defined in table Z.

Table A-86 provides 45 compounds A-86.001 to A-86.045 of formula Iaa wherein $R_1$ is H, $R_2$ is [3-(2,2-difluoroethoxy)-5-(trifluoromethyl)phenyl], $R_4$ is (5-bromo-2-pyridyl) and $Z_1$ is as defined in table Z.

Table A-87 provides 45 compounds A-87.001 to A-87.045 of formula Iaa wherein $R_1$ is H, $R_2$ is [3-(2,2-difluoroethoxy)-5-(trifluoromethyl)phenyl], $R_4$ is pyrimidin-2-yl and $Z_1$ is as defined in table Z.

Table A-88 provides 45 compounds A-88.001 to A-88.045 of formula Iaa wherein $R_1$ is H, $R_2$ is [3-(2,2-difluoroethoxy)-5-(trifluoromethyl)phenyl], $R_4$ is (5-bromopyrimidin-2-yl) and $Z_1$ is as defined in table Z.

Table A-89 provides 45 compounds A-89.001 to A-89.045 of formula Iaa wherein $R_1$ is H, $R_2$ is [3-(2,2,2-trifluoroethoxy)-5-(trifluoromethyl)phenyl], $R_4$ is 2-pyridyl and $Z_1$ is as defined in table Z.

Table A-90 provides 45 compounds A-90.001 to A-90.045 of formula Iaa wherein $R_1$ is H, $R_2$ is [3-(2,2,2-trifluoroethoxy)-5-(trifluoromethyl)phenyl], $R_4$ is (5-bromo-2-pyridyl) and $Z_1$ is as defined in table Z.

Table A-91 provides 45 compounds A-91.001 to A-91.045 of formula Iaa wherein $R_1$ is H, $R_2$ is [3-(2,2,2-trifluoroethoxy)-5-(trifluoromethyl)phenyl], $R_4$ is pyrimidin-2-yl and $Z_1$ is as defined in table Z.

Table A-92 provides 45 compounds A-92.001 to A-92.045 of formula Iaa wherein $R_1$ is H, $R_2$ is [3-(2,2,2-trifluoroethoxy)-5-(trifluoromethyl)phenyl], $R_4$ is (5-bromopyrimidin-2-yl) and $Z_1$ is as defined in table Z.

Also made available are certain intermediate compounds of the formula XV. The tables B-1 to B-21 below illustrate specific compounds of the formula XVaa.

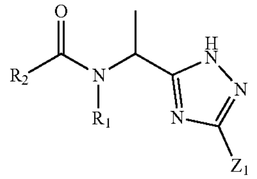

XVaa

Table B-1 provides 4 compounds B-1.001 to B-1.004 of formula XVaa wherein $R_1$ is H, $R_2$ is [3,5-bis(trifluoromethyl)phenyl] and $Z_1$ are as defined in table W.

TABLE W

| Substituent definitions of $Z_1$: | |
|---|---|
| Index | $Z_1$ |
| 1 | F |
| 2 | Cl |
| 3 | Br |
| 4 | I |

Table B-2 provides 4 compounds B-2.001 to B-2.004 of formula XVaa wherein $R_1$ is H, $R_2$ is [3-chloro-5-(trifluoromethyl)phenyl] and $Z_1$ are as defined in table W.

Table B-3 provides 4 compounds B-3.001 to B-3.004 of formula XVaa wherein $R_1$ is H, $R_2$ is [3-chloro-5-(trifluoromethoxy)phenyl] and $Z_1$ are as defined in table W.

Table B-4 provides 4 compounds B-4.001 to B-4.004 of formula XVaa wherein $R_1$ is H, $R_2$ is [3-(trifluoromethoxy)-5-(trifluoromethyl)phenyl] and $Z_1$ are as defined in table W.

Table B-5 provides 4 compounds B-5.001 to B-5.004 of formula XVaa wherein $R_1$ is H, $R_2$ is [3-bromo-5-(trifluoromethyl)phenyl] and $Z_1$ are as defined in table W.

Table B-6 provides 4 compounds B-6.001 to B-6.004 of formula XVaa wherein $R_1$ is H, $R_2$ is [3-(trifluoromethyl)-5-(trifluoromethylsulfanyl)phenyl] and $Z_1$ are as defined in table W.

Table B-7 provides 4 compounds B-7.001 to B-7.004 of formula XVaa wherein $R_1$ is H, $R_2$ is [3-(difluoromethoxy)-5-(trifluoromethyl)phenyl] and Z, are as defined in table W.

Table B-8 provides 4 compounds B-8.001 to B-8.004 of formula XVaa wherein $R_1$ is $CH_3$, $R_2$ is [3,5-bis(trifluoromethyl)phenyl] and $Z_1$ are as defined in table W.

Table B-9 provides 4 compounds B-9.001 to B-9.004 of formula XVaa wherein $R_1$ is $CH_3$, $R_2$ is [3-chloro-5-(trifluoromethyl)phenyl] and $Z_1$ are as defined in table W.

Table B-10 provides 4 compounds B-10.001 to B-10.004 of formula XVaa wherein $R_1$ is $CH_3$, $R_2$ is [3-chloro-5-(trifluoromethoxy)phenyl] and $Z_1$ are as defined in table W.

Table B-11 provides 4 compounds B-11.001 to B-11.004 of formula XVaa wherein $R_1$ is $CH_3$, $R_2$ is [3-(trifluoromethoxy)-5-(trifluoromethyl)phenyl] and $Z_1$ are as defined in table W.

Table B-12 provides 4 compounds B-12.001 to B-12.004 of formula XVaa wherein $R_1$ is $CH_3$, $R_2$ is [3-bromo-5-(trifluoromethyl)phenyl] and $Z_1$ are as defined in table W.

Table B-13 provides 4 compounds B-13.001 to B-13.004 of formula XVaa wherein $R_1$ is $CH_3$, $R_2$ is [3-(trifluoromethyl)-5-(trifluoromethylsulfanyl)phenyl] and $Z_1$ are as defined in table W.

Table B-14 provides 4 compounds B-14.001 to B-14.004 of formula XVaa wherein $R_1$ is $CH_3$, $R_2$ is [3-(difluoromethoxy)-5-(trifluoromethyl)phenyl] and $Z_1$ are as defined in table W.

Table B-15 provides 4 compounds B-15.001 to B-15.004 of formula XVaa wherein $R_1$ is cylopropylmethyl, $R_2$ is [3,5-bis(trifluoromethyl)phenyl] and $Z_1$ are as defined in table W.

Table B-16 provides 4 compounds B-16.001 to B-16.004 of formula XVaa wherein $R_1$ is cylopropylmethyl, $R_2$ is [3-chloro-5-(trifluoromethyl)phenyl] and $Z_1$ are as defined in table W.

Table B-17 provides 4 compounds B-17.001 to B-17.004 of formula XVaa wherein $R_1$ is cylopropylmethyl, $R_2$ is [3-chloro-5-(trifluoromethoxy)phenyl] and $Z_1$ are as defined in table W.

Table B-18 provides 4 compounds B-18.001 to B-18.004 of formula XVaa wherein $R_1$ is cylopropylmethyl, $R_2$ is [3-(trifluoromethoxy)-5-(trifluoromethyl)phenyl] and $Z_1$ are as defined in table W.

Table B-19 provides 4 compounds B-19.001 to B-19.004 of formula XVaa wherein $R_1$ is cylopropylmethyl, $R_2$ is [3-bromo-5-(trifluoromethyl)phenyl] and $Z_1$ are as defined in table W.

Table B-20 provides 4 compounds B-20.001 to B-20.004 of formula XVaa wherein $R_1$ is cylopropylmethyl, $R_2$ is [3-(trifluoromethyl)-5-(trifluoromethylsulfanyl)phenyl] and $Z_1$ are as defined in table W.

Table B-21 provides 4 compounds B-21.001 to B-21.004 of formula XVaa wherein $R_1$ is cylopropylmethyl, $R_2$ is [3-(difluoromethoxy)-5-(trifluoromethyl)phenyl] and $Z_1$ are as defined in table W.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order *Acarina*. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the above mentioned animal pests are:

from the order *Acarina*, for example,

*Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order *Anoplura*, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus,*

*Epilachna* spp., *Eremnus* spp., *Heteronychus arator, Hypothenemus hampei, Lagria vilosa, Leptinotarsa decemlineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., *Psylliodes* spp., *Rhyssomatus aubtilis, Rhizopertha* spp., *Scarabeidae, Sitophilus* spp., *Sitotroga* spp., *Somaticus* spp, *Sphenophorus* spp, *Sternechus subsignatus, Tenebrio* spp., *Tribolium* spp. and *Trogoderma* spp.;

from the order Diptera, for example,

*Aedes* spp., *Anopheles* spp, *Antherigona soccata, Bactrocea oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example,

*Acanthocoris scabrator, Acrosternum* spp, *Adelphocoris lineolatus, Aleurodes* spp., *Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euchistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotinophara* spp., *Thyanta* spp, *Triatoma* spp., *Vatiga illudens; Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii Scop., Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri Mats, Odonaspis ruthae, Oregma lanigera Zehnter, Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order *Hymenoptera*, for example,

*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order *Isoptera*, for example,

*Coptotermes* spp, Corniternes *cumulans, Incisitermes* spp, *Macrotermes* spp, *Mastotermes* spp, *Microtermes* spp, *Reticulitermes* spp.; *Solenopsis* geminate from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Elasmopalpus lignosellus, Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta*, and *Yponomeuta* spp.;

from the order Mallophaga, for example,

*Damalinea* spp. and *Trichodectes* spp.;

from the order *Orthoptera*, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order *Siphonaptera*, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus* destructor, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; Arion (*A. ater, A. circumscriptus, A. hortensis, A. rufus*); *Bradybaenidae* (*Bradybaena fruticum*); *Cepaea* (*C. hortensis, C. Nemoralis*); *ochlodina; Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); *Helicidae Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubereux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (*carnation*), *Canna* spp., *Oxalis* spp., *Bellis* spp., *Pelargonium* spp. (*P. peltatum, P. Zonale*), *Viola* spp. (*pansy*), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (*rose*), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba.*

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Dia-*

*brotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

The compounds of formula I are particularly suitable for control of

- a pest of the order Hemiptera, for example, one or more of the species *Bemisia tabaci, Aphis craccivora, Myzus persicae, Rhopalosiphum Padi, Nilaparvata lugens*, and *Euschistus heros* (preferably in vegetables, soybeans, and sugarcane);
- a pest of the order Lepidoptera, for example, one or more of the species *Spodoptera littoralis, Spodoptera frugiperda, Plutella xylostella, Cnaphalocrocis medinalis, Cydia pomonella, Chrysodeixis includes, Chilo suppressalis, Elasmopalpus lignosellus, Pseudoplusia includens*, and *Tuta absoluta* (preferably in vegetables and corn);
- a pest of the order Thysanoptera, such as the family Thripidae, for example, one or more of *Thrips tabaci* and *Frankliniella occidentalis* (preferably in vegetables); and
- soil pests (such as of the order Coleoptera), for example, the species *Diabrotica balteata, Agriotes* spp. and *Leptinotarsa decemlineata* (preferably in vegetables and corn).

The term “crops” is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as b-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by b-endotoxins, for example Cry1Ab, Cry1Ac, Cry1F, Cry1 Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003.

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention provides a compound of the first aspect for use in therapy. The present invention provides a compound of the first aspect, for use in controlling parasites in or on an animal. The present invention further provides a compound of the first aspect, for use in controlling ectoparasites on an animal. The present invention further provides a compound of the first aspect, for use in preventing and/or treating diseases transmitted by ectoparasites.

The present invention provides the use of a compound of the first aspect, for the manufacture of a medicament for controlling parasites in or on an animal. The present invention further provides the use of a compound of the first aspect, for the manufacture of a medicament for controlling ectoparasites on an animal. The present invention further provides the use of a compound of the first aspect, for the manufacture of a medicament for preventing and/or treating diseases transmitted by ectoparasites.

The present invention provides the use of a compound of the first aspect, in controlling parasites in or on an animal. The present invention further provides the use of a compound of the first aspect, in controlling ectoparasites on an animal.

The term "controlling" when used in context of parasites in or on an animal refers to reducing the number of pests or parasites, eliminating pests or parasites and/or preventing further pest or parasite infestation.

The term "treating" when used in context of parasites in or on an animal refers to restraining, slowing, stopping or reversing the progression or severity of an existing symptom or disease.

The term "preventing" when used in context of parasites in or on an animal refers to the avoidance of a symptom or disease developing in the animal.

The term "animal" when used in context of parasites in or on an animal may refer to a mammal and a non-mammal, such as a bird or fish. In the case of a mammal, it may be a human or non-human mammal. Non-human mammals include, but are not limited to, livestock animals and companion animals. Livestock animals include, but are not limited to, cattle, camellids, pigs, sheep, goats and horses. Companion animals include, but are not limited to, dogs, cats and rabbits.

A "parasite" is a pest which lives in or on the host animal and benefits by deriving nutrients at the host animal's expense. An "endoparasite" is a parasite which lives in the host animal. An "ectoparasite" is a parasite which lives on the host animal. Ectoparasites include, but are not limited to, *acari*, insects and crustaceans (e.g. sea lice). The *Acari* (or *Acarina*) sub-class comprises ticks and mites. Ticks include, but are not limited to, members of the following genera: *Rhipicaphalus*, for example, *Rhipicaphalus* (*Boophilus*) *microplus* and *Rhipicephalus sanguineus; Amblyomma; Dermacentor, Haemaphysalis; Hyalomma; Ixodes; Rhipicentor; Margaropus; Argas; Otobius*; and *Ornithodoros*. Mites include, but are not limited to, members of the following genera: *Chorioptes*, for example *Chorioptes*

*bovis; Psoroptes*, for example *Psoroptes ovis; Cheyletiella; Dermanyssus*; for example *Dermanyssus gallinae; Ortnithonyssus; Demodex*, for example *Demodex canis; Sarcoptes*, for example *Sarcoptes scabiei*; and *Psorergates*. Insects include, but are not limited to, members of the orders: *Siphonaptera*, Diptera, Phthiraptera, Lepidoptera, Coleoptera and Homoptera. Members of the *Siphonaptera* order include, but are not limited to, *Ctenocephalides felis* and *Ctenocephatides canis*. Members of the Diptera order include, but are not limited to, *Musca* spp.; bot fly, for example *Gasterophilus intestinalis* and *Oestrus ovis*; biting flies; horse flies, for example *Haematopota* spp. and *Tabunus* spp.; *haematobia*, for example *haematobia irritans; Stomoxys; Lucilia*; midges; and mosquitoes. Members of the Phthiraptera class include, but are not limited to, blood sucking lice and chewing lice, for example *Bovicola Ovis* and *Bovicola Bovis*.

The term "effective amount" when used used in context of parasites in or on an animal refers to the amount or dose of the compound of the invention, or a salt thereof, which, upon single or multiple dose administration to the animal, provides the desired effect in or on the animal. The effective amount can be readily determined by the attending diagnostician, as one skilled in the art, by the use of known techniques and by observing results obtained under analogous circumstances. In determining the effective amount a number of factors are considered by the attending diagnostician, including, but not limited to: the species of mammal; its size, age, and general health; the parasite to be controlled and the degree of infestation; the specific disease or disorder involved; the degree of or involvement or the severity of the disease or disorder; the response of the individual; the particular compound administered; the mode of administration; the bioavailability characteristics of the preparation administered; the dose regimen selected; the use of concomitant medication; and other relevant circumstances.

The compounds of the invention may be administered to the animal by any route which has the desired effect including, but not limited to topically, orally, parenterally and subcutaneously. Topical administration is preferred. Formulations suitable for topical administration include, for example, solutions, emulsions and suspensions and may take the form of a pour-on, spot-on, spray-on, spray race or dip. In the alternative, the compounds of the invention may be administered by means of an ear tag or collar.

Salt forms of the compounds of the invention include both pharmaceutically acceptable salts and veterinary acceptable salts, which can be different to agrochemically acceptable salts. Pharmaceutically and veterinary acceptable salts and common methodology for preparing them are well known in the art. See, for example, Gould, P. L., "Salt selection for basic drugs", International Journal of Pharmaceutics, 33: 201-217 (1986); Bastin, R. J., et al. "Salt Selection and Optimization Procedures for Pharmaceutical New Chemical Entities", Organic Process Research and Development, 4: 427-435 (2000); and Berge, S. M., et al., "Pharmaceutical Salts", Journal of Pharmaceutical Sciences, 66: 1-19, (1977). One skilled in the art of synthesis will appreciate that the compounds of the invention are readily converted to and may be isolated as a salt, such as a hydrochloride salt, using techniques and conditions well known to one of ordinary skill in the art. In addition, one skilled in the art of synthesis will appreciate that the compounds of the invention are readily converted to and may be isolated as the corresponding free base from the corresponding salt.

The present invention also provides a method for controlling pests (such as mosquitoes and other disease vectors. In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs, ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass *ataenius, A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana*, Blattelagermanica and *Supella* spp.

Of the subclass Acaria (Acarida) and the orders Meta- and Meso-*stigmata*, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*. The compounds of formulae I, and I'a, or salts thereof, are especially suitable for controlling one or more pests selected from the family: Noctuidae, Plutellidae, Chrysomelidae, Thripidae, Pentatomidae, Tortricidae, Delphacidae, Aphididae, Noctuidae, Crambidae, Meloidogynidae, and Heteroderidae. In a preferred embodiment of each aspect, a compound TX (where the abbreviation "TX" means "one compound selected from the compounds defined in the Tables A-1 to A-92 and Table P") controls one or more of pests selected from the family: Noctuidae, Plutellidae, Chrysomelidae, Thripidae, Pentatomidae, Tortricidae, Delphacidae, Aphididae, Noctuidae, Crambidae, Meloidogynidae, and Heteroderidae.

The compounds of formulae I, and I'a, or salts thereof, are especially suitable for controlling one or more of pests selected from the genus: *Spodoptera* spp, *Plutella* spp, *Frankliniella* spp, *Thrips* spp, *Euschistus* spp, *Cydia* spp, *Nilaparvata* spp, *Myzus* spp, *Aphis* spp, *Diabrotica* spp, *Rhopalosiphum* spp, *Pseudoplusia* spp and *Chilo* spp. In a preferred embodiment of each aspect, a compound TX (where the abbreviation "TX" means "one compound selected from the compounds defined in the Tables A-1 to A-92 and Table P") controls one or more of pests selected from the genus: *Spodoptera* spp, *Plutella* spp, *Frankliniella* spp, *Thrips* spp, *Euschistus* spp, *Cydia* spp, *Nilaparvata* spp,

*Myzus* spp, *Aphis* spp, *Diabrotica* spp, *Rhopalosiphum* spp, *Pseudoplusia* spp and *Chilo* spp.

The compounds of formulae I, and I'a, or salts thereof, are especially suitable for controlling one or more of *Spodoptera littoralis, Plutella xylostella, Frankliniella occidentalis, Thrips tabaci, Euschistus heros, Cydia pomonella, Nilaparvata lugens, Myzus persicae, Chrysodeixis includens, Aphis craccivora, Diabrotica balteata, Rhopalosiphum padi*, and *Chilo suppressalis.*

In a preferred embodiment of each aspect, a compound TX (where the abbreviation "TX" means "one compound selected from the compounds defined in the Tables A-1 to A-92 and Table P") controls one or more of *Spodoptera littoralis, Plutella xylostella, Frankliniella occidentalis, Thrips tabaci, Euschistus heros, Cydia pomonella, Nilaparvata lugens, Myzus persicae, Chrysodeixis includens, Aphis craccivora, Diabrotica balteata, Rhopalosiphum Padia*, and *Chilo Suppressalis*, such as *Spodoptera littoralis*+TX, *Plutella xylostella*+TX; *Frankliniella occidentalis*+TX, *Thrips tabaci*+TX, *Euschistus heros*+TX, *Cydia pomonella*+TX, *Nilaparvata lugens*+TX, *Myzus persicae*+TX, *Chrysodeixis includens*+TX, *Aphis craccivora*+TX, *Diabrotica balteata*+TX, *Rhopalosiphum Padi*+TX, and *Chilo suppressalis*+TX.

In an embodiment, of each aspect, one compound selected from the compounds defined in the Tables A-1 to A-92 and Table P, is suitable for controlling *Spodoptera littoralis, Plutella xylostella, Frankliniella occidentalis, Thrips tabaci, Euschistus heros, Cydia pomonella, Nilaparvata lugens, Myzus persicae, Chrysodeixis includens, Aphis craccivora, Diabrotica balteata, Rhopalosiphum Padia*, and *Chilo Suppressalis* in cotton, vegetable, maize, cereal, rice and soya crops.

In an embodiment, one compound from selected from the compounds defined in the Tables A-1 to A-92 and Table P, is suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo* supressalis (preferably in rice).

Compounds according to the invention may possess any number of benefits including, inter alia, advantageous levels of biological activity for protecting plants against insects or superior properties for use as agrochemical active ingredients (for example, greater biological activity, an advantageous spectrum of activity, an increased safety profile (against non-target organisms above and below ground (such as fish, birds and bees), improved physico-chemical properties, or increased biodegradability). In particular, it has been surprisingly found that certain compounds of formula I may show an advantageous safety profile with respect to non-target arthropods, in particular pollinators such as honey bees, solitary bees, and bumble bees. Most particularly, *Apis mellifera.*

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood New Jersey (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
- active ingredient: 1 to 95%, preferably 60 to 90%
- surface-active agent: 1 to 30%, preferably 5 to 20%
- liquid carrier: 1 to 80%, preferably 1 to 35%

Dusts:
- active ingredient: 0.1 to 10%, preferably 0.1 to 5%
- solid carrier: 99.9 to 90%, preferably 99.9 to 99%

Suspension Concentrates:
- active ingredient: 5 to 75%, preferably 10 to 50%
- water: 94 to 24%, preferably 88 to 30%
- surface-active agent: 1 to 40%, preferably 2 to 30%

Wettable Powders:
- active ingredient: 0.5 to 90%, preferably 1 to 80%
- surface-active agent: 0.5 to 20%, preferably 1 to 15%
- solid carrier: 5 to 95%, preferably 15 to 90%

Granules:
- active ingredient: 0.1 to 30%, preferably 0.1 to 15%
- solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalene-sulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | | 20% |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1H$ NMR measurements were recorded on a Brucker 400 MHz spectrometer, chemical shifts are given in ppm relevant to a TMS standard. Spectra measured in deuterated solvents as indicated. The method below was used to characterize the compounds. The characteristic LCMS values obtained for each compound were the retention time ("Rt", recorded in minutes) and the measured molecular ion $(M+H)^+$.

LCMS Method:

Spectra were recorded on a Mass Spectrometer from Waters (SQD, SQDII Single quadrupole mass spectrometer) equipped with an electrospray source (Polarity: positive and negative ions, Capillary: 3.00 kV, Cone range: 30 V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (ml/min) 0.85

Example 1: Preparation of N-[1-(5-bromo-2-pyrimidin-2-yl-1,2,4-triazol-3-yl)ethyl]-N-methyl-3,5-bis(trifluoromethyl)benzamide (compound P3)

P3

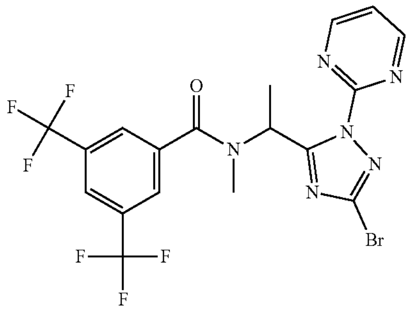

Step A: Preparation of 2-(methylamino)propanamide

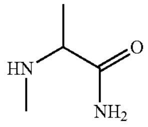

To a solution of 2-bromopropanamide (10 g, 65.8 mmol) in acetonitrile was added potassium carbonate (27.5 g, 197.4 mmol) and a 2 M solution of methylamine in THF (66 mL, 131.6 mmol). The resulting suspension is stirred at 80° C. for 16 hours, filtered and concentrated in vacuo. The residue was dissolved in ethyl acetate (100 mL), washed successively with water and brine, dried over sodium sulfate, filtered and concentrated in vacuo to give 2-(methylamino) propanamide as white crystals.

$^1$H-NMR (400 MHz, $CDCl_3$): δ=3.06 (q, J=7.0 Hz, 1H), 2.42 (s, 3H), 1.32 (d, J=7.0 Hz, 3H) ppm.

Step B: Preparation of N-(2-amino-1-methyl-2-oxo-ethyl)-N-methyl-3,5-bis(trifluoromethyl)benzamide

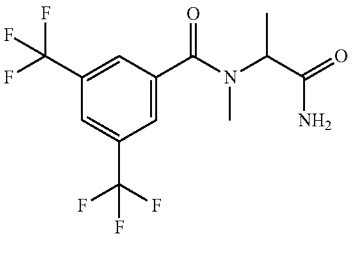 [SMILES: CC(C(N)=O)N(C)C(=O)c1cc(C(F)(F)F)cc(C(F)(F)F)c1]

A solution of 2-(methylamino)propanamide (6.7 g, 65.8 mmol), N,N-diisopropylethylamine (34.5 mL, 197 mmol), 3,5-bis(trifluoromethyl)benzoic acid (17 g, 65.8 mmol) in ethyl acetate (230 mL) and N,N-dimethylformamide (164 mL) was cooled at 0° C. and treated dropwise with a 50% solution of 2,4,6-tripropyl-1,3,5,2,4,6-trioxatriphosphorinane-2,4,6-trioxide (T3P) in ethyl acetate (47 mL, 79 mmol). The resulting orange solution was stirred at room temperature for 45 minutes and then concentrated in vacuo. The residue was dissolved in methyl tert-butyl ether (200 mL), and washed with water (2×30 mL), 2 M NaOH (2×30 mL), brine (30 mL), and the organic phase dried over sodium sulfate, filtered and concentrated in vacuo to give N-(2-amino-1-methyl-2-oxo-ethyl)-N-methyl-3,5-bis(trifluoromethyl)benzamide as a crude orange gum, which was used without any further purification in the following step.

$^1$H-NMR (400 MHz, $CDCl_3$): δ=7.98 (s, 1H), 7.92 (s, 2H), 5.25-5.15 (m, 1H), 2.95 (bs, 3H), 1.50 (d, J=7.0 Hz, 3H) ppm; LCMS: $R_t$ 0.85, m/z=341 (M−H$^+$, negative mode).

Step C: Preparation of N-[2-[dimethylaminomethyleneamino]-1-methyl-2-oxo-ethyl]-N-methyl-3,5-bis(trifluoromethyl)benzamide

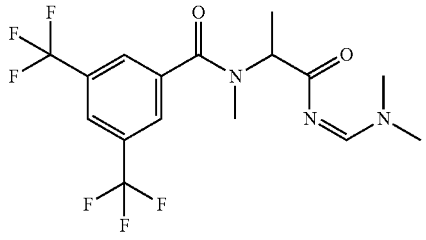 [SMILES: CC(C(=O)/N=C\N(C)C)N(C)C(=O)c1cc(C(F)(F)F)cc(C(F)(F)F)c1]

To a solution of N-(2-amino-1-methyl-2-oxo-ethyl)-N-methyl-3,5-bis(trifluoromethyl)benzamide (19 g, 55.52 mmol) in dichloromethane (285 mL) was added N,N-dimethylformamid dimethyl acetal (11 mL, 83 mmol). The resulting mixture was stirred at 40° C. for four hours and then concentrated in vacuo to give N-[2-[dimethylaminomethyleneamino]-1-methyl-2-oxo-ethyl]-N-methyl-3,5-bis(trifluoromethyl)benzamide as a crude orange gum.

LCMS: $R_t$ 0.89, m/z=398 (M+H$^+$).

Step D: Preparation of N-methyl-N-[1-(1H-1,2,4-triazol-5-yl)ethyl]-3,5-bis(trifluoromethyl)benzamide

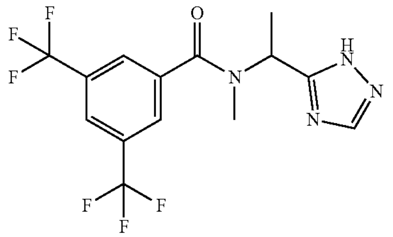 [SMILES: CC(c1ncn[nH]1)N(C)C(=O)c1cc(C(F)(F)F)cc(C(F)(F)F)c1]

To a solution of N-[2-[dimethylaminomethyleneamino]-1-methyl-2-oxo-ethyl]-N-methyl-3,5-bis(trifluoromethyl) benzamide (2 g, 4.78 mmol) in a mixture of 1,4-dioxane (20 mL) and acetic acid (20 mL) was added hydrazine monohydrate (0.465 mL, 9.56 mmol). The reaction mixture was stirred at 65° C. for two hours and then concentrated in vacuo. Purification by chromatography on silica gel (eluting with ethyl acetate in cyclohexane) afforded N-methyl-N-[1-(1H-1,2,4-triazol-5-yl)ethyl]-3,5-bis(trifluoromethyl)benzamide.

LCMS: $R_t$ 0.86, m/z=367 (M+H$^+$).

Step E: Preparation of N-[1-(3-bromo-1H-1,2,4-triazol-5-yl)ethyl]-N-methyl-3,5-bis(trifluoromethyl)benzamide (16)

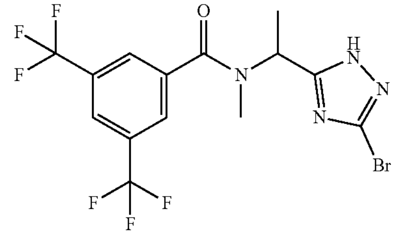 [SMILES: CC(c1nc(Br)n[nH]1)N(C)C(=O)c1cc(C(F)(F)F)cc(C(F)(F)F)c1]

To a solution of N-methyl-N-[1-(1H-1,2,4-triazol-5-yl)ethyl]-3,5-bis(trifluoromethyl)benzamide (0.95 g, 2.6 mmol) in dichloromethane (30 mL) was added a 2 M aqueous solution of NaOH (3.9 mL, 7.8 mmol) and a solution of benzyltrimethylammonium tribromide (1.1 g, 2.9 mmol) in dichloromethane (10 mL). The reaction mixture was stirred for 45 minutes and then carefully quenched with a 2 M aqueous solution of HCl. The organic phase was separated, dried over sodium sulfate, filtered and concentrated in vacuo to give N-[1-(3-bromo-1H-1,2,4-triazol-5-yl)ethyl]-N-methyl-3,5-bis(trifluoromethyl)benzamide as a yellow solid.

LCMS: $R_t$ 0.98, m/z=445, 447 (M+H$^+$).

Step F: Preparation of N-[1-(5-bromo-2-pyrimidin-2-yl-1,2,4-triazol-3-yl)ethyl]-N-methyl-3,5-bis(trifluoromethyl)benzamide compound P3)

P3

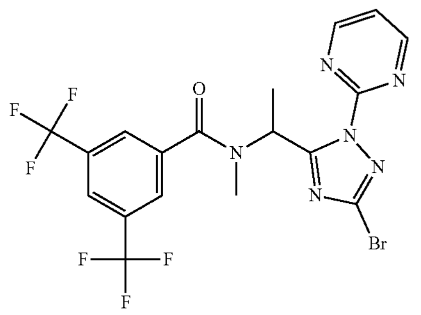

To a solution of N-[1-(3-bromo-1H-1,2,4-triazol-5-yl)ethyl]-N-methyl-3,5-bis(trifluoromethyl)benzamide (0.84 g, 1.9 mmol) in dry DMF (9.4 mL) was added NaH (0.11 g, 2.8 mmol) under argon followed by stirring at room temperature for 30 min. A solution of 2-bromopyrimidine (0.60 g, 3.8 mmol) in dry DMF (2.0 mL) was added to this mixture and the reaction was stirred at room temperature for 1 hour followed by heating to 120° C. for 15 hours. The reaction mixture was taken up in ethyl acetate and washed with water (5×5 mL), once with brine, dried over anhydrous MgSO4, filtered and concentrated in vacuo. Purification by reverse phase chromatography (eluting with acetonitrile/water) afforded N-[1-(5-bromo-2-pyrimidin-2-yl-1,2,4-triazol-3-yl)ethyl]-N-methyl-3,5-bis(trifluoromethyl)benzamide.

LCMS: $R_t$ 1.05, m/z=525 (M+H$^+$).

Example 2: Preparation of N-[1-[5-(methoxymethyl)-2-pyrimidin-2-yl-1,2,4-triazol-3-yl]ethyl]-3,5-bis(trifluoromethyl)benzamide (Compound P2)

P2

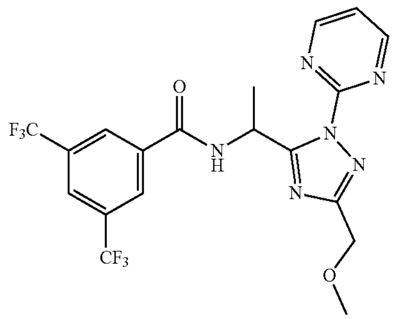

Step A: Preparation of ethyl 2-[[3,5-bis(trifluoromethyl)benzoyl]amino]propanoate

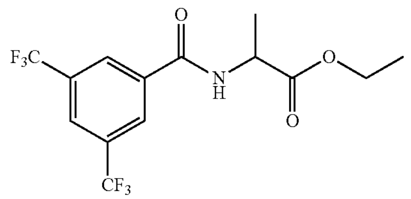 [SMILES: CCOC(=O)C(C)NC(=O)c1cc(C(F)(F)F)cc(C(F)(F)F)c1]

To a stirred solution of 3,5-bis(trifluoromethyl)benzoic acid (10.0 g, 38.7 mmol) in dichloromethane 10.0 mL) was added $SOCl_2$ (9.21 g, 77.5 mmol) at 0° C. and the resulting mixture stirred at room temperature for 2 hours. The mixture was then concentrated in vacuo and the residue obtained was added to a stirred solution of ethyl alaninate (5.44 g, 46.5 mmol) in pyridine (100 mL) at 0° C. The reaction mixture was stirred for 2 hours at room temperature. After reaction completion, the mixture was diluted with water, and extracted with ethyl acetate (10 ml×2). The combined organic phases were washed successively with 2 N HCl and brine, dried over $Na_2SO_4$ and concentrated in vacuo. The crude product was purified by chromatography over silica gel (eluting with ethyl acetate in cyclohexane) to afford ethyl 2-[[3,5-bis(trifluoromethyl)benzoyl]amino]propanoate.

LCMS: $R_t$ 1.06, m/z=358 (M+H$^+$).

Step B: Preparation of 2-[[3,5-bis(trifluoromethyl) benzoyl]amino]propanoic acid

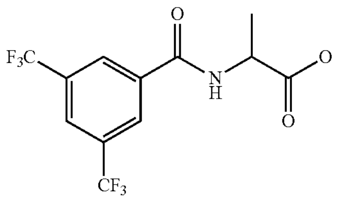 [SMILES: CC(NC(=O)c1cc(C(F)(F)F)cc(C(F)(F)F)c1)C(=O)O]

To a stirred solution of ethyl 2-[[3,5-bis(trifluoromethyl) benzoyl]amino]propanoate (5.00 g, 14.0 mmol) in THF:$H_2O$ (1:1, 50 mL) was added LiOH·$H_2O$ (1.76 g, 42.0 mmol) at 0° C. and the resulting mixture stirred for 2 hours at room temperature. The mixture was concentrated in vacuo, and the residue obtained acidified with 1N HCl to pH 1. The solid formed was collected by filtration and dried under reduced pressure to afford 2-[[3,5-bis(trifluoromethyl)benzoyl]amino]propanoic acid.

LCMS: $R_t$ 0.91, m/z=330 (M+H$^+$).

Step C: Preparation of N-[1-[5-(methoxymethyl)-2-pyrimidin-2-yl-1,2,4-triazol-3-yl]ethyl]-3,5-bis(trifluoromethyl)benzamide (Compound P2)

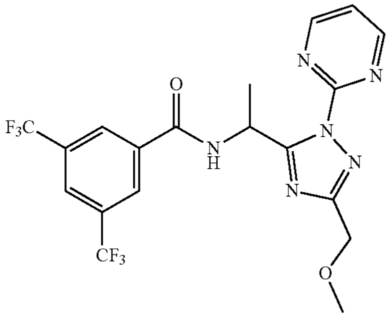 [SMILES: COCc1nc(C(C)NC(=O)c2cc(C(F)(F)F)cc(C(F)(F)F)c2)n(-c2ncccn2)n1]

To a stirred solution of 2-[[3,5-bis(trifluoromethyl)benzoyl]amino]propanoic acid (90.0%, 200 mg, 0.547 mmol) in DMF (4.0 mL) were added 2-methoxyacetamidine (48.2 mg. 0.547 mmol), HATU (312 mg, 0.820 mmol) and DIPEA (176 mg, 1.37 mmol) at room temperature. The resulting mixture was stirred at room temperature for 3 hours and then pyrimidin-2-ylhydrazine (72.3 mg, 0.656 mmol) and AcOH (249 mg, 4.16 mmol) were added at room temperature. The reaction mixture was stirred at 80° C. for 1 hour and then cooled down at room temperature. Ethyl acetate (25 mL) was added and the organic layer was washed with bicarbonate sat sol, and then water. Drying over $Na_2SO_4$ and concentration in vacuo gave the crude product which was purified by chromatography over silica gel (eluting with ethyl acetate in cyclohexane) to afford N-[1-[5-(methoxymethyl)-2-pyrimidin-2-yl-1,2,4-triazol-3-yl]ethyl]-3,5-bis(trifluoromethyl)benzamide (Compound P2).

LCMS: $R_t$ 0.92, m/z=475 (M+H$^+$); Mp: 155-160° C.; $^1$H NMR (400 MHz, $CDCl_3$): δ 8.92 (d, J=4.0 Hz 2H), 8.29 (s, 2H), 8.01 (s, 1H), 7.67 (d, J=8.0 Hz, 1H), 7.41 (t, J=4.0 Hz, 1H), 6.52 (t, J=7.4 Hz, 1H), 4.64 (s, 2H), 3.49 (s, 3H), 1.74 (d, J=8.0 Hz, 3H) ppm.

Example 3: Preparation of N-methyl-N-[1-(5-phenyl-2-pyrimidin-2-yl-1,2,4-triazol-3-yl)ethyl]-3,5-bis (trifluoromethyl)benzamide (compound P6)

P6

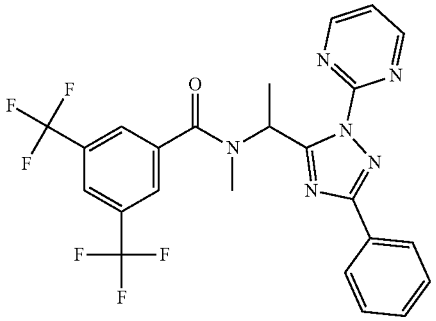

To a stirred solution of N-[1-(5-bromo-2-pyrimidin-2-yl-1,2,4-triazol-3-yl)ethyl]-N-methyl-3,5-bis(trifluoromethyl) benzamide (60 mg, 0.11 mmol) in dioxane (1.1 mL) were added phenylboronic acid (29 mg. 0.23 mmol), $Pd(PPh_3)_4$ (13 mg, 0.011 mmol) and an aqueous solution of potassium carbonate (2M, 0.17 mmol). The resulting mixture was stirred at reflux for 1 hour. After that time, LCMS indicated complete conversion, Isolute® was added into the reaction mixture, and the solvent removed by concentration in vacuo. The crude product was purified by chromatography over silica gel (eluting with ethyl acetate in cyclohexane) to afford N-methyl-N-[1-(5-phenyl-2-pyrimidin-2-yl-1,2,4-triazol-3-yl)ethyl]-3,5-bis(trifluoromethyl)benzamide (compound P6).

LCMS: $R_t$ 1.15, m/z=521 (M+H$^+$); $^1$H-NMR (400 MHz, $CDCl_3$): δ=8.9 (d, J=4.77 Hz, 2H) 8.3 (dd, J=7.52, 2.02 Hz, 2H) 7.9 (s, 1H) 7.7 (s, 2H) 7.4-7.5 (m, 3H) 7.4 (br t, J=4.58 Hz, 1H) 6.8 (q, J=6.72 Hz, 1H) 2.9 (s, 3H) 1.9 (br d, J=6.97 Hz, 3H) ppm.

Example 4: Preparation N-[1-(5-chloro-2-pyrimidin-2-yl-1,2,4-triazol-3-yl)ethyl]-N-methyl-3,5-bis(trifluoromethyl)benzamide (Compound P15)

P15

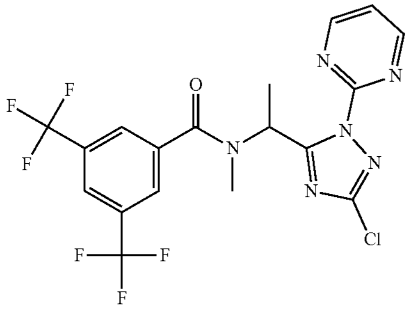

Step A: Preparation of N-[1-[5-(benzhydrylideneamino)-2-pyrimidin-2-yl-1,2,4-triazol-3-yl]ethyl]-N-methyl-3,5-bis(trifluoromethyl)benzamide (Compound P22)

P22

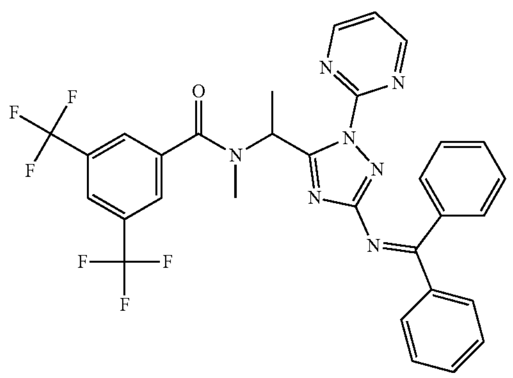

To a stirred solution of N-[1-(3-bromo-1H-1,2,4-triazol-5-yl)ethyl]-N-methyl-3,5-bis(trifluoromethyl)benzamide (P1) (100 mg, 0.19 mmol) in toluene (1.9 mL) were added benzophenone imine (71 mg. 0.38 mmol), xantphos (23 mg, 0.038 mmol), $Pd_2(dba)_3(PPh_3)_4$ (18 mg, 0.019 mmol) and cesium carbonate (19 mg, 0.57 mmol). The resulting mixture was stirred at reflux for 18 hours. After that time, LCMS indicated complete conversion, Isolute® was added into the reaction mixture, and the solvent removed in vacuo. The crude product was purified by chromatography over silica gel (eluting with ethyl acetate in cyclohexane) to afford N-[1-[5-(benzhydrylideneamino)-2-pyrimidin-2-yl-1,2,4-triazol-3-yl]ethyl]-N-methyl-3,5-bis(trifluoromethyl)benzamide (compound P22) as a gum.

LCMS: $R_t$ 1.19, m/z=624 ($M+H^+$).

Step B: Preparation of N-[1-(5-amino-2-pyrimidin-2-yl-1,2,4-triazol-3-yl)ethyl]-N-methyl-3,5-bis(trifluoromethyl)benzamide (Compound P7)

P7

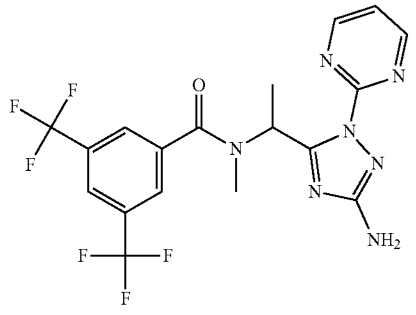

To a stirred solution of N-[1-[5-(benzhydrylideneamino)-2-pyrimidin-2-yl-1,2,4-triazol-3-yl]ethyl]-N-methyl-3,5-bis(trifluoromethyl)benzamide in THF (1.4 mL) was added a aqueous solution of HCl (2N, 0.20 mL, 0.41 mmol) and the resulting mixture was stirred at room temperature for 1 hour. Ethyl acetate (20 mL) was added and the organic layer was washed with bicarbonate sat sol, and then water. Drying over $Na_2SO_4$ and concentration in vacuo gave the crude product which was purified by chromatography over silica gel (eluting with ethylacetate/hexane) to afford N-[1-(5-amino-2-pyrimidin-2-yl-1,2,4-triazol-3-yl)ethyl]-N-methyl-3,5-bis(trifluoromethyl)benzamide (compound P7) as a brownish solid.

LCMS: $R_t$ 0.88, m/z=460 ($M+H^+$); $^1H$-NMR (400 MHz, $CDCl_3$): δ=8.76 (br d, J=4.8 Hz, 2H), 7.91 (br s, 1H), 7.69 (s, 2H), 7.2-7.3 (m, 1H), 6.7-6.8 (m, 1H), 4.38 (s, 2H) 2.87 (s, 3H), 1.73 (br d, J=7.0 Hz, 3H) ppm Step C: Preparation of N-[1-(5-chloro-2-pyrimidin-2-yl-1,2,4-triazol-3-yl)ethyl]-N-methyl-3,5-bis(trifluoromethyl)benzamide (P15)

P15

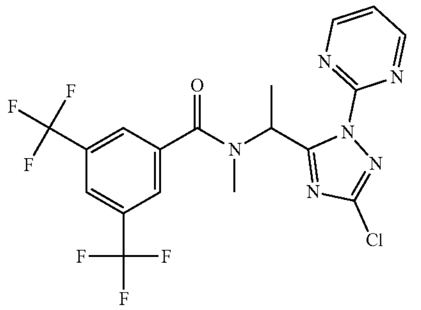

To a cooled suspension of N-[1-(5-amino-2-pyrimidin-2-yl-1,2,4-triazol-3-yl)ethyl]-N-methyl-3,5-bis(trifluoromethyl)benzamide (100 mg, 0.22 mmol) and $CuCl_2 \cdot 2H_2O$ (45 mg, 0.26 mmol) in concentrated HCl (1.0 mL) was added dropwise a solution of sodium nitrite (23 mg, 0.33 mmol) in 0.5 mL water. The reaction was stirred at room temperature for 12 h. Water was added, and the precipitate that formed was filtered off. It was purified by chromatography over silica gel (eluting with ethyl acetate/hexane) to afford N-[1-(5-chloro-2-pyrimidin-2-yl-1,2,4-triazol-3-yl)ethyl]-N-methyl-3,5-bis(trifluoromethyl)benzamide (Compound P15).

LCMS: $R_t$ 1.05, m/z=479 ($M+H^+$); $^1H$-NMR (400 MHz, $CDCl_3$): δ=8.86 (br d, J=4.4 Hz, 2H), 7.92 (br s, 1H), 7.69 (s, 2H), 7.40 (t, J=4.8 Hz, 1H), 6.72 (q, J=6.6 Hz, 1H), 2.93 (s, 3H), 1.79 (br d, J=7.0 Hz, 3H) ppm Example 5: Preparation of N-[1-[5-(1,2,4-oxadiazol-5-yl)-2-pyrimidin-2-yl-1,2,4-triazol-3-yl]ethyl]-3,5-bis(trifluoromethyl)benzamide (compound P1)

P1

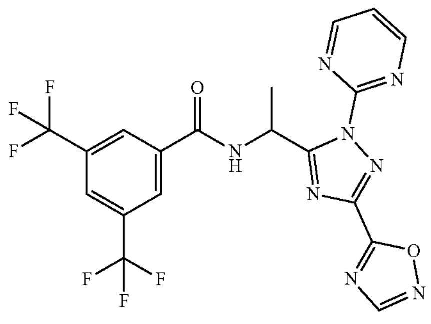

Step A: Preparation of methyl 5-[1-[[3,5-bis(trifluoromethyl)benzoyl]amino]ethyl]-1-pyrimidin-2-yl-1,2,4-triazole-3-carboxylate

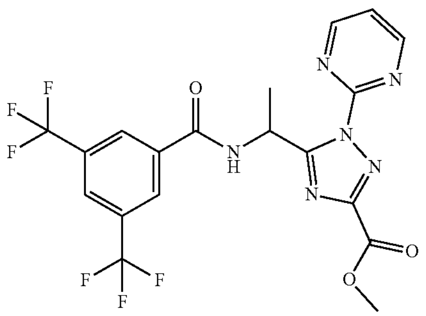 [SMILES: COC(=O)c1nc(C(C)NC(=O)c2cc(C(F)(F)F)cc(C(F)(F)F)c2)n(-c2ncccn2)n1]

In a high pressure metal reactor, triethylamine (35.6 μL, 255 μmol) and [1,3-bis(diphenylphosphino)propane]palladium(ii) dichloride (8.11 mg, 13.7 μmol) were added at room temperature to a solution of N-[1-(5-bromo-2-pyrimidin-2-yl-1,2,4-triazol-3-yl)ethyl]-3,5-bis(trifluoromethyl)benzamide (100 mg, 196 μmol) in methanol (2 mL). The reaction mixture was heated up to 100° C. and stirred overnight under a 10 bar carbon monoxide atmosphere. After cooling down at room temperature, the reaction mixture was filtered over celite and concentrated under reduced pressure. The resulting residue was diluted with ethyl acetate and washed with water and brine, dried over sodium sulfate, filtered and concentrated under reduced pressure. Purification of the crude material by flash chromatography over silica gel (eluting with methanol in dichloromethane) afforded the desired product.

LCMS: $R_t$ 0.99, m/z=489 ($M+H^+$); $^1$H-NMR (400 MHz, $CDCl_3$): δ=8.98 (d, J=4.77 Hz, 2H), 8.26 (s, 2H), 7.98 (s, 1H), 7.76 (br d, J=7.34 Hz, 1H), 7.50 (t, J=4.77 Hz, 1H), 6.54 (quin, J=7.06 Hz, 1H), 4.02 (s, 3H), 1.82-1.75 (m, 3H) ppm.

Step B: Preparation of 5-[1-[[3,5-bis(trifluoromethyl)benzoyl]amino]ethyl]-1-pyrimidin-2-yl-1,2,4-triazole-3-carboxamide (Compound P37)

P37

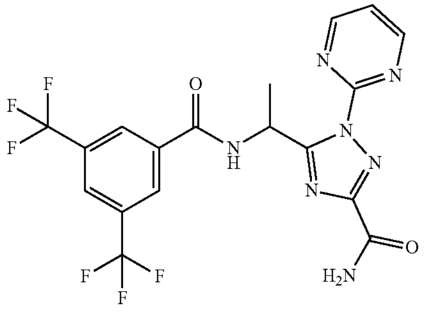

To a solution of methyl 5-[1-[[3,5-bis(trifluoromethyl)benzoyl]amino]ethyl]-1-pyrimidin-2-yl-1,2,4-triazole-3-carboxylate (35 mg, 72 μmol) in aqueous ammonia (0.350 mL) was added at room temperature lanthanum(III) trifluoromethanesulfonate (4.2 mg, 7.2 μmol). The reaction mixture was heated up to 70° C. and stirred for 2 hours. After cooling down to room temperature, the reaction mixture was concentrated under reduced pressure. Precipitation in diethyl ether afforded 5-[1-[[3,5-bis(trifluoromethyl)benzoyl]amino]ethyl]-1-pyrimidin-2-yl-1,2,4-triazole-3-carboxamide (Compound P37) as a white solid.

LCMS: $R_t$ 0.88, m/z=474 ($M+H^+$); $^1$H NMR (400 MHz, methanol-d4) δ=8.99 (d, J=5.14 Hz, 2H), 8.42 (s, 2H), 8.15 (s, 1H), 7.62 (t, J=4.77 Hz, 1H), 6.31 (s, 1H), 1.79 (d, J=6.97 Hz, 3H) ppm.

Step C: Preparation of (NE)-5-[1-[[3,5-bis(trifluoromethyl)benzoyl]amino]ethyl]-N-(dimethylaminomethylene)-1-pyrimidin-2-yl-1,2,4-triazole-3-carboxamide

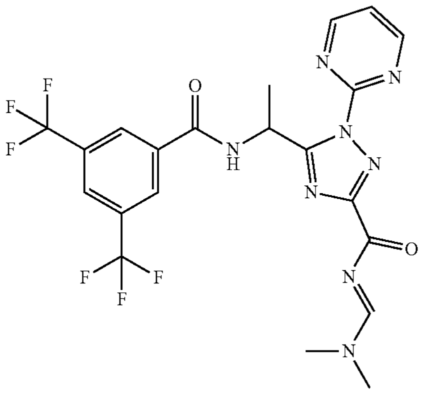 [SMILES: CC(NC(=O)c1cc(C(F)(F)F)cc(C(F)(F)F)c1)c1nc(C(=O)/N=C/N(C)C)nn1-c1ncccn1]

To a solution of 5-[1-[[3,5-bis(trifluoromethyl)benzoyl]amino]ethyl]-1-pyrimidin-2-yl-1,2,4-triazole-3-carboxamide (110 mg, 0.232 mmol) in toluene (0.93 mL) was added at room temperature 1,1-dimethoxy-N,N-dimethyl-methanamine (0.062 mL, 0.465 mmol). The reaction mixture was heated up to 100° C. and stirred for 2 hours. After cooling down to room temperature, the reaction mixture was concentrated under reduced pressure to afford (NE)-5-[1-[[3,5-bis(trifluoromethyl)benzoyl]amino]ethyl]-N-(dimethylaminomethylene)-1-pyrimidin-2-yl-1,2,4-triazole-3-carboxamide as a white solid which was used without further purification.

$^1$H NMR (400 MHz, DMSO-d6) δ=9.70-9.61 (m, 1H), 9.01 (d, J=4.77 Hz, 2H), 8.64 (s, 1H), 8.42 (s, 2H), 8.31 (s, 1H), 7.66 (s, 1H), 6.09-5.96 (m, 1H), 3.23-3.09 (m, 6H), 1.69 (d, J=6.97 Hz, 3H) ppm.

Step D: Preparation of (NE)-5-[1-[[3,5-bis(trifluoromethyl)benzoyl]amino]ethyl]-N-[(hydroxyamino)methylene]-1-pyrimidin-2-yl-1,2,4-triazole-3-carboxamide

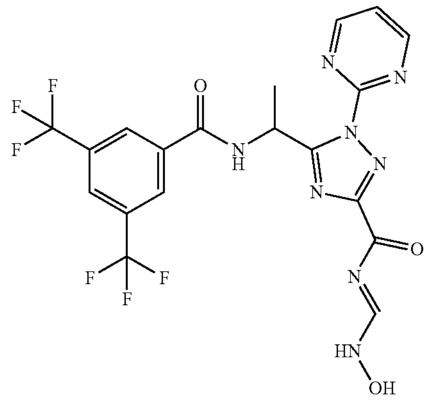 [SMILES: CC(NC(=O)c1cc(C(F)(F)F)cc(C(F)(F)F)c1)c1nc(C(=O)/N=C/NO)nn1-c1ncccn1]

To a solution of hydroxylamine hydrochloride (24.6 mg, 0.355 mmol) in acetic acid (1.25 mL) was added dropwise sodium hydroxide (1 N in water, 0.355 mL, 0.355 mmol). As the reaction was slightly exothermic, the reaction mixture was cooled to room temperature and stirred for 15 minutes. Then a solution of (NE)-5-[1-[[3,5-bis(trifluoromethyl)benzoyl]amino]ethyl]-N-(dimethylaminomethylene)-1-pyrimidin-2-yl-1,2,4-triazole-3-carboxamide (125 mg, 0.237 mmol) in acetic acid (1 mL) was added and the reaction mixture was stirred at room temperature for 1 hour then concentrated under reduced pressure to afford (NE)-5-[1-[[3,5-bis(trifluoromethyl)benzoyl]amino]ethyl]-N-[(hydroxyamino)methylene]-1-pyrimidin-2-yl-1,2,4-triazole-3-carboxamide which was used without further purification.

LCMS: $R_t$ 0.93, m/z=517 (M+H$^+$).

Step E: Preparation of N-[1-[5-(1,2,4-oxadiazol-5-yl)-2-pyrimidin-2-yl-1,2,4-triazol-3-yl]ethyl]-3,5-bis(trifluoromethyl)benzamide (compound P1)

P1

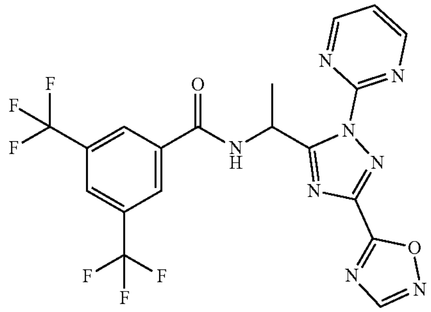

To a solution of (NE)-5-[1-[[3,5-bis(trifluoromethyl)benzoyl]amino]ethyl]-N-[(hydroxyamino)methylene]-1-pyrimidin-2-yl-1,2,4-triazole-3-carboxamide (164 mg, 0.318 mmol) in dioxane (0.79 mL) was added dropwise at room temperature acetic acid (0.79 mL). The reaction mixture was heated up to 90° C. and stirred for 2 hours. After cooling down to room temperature, the reaction mixture was quenched with water and extracted with ethyl acetate. The combined organic layers were washed with water, dried over sodium sulfate, filtered and concentrated under reduced pressure. Purification of the crude material by reverse-phase chromatography (eluting with acetonitrile in water) afforded N-[1-[5-(1,2,4-oxadiazol-5-yl)-2-pyrimidin-2-yl-1,2,4-triazol-3-yl]ethyl]-3,5-bis(trifluoromethyl)benzamide (compound P1) as a beige solid.

LCMS: $R_t$ 1.01, m/z=499 (M+H$^+$).

$^1$H-NMR (400 MHz, $CDCl_3$): δ=9.02 (d, J=4.77 Hz, 2H), 8.64 (s, 1H), 8.27 (s, 2H), 8.02 (s, 1H), 7.59-7.50 (m, 2H), 6.64-6.57 (m, 1H), 1.84 (d, J=6.97 Hz, 3H) ppm Example 6: Preparation of N-[1-[5-(1,3,4-oxadiazol-2-yl)-2-pyrimidin-2-yl-1,2,4-triazol-3-yl]ethyl]-3,5-bis(trifluoromethyl)benzamide (compound P30)

P30

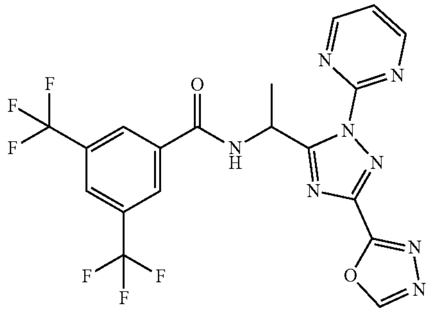

Step A: Preparation of N-[1-[5-(hydrazinecarbonyl)-2-pyrimidin-2-yl-1,2,4-triazol-3-yl]ethyl]-3,5-bis(trifluoromethyl)benzamide

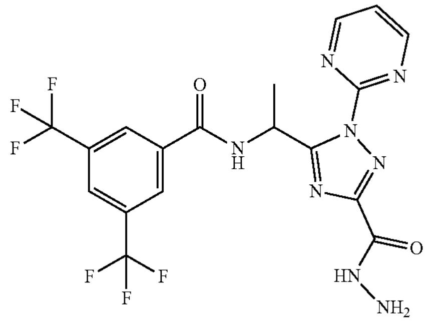 [SMILES: CC(NC(=O)c1cc(C(F)(F)F)cc(C(F)(F)F)c1)c1nc(C(=O)NN)nn1-c1ncccn1]

To a solution of methyl 5-[1-[[3,5-bis(trifluoromethyl)benzoyl]amino]ethyl]-1-pyrimidin-2-yl-1,2,4-triazole-3-carboxylate (119 mg, 0.244 mmol) in methanol (1 mL) was added at room temperature hydrazine hydrate (35%, 52 µL, 0.37 mmol). The reaction mixture was heated up to 60° C. and stirred for 1 hour. After cooling down to room temperature, the reaction mixture was concentrated under reduced pressure to afford N-[1-[5-(hydrazinecarbonyl)-2-pyrimidin-2-yl-1,2,4-triazol-3-yl]ethyl]-3,5-bis(trifluoromethyl)benzamide as a beige solid which was used without further purification.

LCMS: $R_t$ 0.87, m/z=489 (M+H$^+$).

Step B: Preparation of N-[1-[5-(1,3,4-oxadiazol-2-yl)-2-pyrimidin-2-yl-1,2,4-triazol-3-yl]ethyl]-3,5-bis(trifluoromethyl)benzamide (compound P30)

P30

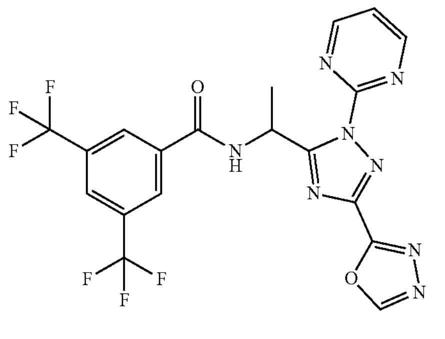

To a mixture of N-[1-[5-(hydrazinecarbonyl)-2-pyrimidin-2-yl-1,2,4-triazol-3-yl]ethyl]-3,5-bis(trifluoromethyl)benzamide (120 mg, 0.246 mmol) and trimethylorthoformate (1.38 mL) was added at room temperature p-toluenesulfonic acid (17 mg, 0.098 mmol). The reaction mixture was heated up to 140° C. and stirred for 5 hours. After cooling down to room temperature, the reaction mixture was concentrated under reduced pressure. Purification of the crude material by flash chromatography over silica gel (ethyl acetate in cyclohexane) afforded N-[1-[5-(1,3,4-oxadiazol-2-yl)-2-pyrimidin-2-yl-1,2,4-triazol-3-yl]ethyl]-3,5-bis(trifluoromethyl)benzamide (compound P30) as a white solid.

LCMS: $R_t$ 0.95, m/z=499 ($M+H^+$).

$^1$H-NMR (400 MHz, DMSO-d6): δ=9.72 (br d, J=6.60 Hz, 1H), 9.48 (s, 1H), 9.06 (d, J=4.77 Hz, 2H), 8.43 (s, 2H), 8.32 (s, 1H), 7.75-7.70 (m, 1H), 6.11 (s, 1H), 1.75 (d, J=6.97 Hz, 3H) ppm.

Example 7: Preparation of N-[1-[5-(difluoromethoxy)-2-pyrimidin-2-yl-1,2,4-triazol-3-yl]ethyl]-3,5-bis(trifluoromethyl)benzamide (compound P28)

P28

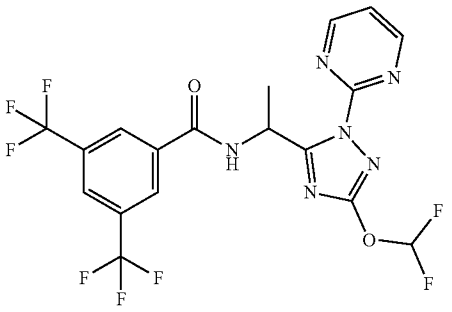

Step A: Preparation of 2-(5-ethyl-3-methoxy-1,2,4-triazol-1-yl)pyrimidine

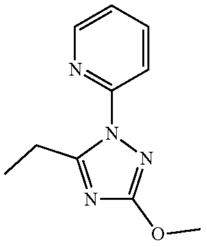

To a suspension of potassium thiocyanate (7.8 g, 79 mmol) in dry acetone (56 mL) was added at room temperature propionyl chloride (7.5 g, 79 mmol). The reaction was heated up to 60° C. and stirred for 1 hour. After cooling down to room temperature, methanol (8.1 mL) was added and the reaction was heated up to 60° C. and stirred for 14 hours. After cooling down to room temperature, the suspension was filtered over celite and the filtrate was concentrated to afford O-methyl N-propanoylcarbamothioate. A mixture of O-methyl N-propanoylcarbamothioate (7.0 g, 48 mmol) and 2-hydrazinopyrimidine (CAS 7504-94-1, 8.1 g, 71 mmol) in dry ethanol (95 mL) was heated up to 90° C. and stirred for 4 hours. After cooling down to room temperature, the reaction mixture was filtered and concentrated under reduced pressure. Purification of the crude material by flash chromatography over silica gel (isopropanol in chloroform) afforded 2-(5-ethyl-3-methoxy-1,2,4-triazol-1-yl)pyrimidine.

LCMS: $R_t$ 0.62, m/z=206 ($M+H^+$); $^1$H-NMR (400 MHz, $CDCl_3$): δ=8.84-8.80 (m, 2H), 7.27-7.24 (m, 1H), 4.11 (s, 3H), 3.28 (q, J=7.58 Hz, 2H), 1.38 (t, J=7.52 Hz, 3H) ppm.

Step B: Preparation of 2-[5-(1-bromoethyl)-3-methoxy-1,2,4-triazol-1-yl]pyrimidine

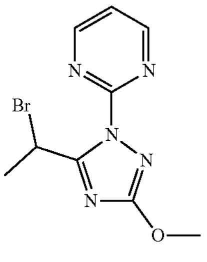 [SMILES: COc1nc(C(C)Br)n(-c2ncccn2)n1]

A mixture of 2-(5-ethyl-3-methoxy-1,2,4-triazol-1-yl)pyrimidine (1.50 g, 7.30 mmol), N-bromosuccinimide (2.1 g, 12 mmol) and benzoyl peroxide (0.18 g, 0.73 mmol) in acetonitrile (8.5 mL) was irradiated under a 230 Watt white lamp for 30 minutes. The reaction mixture was concentrated under reduced pressure. Purification of the crude material by flash chromatography over silica gel (ethyl acetate in cyclohexane) afforded 2-[5-(1-bromoethyl)-3-methoxy-1,2,4-triazol-1-yl]pyrimidine as a yellow solid.

LCMS: $R_t$ 0.75, m/z=284, 286 ($M+H^+$); $^1$H-NMR (400 MHz, DMSO-d6): δ=8.98 (d, J=4.77 Hz, 2H), 7.61 (s, 1H), 6.30 (q, J=6.97 Hz, 1H), 3.97 (s, 3H), 2.05 (d, J=6.60 Hz, 3H) ppm.

Step C: Preparation of 1-(5-methoxy-2-pyrimidin-2-yl-1,2,4-triazol-3-yl)ethanamine; hydrobromide

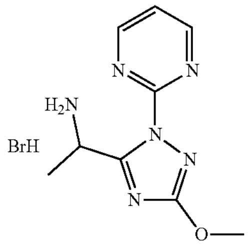 [SMILES: Br ; COc1nc(C(C)N)n(-c2ncccn2)n1]

A solution of 2-[5-(1-bromoethyl)-3-methoxy-1,2,4-triazol-1-yl]pyrimidine (2.1 g, 7.4 mmol) in ammonia (7 M in methanol, 110 mL) was stirred at room temperature for 40 hours. The reaction mixture was concentrated under reduced pressure. Trituration in diethyl ether afforded 1-(5-methoxy-2-pyrimidin-2-yl-1,2,4-triazol-3-yl)ethanamine; hydrobromide which was used without further purification.

LCMS: $R_t$ 0.18, m/z=221 (M+H$^+$).

Step D: Preparation of N-[1-(5-methoxy-2-pyrimidin-2-yl-1,2,4-triazol-3-yl)ethyl]-3,5-bis(trifluoromethyl)benzamide

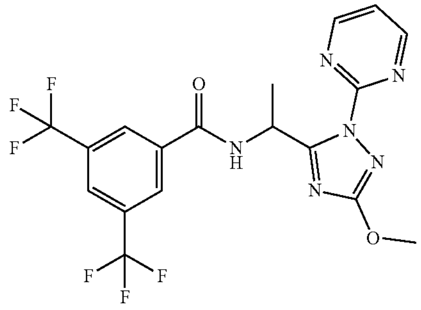 [SMILES: COc1nc(C(C)NC(=O)c2cc(C(F)(F)F)cc(C(F)(F)F)c2)n(-c2ncccn2)n1]

To a solution of 1-(5-methoxy-2-pyrimidin-2-yl-1,2,4-triazol-3-yl)ethanamine; hydrobromide (2.20 g, 6.56 mmol) and triethylamine (2.51 mL, 17.9 mmol) in dry dichloromethane (60 mL) was added dropwise at 0-5° C. 3-5-bis (trifluoromethyl)benzoyl chloride (CAS 785-56-8, 1.08 mL, 5.97 mmol). The reaction mixture was stirred at room temperature for 1 hour. After concentration under reduced pressure, the crude material was purified by flash chromatography over silica gel (ethyl acetate in cyclohexane) to afford N-[1-(5-methoxy-2-pyrimidin-2-yl-1,2,4-triazol-3-yl)ethyl]-3,5-bis(trifluoromethyl)benzamide as a yellow solid.

LCMS: $R_t$ 0.99, m/z=461 (M+H$^+$); $^1$H-NMR (400 MHz, $CDCl_3$): δ=8.97-8.81 (m, 2H), 8.33-8.19 (m, 2H), 8.08-7.97 (m, 1H), 7.60-7.46 (m, 1H), 7.44-7.31 (m, 1H), 6.58-6.33 (m, 1H), 4.26-4.08 (m, 3H), 1.80-1.68 (m, 3H) ppm; $^{19}$F NMR (377 MHz, $CDCl_3$)=−62.86 (s, 6 F) ppm.

Step E: Preparation of N-[1-(5-oxo-2-pyrimidin-2-yl-1H-1,2,4-triazol-3-yl)ethyl]-3,5-bis(trifluoromethyl)benzamide (Compound P26)

P26

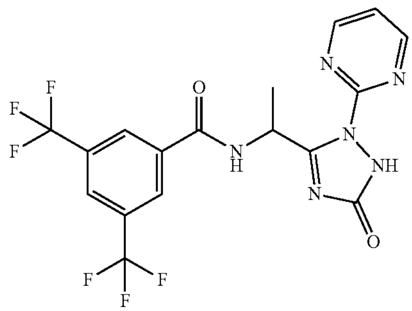

To a solution of N-[1-(5-methoxy-2-pyrimidin-2-yl-1,2,4-triazol-3-yl)ethyl]-3,5-bis(trifluoromethyl)benzamide (0.20 g, 0.43 mmol) in acetic acid (2.2 mL) was added at room temperature hydrobromic acid (33% in acetic acid, 0.76 mL, 4.3 mmol). The reaction mixture was stirred first at room temperature for 18 hours, then at 40° C. for 5 hours. After concentration under reduced pressure, the crude material was purified by flash chromatography over silica gel (ethyl acetate in cyclohexane) to afford N-[1-(5-oxo-2-pyrimidin-2-yl-1H-1,2,4-triazol-3-yl)ethyl]-3,5-bis(trifluoromethyl)benzamide (compound P26) as a yellow solid.

LCMS: $R_t$ 0.92, m/z=447 (M+H$^+$); $^1$H-NMR (400 MHz, DMSO-d6): δ=11.6 (s, 1H), 9.51 (d, J=6.97 Hz, 1H), 8.90 (d, J=4.77 Hz, 2H), 8.46 (s, 2H), 8.31 (s, 1H), 7.50 (t, J=4.77 Hz, 1H), 6.03 (t, J=6.97 Hz, 1H), 1.63 (d, J=6.97 Hz, 3H) ppm; $^{19}$F NMR (377 MHz, DMSO-d6): δ=−61.30 (s, 6 F) ppm.

Step F: Preparation of N-[1-[5-(difluoromethoxy)-2-pyrimidin-2-yl-1,2,4-triazol-3-yl]ethyl]-3,5-bis(trifluoromethyl)benzamide

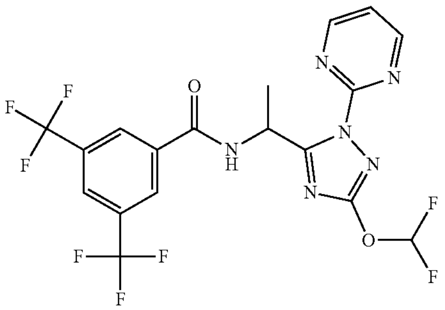 [SMILES: CC(NC(=O)c1cc(C(F)(F)F)cc(C(F)(F)F)c1)c1nc(OC(F)F)nn1-c1ncccn1]

A solution of N-[1-(5-oxo-2-pyrimidin-2-yl-1H-1,2,4-triazol-3-yl)ethyl]-3,5-bis(trifluoromethyl)benzamide (0.20 g, 0.45 mmol), chlorodifluoroacetic acid (0.30 g, 2.2 mmol) and potassium carbonate (0.63 g, 4.5 mmol) in N,N-dimethylformamide (5 mL) was heated up to 80° C. and stirred for 16 hours. After cooling down at room temperature, the reaction mixture was diluted in ethyl acetate and washed with water and brine. The combined organic layers were dried over sodium sulfate, filtered and concentrated under reduced pressure. Purification of the crude material by flash chromatography over silica gel (ethyl acetate in cyclohexane) afforded N-[1-[5-(difluoromethoxy)-2-pyrimidin-2-yl-1,2,4-triazol-3-yl]ethyl]-3,5-bis(trifluoromethyl)benzamide.

LCMS: $R_t$ 1.07, m/z=497 (M+H$^+$); $^1$H-NMR (400 MHz, $CDCl_3$): δ=8.94 (d, J=5.14 Hz, 2H), 8.25 (s, 2H), 8.05 (s, 1H), 7.43 (d, J=4.77 Hz, 1H), 7.07-7.25-7.45 (br t, 1H, $CHF_2$), 6.47 (dd, J=8.25, 6.79 Hz, 1H), 1.76 (d, J=6.60 Hz, 3H) ppm; $^{19}$F-NMR (377 MHz, $CDCl_3$): δ=−61.30 (s, 6 F), −86.16 (d, 2 F) ppm.

Example 8: Preparation of N-methyl-N-[1-[2-pyrimidin-2-yl-5-(trifluoromethylsulfonyl)-1,2,4-triazol-3-yl]ethyl]-3,5-bis(trifluoromethyl)benzamide (compound P19)

P19

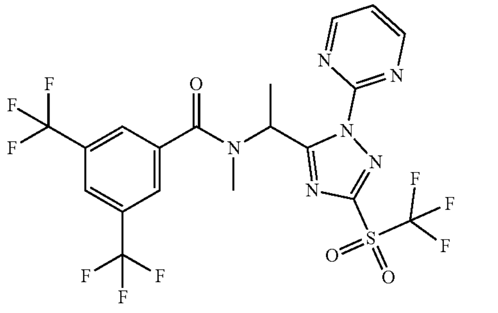

Step A: Preparation of N-methyl-N-[1-[2-pyrimidin-2-yl-5-(trifluoromethylsulfanyl)-1,2,4-triazol-3-yl]ethyl]-3,5-bis(trifluoromethyl)benzamide (P20)

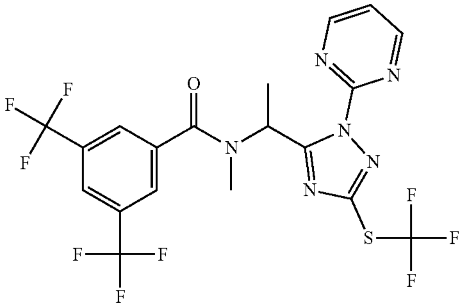 [SMILES: CC(c1nc(SC(F)(F)F)nn1-c1ncccn1)N(C)C(=O)c1cc(C(F)(F)F)cc(C(F)(F)F)c1]

To a solution of N-[1-(5-bromo-2-pyrimidin-2-yl-1,2,4-triazol-3-yl)ethyl]-N-methyl-3,5-bis(trifluoromethyl)benzamide (0.20 g, 0.38 mmol) in dry 1,4-dioxane (11 mL) was added at room temperature trifluoromethylthiolato(2,2-bipyridine)copper(I) (CAS 1413732-47-4, 0.18 g, 0.57 mmol). The reaction mixture was heated up to 100° C. and stirred for 20 hours. After cooling down at room temperature, the reaction mixture was filtered over celite and concentrated under reduced pressure. Purification of the crude material first, by flash chromatography over silica gel (ethyl acetate in cyclohexane) and then, by reverse-phase chromatography (acetonitrile in water) afforded N-methyl-N-[1-[2-pyrimidin-2-yl-5-(trifluoromethylsulfanyl)-1,2,4-triazol-3-yl]ethyl]-3,5-bis(trifluoromethyl)benzamide (P20) as a gum.

LCMS: $R_t$ 1.15, m/z=545 (M+H$^+$); $^1$H-NMR (400 MHz, $CDCl_3$): δ=8.90 (br d, J=4.40 Hz, 2H), 7.97-7.85 (m, 1H), 7.70 (s, 2H), 7.44 (br t, J=4.58 Hz, 1H), 6.75 (br d, J=6.97 Hz, 1H), 2.95 (s, 3H), 1.82 (d, J=7.34 Hz, 3H) ppm; $^{19}$F-NMR (377 MHz, $CDCl_3$): δ=−39.77 (s, 3 F), −63.02 (s, 6 F).

Step B: Preparation of N-methyl-N-[1-[2-pyrimidin-2-yl-5-(trifluoromethylsulfonyl)-1,2,4-triazol-3-yl]ethyl]-3,5-bis(trifluoromethyl)benzamide (compound P19)

P19

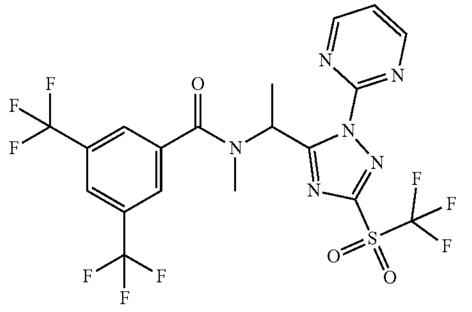

To a solution of N-methyl-N-[1-[2-pyrimidin-2-yl-5-(trifluoromethylsulfanyl)-1,2,4-triazol-3-yl]ethyl]-3,5-bis(trifluoromethyl)benzamide (55 mg, 0.10 mmol) in dichloromethane (3 mL) was added at 0° C. in three portions 3-chloroperoxybenzoic acid (29 mg, 0.12 mmol). The reaction mixture was allowed to reach room temperature and stirred for 6 days. The reaction mixture was quenched with sodium bicarbonate sat. solution. The organic layer was dried over sodium sulfate, filtered and concentrated under reduced pressure. Purification of the crude material by reverse-phase chromatography (acetonitrile in water) afforded N-methyl-N-[1-[2-pyrimidin-2-yl-5-(trifluoromethylsulfonyl)-1,2,4-triazol-3-yl]ethyl]-3,5-bis(trifluoromethyl)benzamide (compound P19) as an oil.

LCMS: $R_t$ 1.17, m/z=577 (M+H$^+$).

Example 9: Preparation of N-[(1S)-1-[2-pyrimidin-2-yl-5-(trifluoromethoxy)-1,2,4-triazol-3-yl]ethyl]-3,5-bis(trifluoromethyl)benzamide (compound P23)

P23

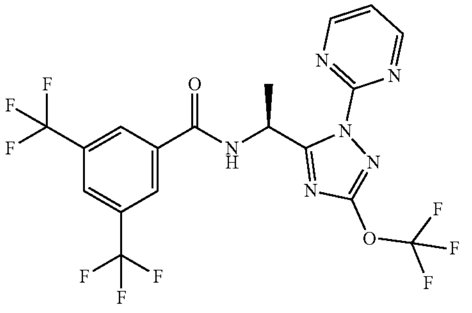

To a solution of N-[(1S)-1-(2-pyrimidin-2-yl-1,2,4-triazol-3-yl)ethyl]-3,5-bis(trifluoromethyl)benzamide (0.547 g, 1.27 mmol) in acetonitrile (13 mL) were added at room temperature 1-(trifluoromethoxy)pyridine-4-carbonitrile; 1,1,1-trifluoro-N-(trifluoromethylsulfonyl)methanesulfonamide (0.200 g, 0.424 mmol) and tris(2,2'-bipyridine)ruthenium(II) hexafluorophosphate (0.018 g, 0.021 mmol). The reaction mixture was stirred under irradiation of blue LED light for 2 hours at room temperature. After concentration under reduced pressure, the crude material was purified by flash chromatography over silica gel (methanol in dichloromethane) to afford N-[(1S)-1-[2-pyrimidin-2-yl-5-(trifluoromethoxy)-1,2,4-triazol-3-yl]ethyl]-3,5-bis(trifluoromethyl)benzamide as a yellow solid.

LCMS: $R_t$ 1.10, m/z=515 ($M+H^+$); $^1H$-NMR (400 MHz, $CDCl_3$): δ=8.96 (d, J=4.8 Hz, 2H), 8.27 (s, 2H), 8.05 (s, 1H), 7.50-7.44 (m, 1H), 7.41-7.34 (m, 1H), 6.56-6.43 (m, 1H), 1.77 (d, J=7.0 Hz, 3H) ppm.

TABLE P

Examples of compounds of formula I

| Entry | IUPAC name | STRUCTURE | RT (min) | [M + H] (measured) | MP °C. |
|---|---|---|---|---|---|
| P1 | N-[1-[5-(1,2,4-oxadiazol-5-yl)-2-pyrimidin-2-yl-1,2,4-triazol-3-yl]ethyl]-3,5-bis(trifluoromethyl) benzamide | 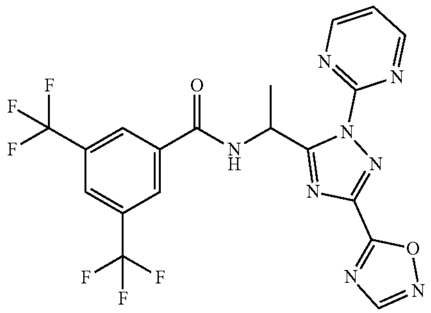 [SMILES: CC(NC(=O)c1cc(C(F)(F)F)cc(C(F)(F)F)c1)c1nc(-c2ncno2)nn1-c1ncccn1] | 1.01 | 499 | |
| P2 | N-[1-[5-(methoxymethyl)-2-pyrimidin-2-yl-1,2,4-triazol-3-yl]ethyl]-3,5-bis(trifluoromethyl)benzamide | 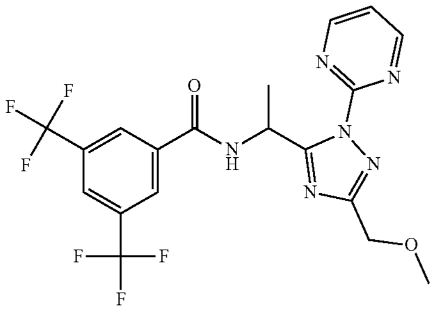 [SMILES: COCc1nc(C(C)NC(=O)c2cc(C(F)(F)F)cc(C(F)(F)F)c2)n(-c2ncccn2)n1] | | | 155-160 |
| P3 | N-[1-(5-bromo-2-pyrimidin-2-yl-1,2,4-triazol-3-yl)ethyl]-N-methyl-3,5-bis(trifluoromethyl) benzamide | 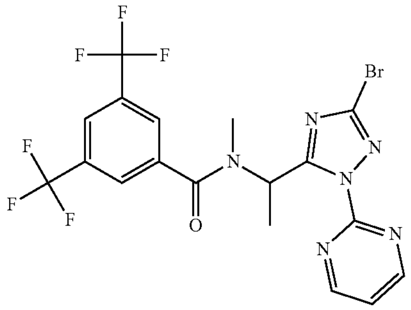 [SMILES: CC(c1nc(Br)nn1-c1ncccn1)N(C)C(=O)c1cc(C(F)(F)F)cc(C(F)(F)F)c1] | 1.05 | 523/525 | |
| P4 | N-[1-(5-bromo-2-pyrimidin-2-yl-1,2,4-triazol-3-yl)ethyl]-3,5-bis(trifluoromethyl) benzamide | 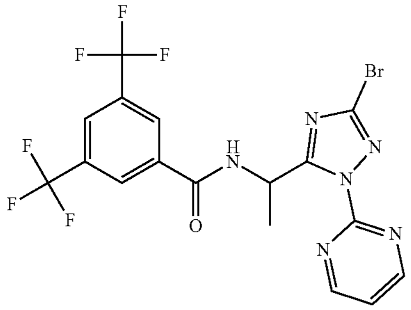 [SMILES: CC(NC(=O)c1cc(C(F)(F)F)cc(C(F)(F)F)c1)c1nc(Br)nn1-c1ncccn1] | 1.05 | 509/511 | |

TABLE P-continued

| Entry | IUPAC name | STRUCTURE | RT (min) | [M + H] (measured) | MP °C. |
|---|---|---|---|---|---|
| Examples of compounds of formula I | | | | | |
| P5 | N-(cyclopropylmethyl)-N-[1-(5-iodo-2-pyrimidin-2-yl-1,2,4-triazol-3-yl)ethyl]-3,5-bis(trifluoromethyl) benzamide | 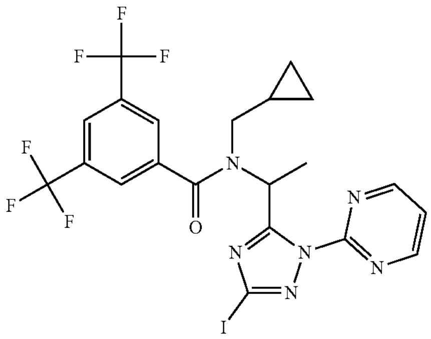 [SMILES: CC(c1nc(I)nn1-c1ncccn1)N(CC1CC1)C(=O)c1cc(C(F)(F)F)cc(C(F)(F)F)c1] | 1.14 | 611 | |
| P6 | N-methyl-N-[1-(5-phenyl-2-pyrimidin-2-yl-1,2,4-triazol-3-yl)ethyl]-3,5-bis(trifluoromethyl) benzamide | 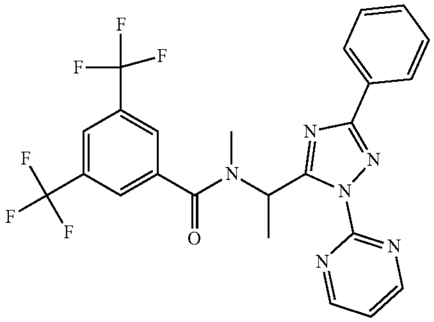 [SMILES: CC(c1nc(-c2ccccc2)nn1-c1ncccn1)N(C)C(=O)c1cc(C(F)(F)F)cc(C(F)(F)F)c1] | 1.15 | 521 | |
| P7 | N-[1-(5-amino-2-pyrimidin-2-yl-1,2,4-triazol-3-yl)ethyl]-N-methyl-3,5-bis(trifluoromethyl) benzamide | 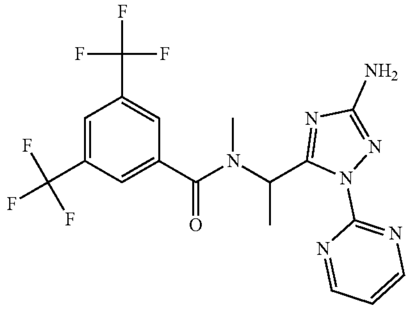 [SMILES: CC(c1nc(N)nn1-c1ncccn1)N(C)C(=O)c1cc(C(F)(F)F)cc(C(F)(F)F)c1] | 0.88 | 460 | 162-164 |
| P8 | N-methyl-N-[1(5-prop-1-ynyl-2-pyrimidin-2-yl-1,2,4-triazol-3-yl)ethyl]-3,5-bis(trifluoromethyl) benzamide | 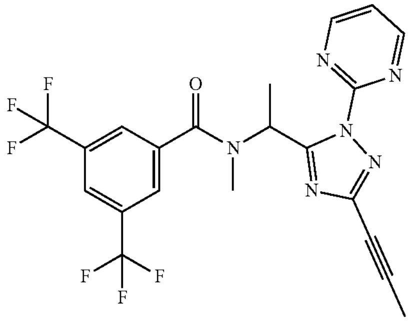 [SMILES: CC#Cc1nc(C(C)N(C)C(=O)c2cc(C(F)(F)F)cc(C(F)(F)F)c2)n(-c2ncccn2)n1] | 1.05 | 483 | |

TABLE P-continued

| Examples of compounds of formula I | | | | | |
|---|---|---|---|---|---|
| Entry | IUPAC name | STRUCTURE | RT (min) | [M + H] (measured) | MP °C. |
| P9 | N-[1-(5-cyano-2-pyrimidin-2-yl-1,2,4-triazol-3-yl)ethyl]-N-methyl-3,5-bis(trifluoromethyl) benzamide | 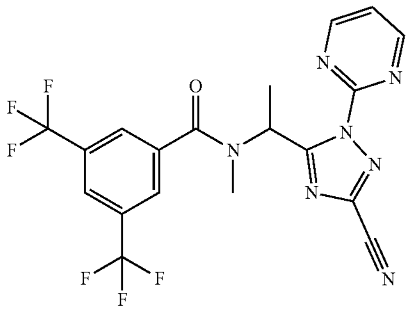 [SMILES: CC(c1nc(C#N)nn1-c1ncccn1)N(C)C(=O)c1cc(C(F)(F)F)cc(C(F)(F)F)c1] | 1.05 | 470 | |
| P10 | N-methyl-N-[1-[2-pyrimidin-2-yl-5-(3,3,3-trifluoroprop-1-ynyl)-1,2,4-triazol-3-yl]ethyl]-3,5-bis(trifluoromethyl) benzamide | 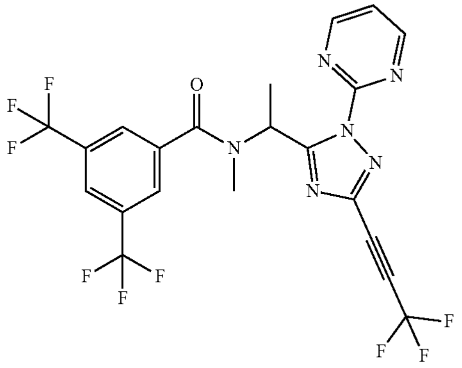 [SMILES: CC(c1nc(C#CC(F)(F)F)nn1-c1ncccn1)N(C)C(=O)c1cc(C(F)(F)F)cc(C(F)(F)F)c1] | 1.18 | 537 | |
| P11 | 5-[1-[[3,5-bis(trifluoromethyl) benzoyl]-methyl-amino]ethyl]-N,N-dimethyl-1-pyrimidin-2-yl-1,2,4-triazole-3-carboxamide | 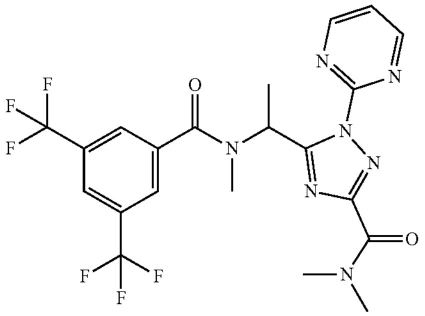 [SMILES: CC(c1nc(C(=O)N(C)C)nn1-c1ncccn1)N(C)C(=O)c1cc(C(F)(F)F)cc(C(F)(F)F)c1] | | | 55-57 |
| P12 | 5-[1-[[3.5-bis(trifluoromethyl) benzoyl]-methyl-amino]ethyl]-N-methyl-1-pyrimidin-2-yl-1,2,4-triazole-3-carboxamide | 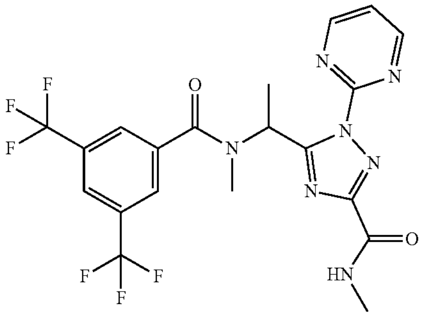 [SMILES: CNC(=O)c1nc(C(C)N(C)C(=O)c2cc(C(F)(F)F)cc(C(F)(F)F)c2)n(-c2ncccn2)n1] | | | 78-79 |

TABLE P-continued

Examples of compounds of formula I

| Entry | IUPAC name | STRUCTURE | RT (min) | [M + H] (measured) | MP °C. |
|---|---|---|---|---|---|
| P13 | N-methyl-N-[1-(2-pyrimidin-2-yl-5-vinyl-1,2,4-triazol-3-yl)ethyl]-3,5-bis(trifluoromethyl) benzamide | 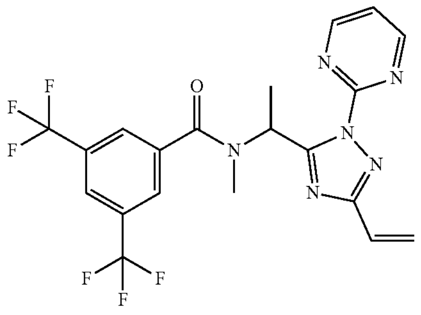 [SMILES: C=Cc1nc(C(C)N(C)C(=O)c2cc(C(F)(F)F)cc(C(F)(F)F)c2)n(-c2ncccn2)n1] | 1.05 | 471 | |
| P14 | N-[1-[5-(1-fluorovinyl)-2-pyrimidin-2-yl-1,2,4-triazol-3-yl]ethyl]-N-methyl-3,5-bis(trifluoromethyl) benzamide | 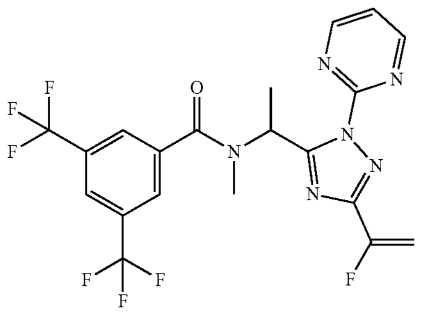 [SMILES: C=C(F)c1nc(C(C)N(C)C(=O)c2cc(C(F)(F)F)cc(C(F)(F)F)c2)n(-c2ncccn2)n1] | 1.08 | 489 | |
| P15 | N-[1-(5-chloro-2-pyrimidin-2-yl-1,2,4-triazol-3-yl)ethyl]-N-methyl-3,5-bis(trifluoromethyl) benzamide | 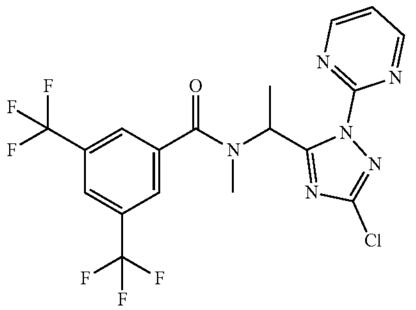 [SMILES: CC(c1nc(Cl)nn1-c1ncccn1)N(C)C(=O)c1cc(C(F)(F)F)cc(C(F)(F)F)c1] | 1.05 | 479 | |
| P16 | N-[1-[5-(dimethylamino)-2-pyrimidin-2-yl-1,2,4-triazol-3-yl]ethyl]-N-methyl-3,5-bis(trifluoromethyl) benzamide | 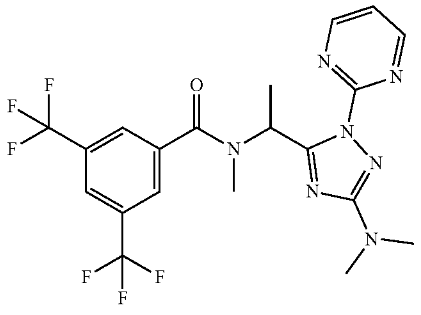 [SMILES: CC(c1nc(N(C)C)nn1-c1ncccn1)N(C)C(=O)c1cc(C(F)(F)F)cc(C(F)(F)F)c1] | 1.04 | 488 | |

TABLE P-continued

| Examples of compounds of formula I | | | | | |
|---|---|---|---|---|---|
| Entry | IUPAC name | STRUCTURE | RT (min) | [M + H] (measured) | MP °C. |
| P17 | N-[1-(5-acetamido-2-pyrimidin-2-yl-1,2,4-triazol-3-yl)ethyl]-N-methyl-3,5-bis(trifluoromethyl) benzamide | 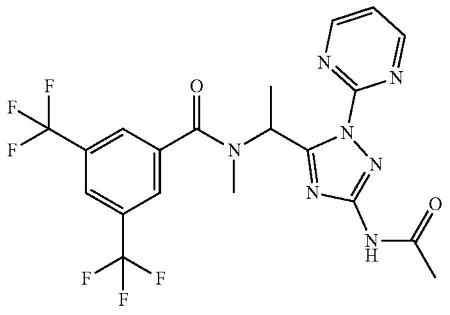 [SMILES: CC(=O)Nc1nc(C(C)N(C)C(=O)c2cc(C(F)(F)F)cc(C(F)(F)F)c2)n(-c2ncccn2)n1] | 0.99 | 502 | |
| P18 | N-methyl-N-[1-[5-(methylamino)-2-pyrimidin-2-yl-1,2,4-triazol-3-yl]ethyl]-3,5-bis(trifluoromethyl) benzamide | 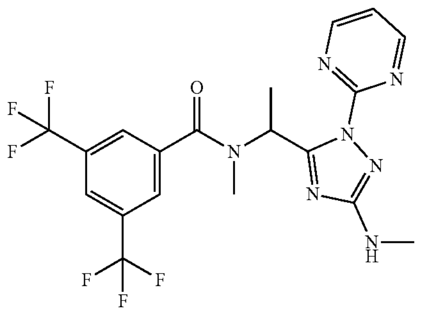 [SMILES: CNc1nc(C(C)N(C)C(=O)c2cc(C(F)(F)F)cc(C(F)(F)F)c2)n(-c2ncccn2)n1] | 0.93 | 474 | |
| P19 | N-methyl-N-[1-[2-pyrimidin-2-yl-5-(trifluoromethylsulfonyl)-1,2,4-triazol-3-yl]ethyl]-3,5-bis(trifluoromethyl) benzamide | 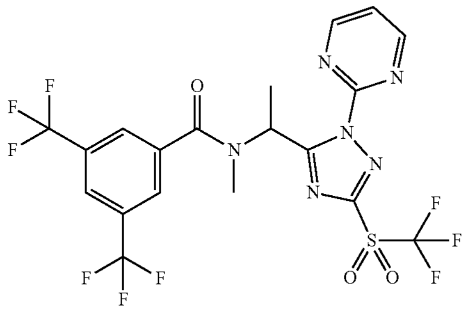 [SMILES: CC(c1nc(S(=O)(=O)C(F)(F)F)nn1-c1ncccn1)N(C)C(=O)c1cc(C(F)(F)F)cc(C(F)(F)F)c1] | 1.17 | 577 | |
| P20 | N-methyl-N-[1-[2-pyrimidin-2-yl-5-(trifluoromethylsulfanyl)-1,2,4-triazol-3-yl]ethyl]-3,5-bis(trifluoromethyl) benzamide | 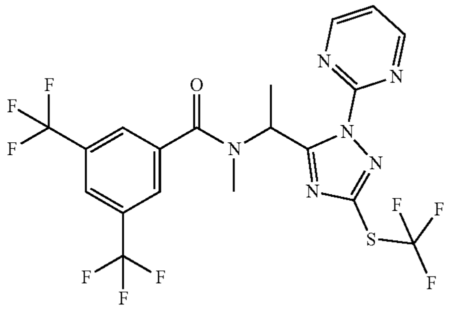 [SMILES: CC(c1nc(SC(F)(F)F)nn1-c1ncccn1)N(C)C(=O)c1cc(C(F)(F)F)cc(C(F)(F)F)c1] | 1.15 | 545 | |

TABLE P-continued

| Examples of compounds of formula I | | | | | |
|---|---|---|---|---|---|
| Entry | IUPAC name | STRUCTURE | RT (min) | [M + H] (measured) | MP °C. |
| P21 | N-[1-(5-methylsulfonyl-2-pyrimidin-2-yl-1,2,4-triazol-3-yl)ethyl]-3,5-bis(trifluoromethyl) benzamide | 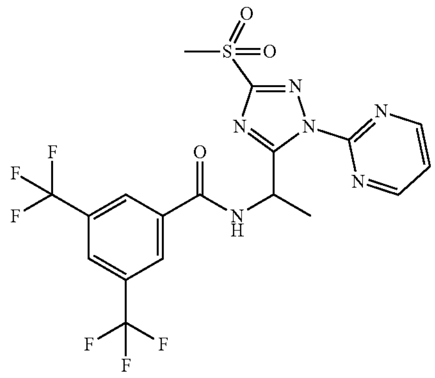 [SMILES: CC(NC(=O)c1cc(C(F)(F)F)cc(C(F)(F)F)c1)c1nc(S(C)(=O)=O)nn1-c1ncccn1] | 0.98 | 509 | |
| P22 | N-[1-[5-(benzhydrylideneamino)-2-pyrimidin-2-yl-1,2,4-triazol-3-yl]ethyl]-N-methyl-3,5-bis(trifluoromethyl) benzamide | 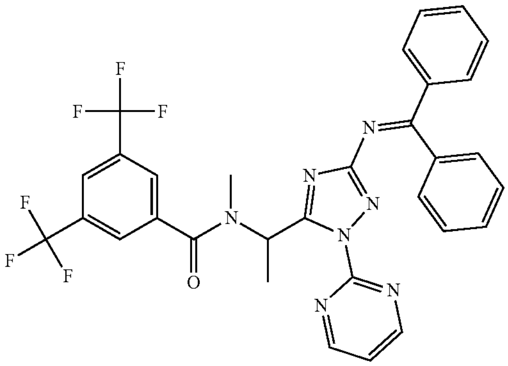 [SMILES: CC(c1nc(N=C(c2ccccc2)c2ccccc2)nn1-c1ncccn1)N(C)C(=O)c1cc(C(F)(F)F)cc(C(F)(F)F)c1] | 1.19 | 624 | |
| P23 | N-[(1S)-1-[2-pyrimidin-2-yl-5-(trifluoromethoxy)-1,2,4-triazol-3-yl]ethyl]-3,5-bis(trifluoromethyl) benzamide | 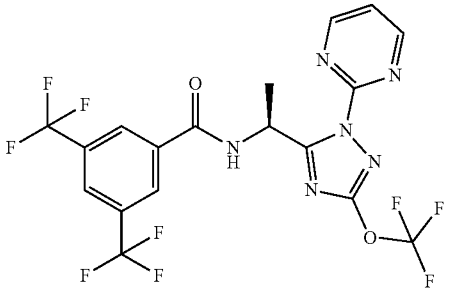 [SMILES: C[C@H](NC(=O)c1cc(C(F)(F)F)cc(C(F)(F)F)c1)c1nc(OC(F)(F)F)nn1-c1ncccn1] | 1.10 | 515 | |
| P24 | N-[1-[5-bromo-2-(2-pyridyl)-1,2,4-triazol-3-yl]ethyl]-N-methyl-3,5-bis(trifluoromethyl) benzamide | 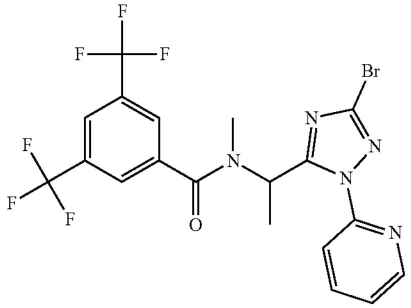 [SMILES: CC(c1nc(Br)nn1-c1ccccn1)N(C)C(=O)c1cc(C(F)(F)F)cc(C(F)(F)F)c1] | 1.15 | 523/525 | |

TABLE P-continued

Examples of compounds of formula I

| Entry | IUPAC name | STRUCTURE | RT (min) | [M + H] (measured) | MP °C. |
|---|---|---|---|---|---|
| P25 | N-[1-[2-(2-pyridyl)-5-(trifluoromethoxy)-1,2,4-triazol-3-yl]ethyl]-3,5-bis(trifluoromethyl) benzamide | 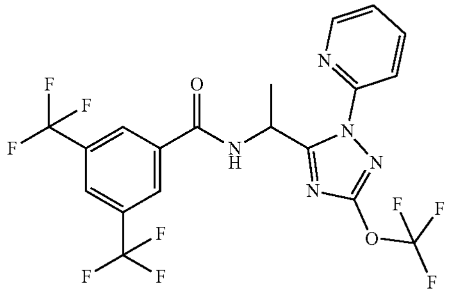 [SMILES: CC(NC(=O)c1cc(C(F)(F)F)cc(C(F)(F)F)c1)c1nc(OC(F)(F)F)nn1-c1ccccn1] | 1.23 | 514 | |
| P26 | N-[1-(5-hydroxy-2-pyrimidin-2-yl-1,2)4-triazol-3-yl)ethyl]-3,5-bis(trifluoromethyl) benzamide | 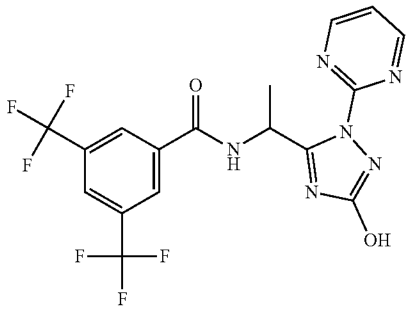 [SMILES: CC(NC(=O)c1cc(C(F)(F)F)cc(C(F)(F)F)c1)c1nc(O)nn1-c1ncccn1] | 0.92 | 447 | |
| P27 | N-[1-[2-pyrimidin-2-yl-5-(2,2,2-trifluoroethoxy)-1,2,4-triazol-3-yl]ethyl]-3,5-bis(trifluoromethyl) benzamide | 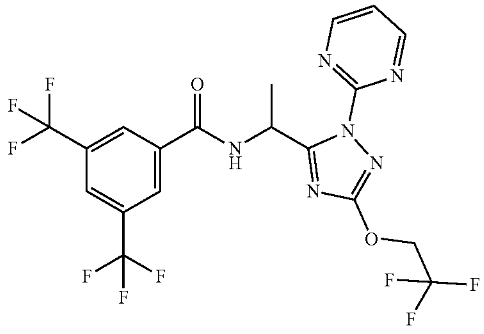 [SMILES: CC(NC(=O)c1cc(C(F)(F)F)cc(C(F)(F)F)c1)c1nc(OCC(F)(F)F)nn1-c1ncccn1] | 1.09 | 529 | |
| P28 | N-[1-[5-(difluoromethoxy)-2-pyrimidin-2-yl-1,2,4-triazol-3-yl]ethyl]-3,5-bis(trifluoromethyl) benzamide | 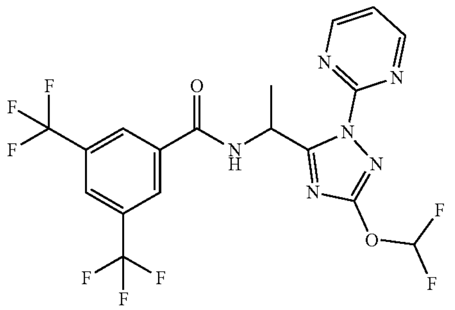 [SMILES: CC(NC(=O)c1cc(C(F)(F)F)cc(C(F)(F)F)c1)c1nc(OC(F)F)nn1-c1ncccn1] | 1.07 | 497 | |

TABLE P-continued

| Examples of compounds of formula I | | | | | |
|---|---|---|---|---|---|
| Entry | IUPAC name | STRUCTURE | RT (min) | [M + H] (measured) | MP °C. |
| P29 | N-[1-[5-(2,2-difluoroethoxy)-2-pyrimidin-2-yl-1,2,4-triazol-3-yl]ethyl]-3,5-bis(trifluoromethyl) benzamide | 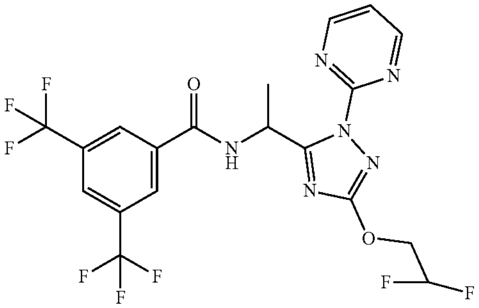 [SMILES: CC(NC(=O)c1cc(C(F)(F)F)cc(C(F)(F)F)c1)c1nc(OCC(F)F)nn1-c1ncccn1] | 1.05 | 511 | |
| P30 | N-[1-[5-(1,3,4-oxadiazol-2-yl)-2-pyrimidin-2-yl-1,2,4-[triazol-3-yl]ethyl]-3,5-bis(trifluoromethyl) benzamide | 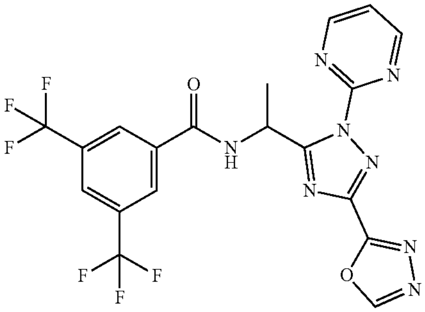 [SMILES: CC(NC(=O)c1cc(C(F)(F)F)cc(C(F)(F)F)c1)c1nc(-c2nnco2)nn1-c1ncccn1] | | | 245-246 |
| P31 | 3-bromo-N-[1-(5-bromo-2-pyrimidin-2-yl-1,2,4-triazol-3-yl)ethyl]-5-(trifluoromethyl) benzamide | 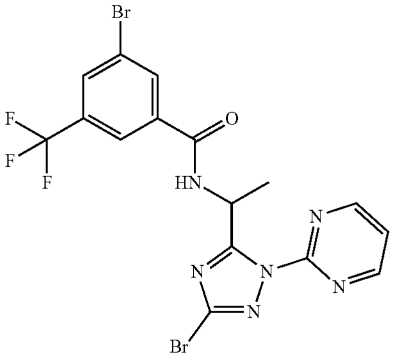 [SMILES: CC(NC(=O)c1cc(Br)cc(C(F)(F)F)c1)c1nc(Br)nn1-c1ncccn1] | | | 125-130 |
| P32 | N-[1-(5-bromo-2-pyrimidin-2-yl-1,2,4-triazol-3-yl)ethyl]-3-chloro-5-(trifluoromethoxy)benzamide | 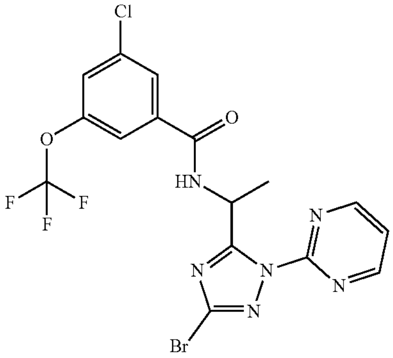 [SMILES: CC(NC(=O)c1cc(Cl)cc(OC(F)(F)F)c1)c1nc(Br)nn1-c1ncccn1] | | | 75-80 |

TABLE P-continued

Examples of compounds of formula I

| Entry | IUPAC name | STRUCTURE | RT (min) | [M + H] (measured) | MP °C. |
| --- | --- | --- | --- | --- | --- |
| P33 | N-[1-(5-bromo-2-pyrimidin-2-yl-1,2,4-triazol-3-yl)ethyl]-3-chloro-5-(trifluoromethyl) benzamide | 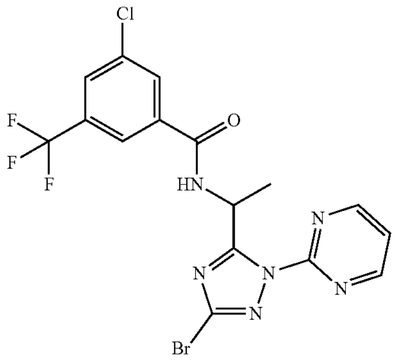 [SMILES: CC(NC(=O)c1cc(Cl)cc(C(F)(F)F)c1)c1nc(Br)nn1-c1ncccn1] | | | 215-220 |
| P34 | N-[1-(5-chloro-2-pyrimidin-2-yl-1,2,4-triazol-3-yl)ethyl]-3,5-bis(trifluoromethyl) benzamide | 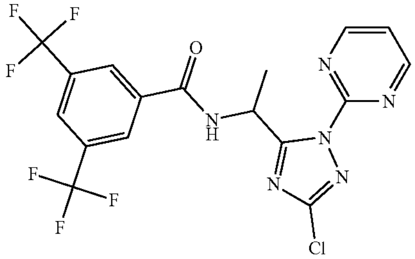 [SMILES: CC(NC(=O)c1cc(C(F)(F)F)cc(C(F)(F)F)c1)c1nc(Cl)nn1-c1ncccn1] | | | 225-226 |
| P35 | N-[1-(5-acetyl-2-pyrimidin-2-yl-1,2,4-triazol-3-yl)ethyl]-3,5-bis(trifluoromethyl) benzamide | 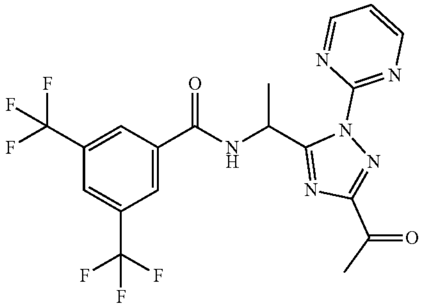 [SMILES: CC(=O)c1nc(C(C)NC(=O)c2cc(C(F)(F)F)cc(C(F)(F)F)c2)n(-c2ncccn2)n1] | | | 210-211 |
| P36 | N-[1-[5-(2-methoxyethoxy)-2-pyrimidin-2-yl-1,2,4-triazol-3-yl]ethyl]-3,5-bis(trifluoromethyl) benzamide | 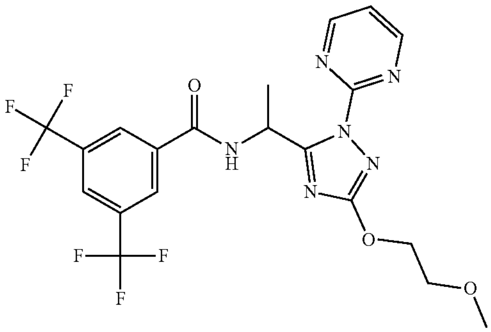 [SMILES: COCCOc1nc(C(C)NC(=O)c2cc(C(F)(F)F)cc(C(F)(F)F)c2)n(-c2ncccn2)n1] | 1.00 | 505 | |

TABLE P-continued

| Examples of compounds of formula I | | | | | |
|---|---|---|---|---|---|
| Entry | IUPAC name | STRUCTURE | RT (min) | [M + H] (measured) | MP °C. |
| P37 | 5-[1-[[3,5-bis(trifluoromethyl) benzoyl]-methyl-amino]ethyl]-1-pyrimidin-2-yl-1,2,4-triazole-3-earboxamide | 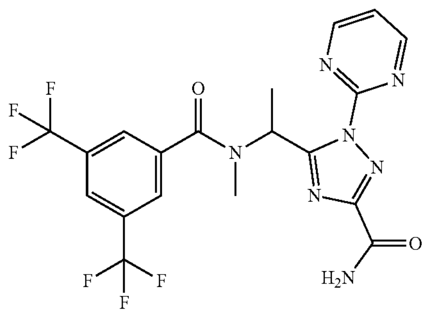 [SMILES: CC(c1nc(C(N)=O)nn1-c1ncccn1)N(C)C(=O)c1cc(C(F)(F)F)cc(C(F)(F)F)c1] | | | 225-226 |
| P38 | N-[1-(5-formyl-2-pyrimidin-2-yl-1,2,4-triazol-3-yl)ethyl]-3,5-bis(trifluoromethyl) benzamide | 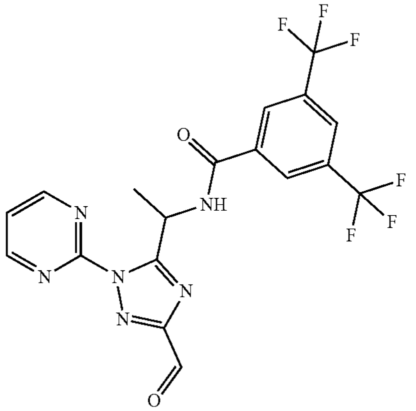 [SMILES: CC(NC(=O)c1cc(C(F)(F)F)cc(C(F)(F)F)c1)c1nc(C=O)nn1-c1ncccn1] | | | 200-205 |

TABLE I

| Table of Intermediates: | | | | | |
|---|---|---|---|---|---|
| Entry | IUPAC name | STRUCTURE | RT (min) | [M + H] (measured) | MP, °C. |
| I1 | N-(cyclopropylmethyl)-N-[1-(3-iodo-1H-1,2,4-triazol-5-yl)ethyl]-3,5-bis(trifluoromethyl) benzamide | | 1.05 | 533 | — |
| I2 | N-[1-(3-bromo-1H-1,2,4-triazol-5-yl)ethyl]-N-(cyclopropyl-methyl)-3,5-bis (trifluoromethyl) benzamide | | 1.06 | 485/487 | — |
| I3 | N-methyl-N-[1-(3-phenyl-1H-1,2,4-triazol-5-yl)ethyl]-3,5-bis(trifluoromethyl) benzamide | 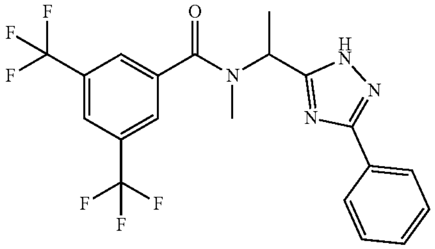 [SMILES: CC(c1nc(-c2ccccc2)n[nH]1)N(C)C(=O)c1cc(C(F)(F)F)cc(C(F)(F)F)c1] | 1.14 | 483 | — |

TABLE I-continued

| Table of Intermediates: | | | | | |
|---|---|---|---|---|---|
| Entry | IUPAC name | STRUCTURE | RT (min) | [M + H] (measured) | MP, °C. |
| I4 | N-[1-[3-(4-fluorophenyl)-1H-1,2,4-triazol-5-yl]ethyl]-3,5-bis(trifluoromethyl) benzamide | 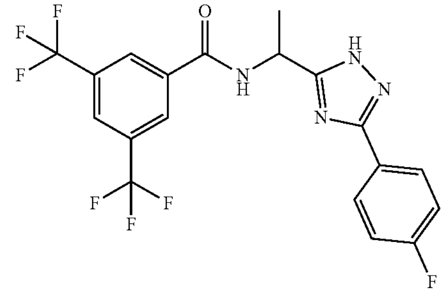 [SMILES: CC(NC(=O)c1cc(C(F)(F)F)cc(C(F)(F)F)c1)c1nc(-c2ccc(F)cc2)n[nH]1] | 1.04 | 447 | — |
| I5 | N-[1-(3-bromo-1H-1,2,4-triazol-5-yl)ethyl]-3,5-bis(trifluoromethyl) benzamide | 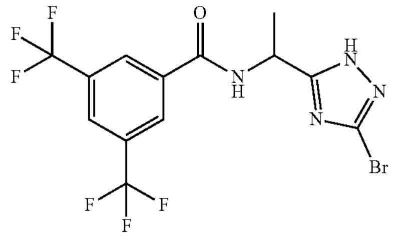 [SMILES: CC(NC(=O)c1cc(C(F)(F)F)cc(C(F)(F)F)c1)c1nc(Br)n[nH]1] | 0.96 | 431/433 | — |
| I6 | N-[1-(3-bromo-1H-1,2,4-triazol-5-yl)ethyl]-N-methyl-3,5-bis(trifluoromethyl) benzamide | 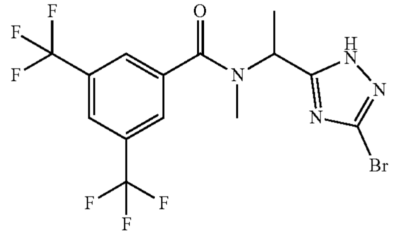 [SMILES: CC(c1nc(Br)n[nH]1)N(C)C(=O)c1cc(C(F)(F)F)cc(C(F)(F)F)c1] | 0.98 | 445/447 | — |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (where the abbreviation "TX" means "one compound selected from the compounds defined in the Tables A-1 to A-92 and Table P"):

an adjuvant selected from the group of substances consisting of petroleum oils (alternative name) (628)+TX, an insect control active substance selected from Abamectin+TX, Acequinocyl+TX, Acetamiprid+TX, Acetoprole+TX, Acrinathrin+TX, Acynonapyr+TX, Afidopyropen+TX, Afoxalaner+TX, Alanycarb+TX, Allethrin+TX, Alpha-Cypermethrin+TX, Alphamethrin+TX, Amidoflumet+TX, Aminocarb+TX, Azocyclotin+TX, Bensultap+TX, Benzoximate+TX, Benzpyrimoxan+TX, Betacyfluthrin+TX, Betacypermethrin+TX, Bifenazate+TX, Bifenthrin+TX, Binapacryl+TX, Bioallethrin+TX, Bioallethrin S)-cyclopentylisomer+TX, Bioresmethrin+TX, Bistrifluron+TX, Broflanilide+TX, Brofluthrinate+TX, Bromophos-ethyl+TX, Buprofezine+TX, Butocarboxim+TX, Cadusafos+TX, Carbaryl+TX, Carbosulfan+TX, Cartap+TX, CAS number: 1472050-04-6+TX, CAS number: 1632218-00-8+TX, CAS number: 1808115-49-2+TX, CAS number: 2032403-97-5+TX, CAS number: 2044701-44-0+TX, CAS number: 2128706-05-6+TX, CAS number: 2249718-27-0+TX, Chlorantraniliprole+TX, Chlordane+TX, Chlorfenapyr+TX, Chloroprallethrin+TX, Chromafenozide+TX, Clenpirin+TX, Cloethocarb+TX, Clothianidin+TX, 2-chlorophenyl N-methylcarbamate (CPMC)+TX, Cyanofenphos+TX, Cyantraniliprole+TX, Cyclaniliprole+TX, Cycloprothrin+TX, Cycloxaprid+TX, Cycloxaprid+TX, Cyenopyrafen+TX, Cyetpyrafen (or Etpyrafen)+TX, Cyflumetofen+TX, Cyfluthrin+TX, Cyhalodiamide+TX, Cyhalothrin+TX, Cypermethrin+TX, Cyphenothrin+TX, Cyromazine+TX, Deltamethrin+TX, Diafenthiuron+TX, Dialifos+TX, Dibrom+TX, Dicloromezotiaz+TX, Diflovidazine+TX, Diflubenzuron+TX, dimpropyridaz+TX, Dinactin+TX, Dinocap+TX, Dinotefuran+TX, Dioxabenzofos+TX, Emamectin+TX, Empenthrin+TX, Epsilon—momfluorothrin+TX, Epsilon-metofluthrin+TX, Esfenvalerate+TX, Ethion+TX, Ethiprole+TX, Etofenprox+TX, Etoxazole+TX, Famphur+TX, Fenazaquin+TX, Fenfluthrin+TX, Fenitrothion+TX, Fenobucarb+TX, Fenothiocarb+TX, Fenoxycarb+TX, Fenpropathrin+TX, Fenpyroxymate+TX, Fensulfothion+TX, Fenthion+TX, Fentinacetate+TX, Fenvalerate+TX, Fipronil+TX, Flometoquin+TX, Flonicamid+TX, Fluacrypyrim+TX, Fluazaindolizine+TX, Fluazuron+TX, Flubendiamide+TX, Flubenzimine+TX, Flucitrinate+TX, Flucycloxuron+TX, Flucythrinate+TX, Fluensulfone+TX, Flufenerim+TX, Flufenprox+TX, Flufiprole+TX, Fluhexafon+TX, Flumethrin+TX, Fluopyram+TX, Flupyradifurone+TX, Flupyrimin+TX, Fluralaner+TX, Fluvalinate+TX, Fluxametamide+TX, Fosthiazate+TX, Gamma-Cyhalothrin+TX, Gossyplure™+TX, Guadipyr+TX, Halofenozide+TX, Halofenozide+TX, Halofenprox+TX, Heptafluthrin+TX, Hexythiazox+TX, Hydramethylnon+TX, Imicyafos+TX, Imidacloprid+TX, Imiprothrin+TX, Indoxacarb+TX, Iodomethane+TX, Iprodione+TX, Isocycloseram+TX, Isothioate+TX, Ivermectin+TX, Kappa-bifenthrin+TX, Kappa-tefluthrin+TX, Lambda-Cyhalothrin+TX, Lepimectin+TX, Lufenuron+TX, Metaflumizone+TX, Metaldehyde+TX, Metam+TX, Methomyl+TX, Methoxyfenozide+TX, Metofluthrin+TX, Metolcarb+TX, Mexacarbate+TX, Milbemectin+TX, Momfluorothrin+TX, Niclosamide+TX, Nitenpyram+TX, Nithiazine+TX, Omethoate+TX, Oxamyl+TX, Oxazosufyl+TX, Parathion-ethyl+TX, Permethrin+TX, Phenothrin+TX, Phosphocarb+TX, Piperonylbutoxide+TX, Pirimicarb+TX, Pirimiphos-ethyl+TX, Polyhedrosis virus+TX, Prallethrin+TX, Profenofos+TX, Profenofos+TX, Profluthrin+TX, Propargite+TX, Propetamphos+TX, Propoxur+TX, Prothiophos+TX, Protrifenbute+TX, Pyflubumide+TX, Pymetrozine+TX, Pyraclofos+TX, Pyrafluprole+TX, Pyridaben+TX, Pyridalyl+TX, Pyrifluquinazon+TX, Pyrimidifen+TX, Pyrimostrobin+TX, Pyriprole+TX, Pyriproxyfen+TX, Resmethrin+TX, Sarolaner+TX, Selamectin+TX, Silafluofen+TX, Spinetoram+TX, Spinosad+TX, Spirodiclofen+TX, Spiromesifen+TX, Spiropidion+TX, Spirotetramat+TX, Sulfoxaflor+TX, Tebufenozide+TX, Tebufenpyrad+TX, Tebupirimiphos+TX, Tefluthrin+TX, Temephos+TX, Tetrachloraniliprole+TX, Tetradiphon+TX, Tetramethrin+TX, Tetramethylfluthrin+TX, Tetranactin+TX, Tetraniliprole+TX, Theta-cypermethrin+TX, Thiacloprid+TX, Thiamethoxam+TX, Thiocyclam+TX, Thiodicarb+TX, Thiofanox+TX, Thiometon+TX, Thiosultap+TX, Tioxazafen+TX, Tolfenpyrad+TX, Toxaphene+TX, Tralomethrin+TX, Transfluthrin+TX, Triazamate+TX, Triazophos+TX, Trichlorfon+TX, Trichloronate+TX, Trichlorphon+TX, Triflumezopyrim+TX, Tyclopyrazoflor+TX, Zeta-Cypermethrin+TX, Extract of seaweed and fermentation product derived from melasse+TX, Extract of seaweed and fermentation product derived from melasse comprising urea+TX, amino acids+TX, potassium and molybdenum and EDTA-chelated manganese+TX, Extract of seaweed and fermented plant products+TX, Extract of seaweed and fermented plant products comprising phytohormones+TX, vitamins+TX, EDTA-chelated copper+TX, zinc+TX, and iron+TX, Azadirachtin+TX, *Bacillus aizawai*+TX, *Bacillus chitinosporus* AQ746 (NRRL Accession No B-21 618)+TX, *Bacillus firmus*+TX, *Bacillus kurstaki*+TX, *Bacillus mycoides* AQ726 (NRRL Accession No. B-21664)+TX, *Bacillus pumilus* (NRRL Accession No B-30087)+TX, *Bacillus pumilus* AQ717 (NRRL Accession No. B-21662)+TX, *Bacillus* sp. AQ178 (ATCC Accession No. 53522)+TX, *Bacillus* sp. AQ175 (ATCC Accession No. 55608)+TX, *Bacillus* sp. AQ177 (ATCC Accession No. 55609)+TX, *Bacillus subtilis* unspecified+TX, *Bacillus subtilis* AQ153 (ATCC Accession No. 55614)+TX, *Bacillus subtilis* AQ30002 (NRRL Accession No. B-50421)+TX, *Bacillus subtilis* AQ30004 (NRRL Accession No. B-50455)+TX, *Bacillus subtilis* AQ713 (NRRL Accession No. B-21661)+TX, *Bacillus subtilis* AQ743 (NRRL Accession No. B-21665)+TX, *Bacillus thuringiensis* AQ52 (NRRL Accession No. B-21619)+TX, *Bacillus thuringiensis* BD #32 (NRRL Accession No B-21530)+TX, *Bacillus thuringiensis* subspec. *kurstaki* BMP 123+TX, *Beauveria bassiana*+TX, D-limonene+TX, Granulovirus+TX, Harpin+TX, *Helicoverpa armigera* Nucleopolyhedrovirus+TX, *Helicoverpa zea* Nucleopolyhedrovirus+TX, *Heliothis virescens* Nucleopolyhedrovirus+TX, *Heliothis punctigera* Nucleopolyhedrovirus+TX, *Metarhizium* spp.+TX, *Muscodor albus* 620 (NRRL Accession No. 30547)+TX, *Muscodor roseus* A3-5 (NRRL Accession No. 30548)+TX, Neem tree based products+TX, *Paecilomyces fumosoroseus*+TX, *Paecilomyces lilacinus*+TX, *Pasteuria nishizawae*+TX, *Pasteuria penetrans*+TX, *Pasteuria ramosa*+TX, *Pasteuria thornei*+TX, *Pasteuria usgae*+TX, P-cymene+TX, *Plutella xylostella* Granulosis virus+TX, *Plutella xylostella* Nucleopolyhedrovirus+TX, Polyhedrosis virus+TX, pyrethrum+TX, QRD 420 (a terpenoid blend)+TX, QRD 452 (a terpenoid blend)+TX, QRD 460 (a terpenoid blend)+TX, *Quillaja saponaria*+TX, *Rhodococcus globerulus* AQ719 (NRRL Accession No B-21663)+TX, *Spodoptera frugiperda* Nucleopolyhedrovirus+TX, *Streptomyces galbus* (NRRL Accession No. 30232)+TX, *Streptomyces* sp. (NRRL Accession No. B-30145)+TX, Terpenoid blend+TX, and *Verticillium* spp., an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, fluopyram+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, a biologically active substance selected from 1,1-bis(4-chlorophenyl)-2-ethoxyethanol+TX, 2,4-dichlorophenyl benzenesulfonate+TX, 2-fluoro-N-methyl-N-1-naphthylacetamide+TX, 4-chlorophenyl phenyl sulfone+TX, acetoprole+TX, aldoxycarb+TX, amidithion+TX, amidothioate+TX, amiton+TX, amiton hydrogen oxalate+TX, amitraz+TX, aramite+TX, arsenous oxide+TX, azobenzene+TX, azothoate+TX, benomyl+TX, benoxafos+TX, benzyl benzoate+TX, bixafen+TX, brofenvalerate+TX, bromocyclen+TX, bromophos+TX, bromopropylate+TX, buprofezin+TX, butocarboxim+TX, butoxycarboxim+TX, butylpyridaben+TX, calcium polysulfide+TX, camphechlor+TX, carbanolate+TX, carbophenothion+TX, cymiazole+TX, chinomethionat+TX, chlorbenside+TX, chlordimeform+TX, chlordimeform hydrochloride+TX, chlorfenethol+TX, chlorfenson+TX, chlorfensulfide+TX, chlorobenzilate+TX, chloromebuform+TX, chloromethiuron+TX, chloropropylate+TX, chlorthiophos+TX, cinerin I+TX, cinerin II+TX, cinerins+TX, closantel+TX, coumaphos+TX, crotamiton+TX, crotoxyphos+TX, cufraneb+TX, cyanthoate+TX, DCPM+TX, DDT+TX, demephion+TX, demephion-O+TX, demephion-S+TX, demeton-methyl+TX, demeton-O+TX, demeton-O-methyl+TX, demeton-S+TX, demeton-S-methyl+TX, demeton-S-methylsulfon+TX, dichlofluanid+TX, dichlorvos+TX, dicliphos+TX, dienochlor+TX, dimefox+TX, dinex+TX, dinex-diclexine+TX, dinocap-4+TX, dinocap-6+TX, dinocton+TX, dinopenton+TX, dinosulfon+TX, dinoterbon+TX, dioxathion+TX, diphenyl sulfone+TX, disulfiram+TX, DNOC+TX, dofenapyn+TX, doramectin+TX, endothion+TX, eprinomectin+TX, ethoate-methyl+TX, etrimfos+TX, fenazaflor+TX, fenbutatin oxide+TX, fenothiocarb+TX, fenpyrad+TX, fen-pyroximate+TX, fenpyrazamine+TX, fenson+TX, fentrifanil+TX, flubenzimine+TX, flucycloxuron+TX, fluenetil+TX, fluorbenside+TX, FMC 1137+TX, formetanate+TX, formetanate hydrochloride+TX, formparanate+TX, gamma-HCH+TX, glyodin+TX, halfenprox+TX, hexadecyl cyclopropanecarboxylate+TX, isocarbophos+TX, jasmolin I+TX, jasmolin II+TX, jodfenphos+TX, lindane+TX, malonoben+TX, mecarbam+TX, mephosfolan+TX, mesulfen+TX, methacrifos+TX, methyl bromide+TX, metolcarb+TX, mexacarbate+TX, milbemycin oxime+TX, mipafox+TX, monocrotophos+TX, morphothion+TX, moxidectin+TX, naled+TX, 4-chloro-2-(2-chloro-2-methyl-propyl)-5-[(6-iodo-3-pyridyl)methoxy]pyridazin-3-one+TX, nifluridide+TX, nikkomycins+TX, nitrilacarb+TX, nitrilacarb 1:1 zinc chloride complex+TX, omethoate+TX, oxydeprofos+TX, oxydisulfoton+TX, pp'-DDT+TX, parathion+TX, permethrin+TX, phenkapton+TX, phosalone+TX, phosfolan+TX, phosphamidon+TX, polychloroterpenes+TX, polynactins+TX, proclonol+TX, promacyl+TX, propoxur+TX, prothidathion+TX, prothoate+TX, pyrethrin I+TX, pyrethrin II+TX, pyrethrins+TX, pyridaphenthion+TX, pyrimitate+TX, quinalphos+TX, quintiofos+TX, R-1492+TX, phosglycin+TX, rotenone+TX, schradan+TX, sebufos+TX, selamectin+TX, sophamide+TX, SSI-121+TX, sulfiram+TX, sulfluramid+TX, sulfotep+TX, sulfur+TX, diflovidazin+TX, tau-fluvalinate+TX, TEPP+TX, terbam+TX, tetradifon+TX, tetrasul+TX, thiafenox+TX, thiocarboxime+TX, thiofanox+TX, thiometon+TX, thioquinox+TX, thuringiensin+TX, triamiphos+TX, triarathene+TX, triazophos+TX, triazuron+TX, trifenofos+TX, trinactin+TX, vamidothion+TX, vaniliprole+TX, bethoxazin+TX, copper dioctanoate+TX, copper sulfate+TX, cybutryne+TX, dichlone+TX, dichlorophen+TX, endothal+TX, fentin+TX, hydrated lime+TX, nabam+TX, quinoclamine+TX, quinonamid+TX, simazine+TX, triphenyltin acetate+TX, triphenyltin hydroxide+TX, crufomate+TX, piperazine+TX, thiophanate+TX, chloralose+TX, fenthion+TX, pyridin-4-amine+TX, strychnine+TX, 1-hydroxy-1H-pyridine-2-thione+TX, 4-(quinoxalin-2-ylamino)benzenesulfonamide+TX, 8-hydroxyquinoline sulfate+TX, bronopol+TX, copper hydroxide+TX, cresol+TX, dipyrithione+TX, dodicin+TX, fenaminosulf+TX, formaldehyde+TX, hydrargaphen+TX, kasugamycin+TX, kasugamycin hydrochloride hydrate+TX, nickel bis (dimethyldithiocarbamate)+TX, nitrapyrin+TX, octhilinone+TX, oxolinic acid+TX, oxytetracycline+TX, potassium hydroxyquinoline sulfate+TX, probenazole+TX, streptomycin+TX, streptomycin sesquisulfate+TX, tecloftalam+TX, thiomersal+TX, *Adoxophyes orana* GV+TX, *Agrobacterium radiobacter*+TX, *Amblyseius* spp.+TX, *Anagrapha falcifera* NPV+TX, *Anagrus atomus*+TX, *Aphelinus abdominalis*+TX, *Aphidius colemani*+TX, *Aphidoletes aphidimyza*+TX, *Autographa californica* NPV+TX, *Bacillus sphaericus* Neide+TX, *Beauveria brongniartii*+TX, *Chrysoperla carnea*+TX, *Cryptolaemus montrouzieri*+TX, *Cydia pomonella* GV+TX, *Dacnusa sibirica*+TX, *Diglyphus isaea*+TX, *Encarsia formosa*+TX, *Eretmocerus eremicus*+TX, *Heterorhabditis bacteriophora* and *H. megidis*+TX, *Hippodamia convergens*+TX, *Leptomastix dactylopii*+TX, *Macrolophus caliginosus*+TX, *Mamestra brassicae* NPV+TX, *Metaphycus helvolus*+TX, *Metarhizium anisopliae* var. *acridum*+TX, *Metarhizium anisopliae* var. *anisopliae*+TX, *Neodiprion sertifer* NPV and *N. lecontei* NPV+TX, *Orius* spp.+TX, *Paecilomyces fumosoroseus*+TX, *Phytoseiulus persimilis*+TX, *Steinernema bibionis*+TX, *Steinernema carpocapsae*+TX, *Steinernema feltiae*+TX, *Steinernema glaseri*+TX, *Steinernema riobrave*+TX, *Steinernema riobravis*+TX, *Steinernema scapterisci*+TX, *Steinernema* spp.+TX, *Trichogramma* spp.+TX, *Typhlodromus occidentalis*+TX, *Verticillium lecanii*+TX, apholate+TX, bisazir+TX, busulfan+TX, dimatif+TX, hemel+TX, hempa+TX, metepa+TX, methiotepa+TX, methyl apholate+TX, morzid+TX, penfluron+TX, tepa+TX, thiohempa+TX, thiotepa+TX, tretamine+TX, uredepa+TX, (E)-dec-5-en-1-yl acetate with (E)-dec-5-en-1-ol+TX, (E)-tridec-4-en-1-yl acetate+TX, (E)-6-methylhept-2-en-4-ol+TX, (E,Z)-tetradeca-4,10-dien-1-yl acetate+TX, (Z)-dodec-7-en-1-yl acetate+TX, (Z)-hexadec-11-enal+TX, (Z)-hexadec-11-en-1-yl acetate+TX, (Z)-hexadec-13-en-11-yn-1-yl acetate+TX, (Z)-icos-13-en-10-one+TX, (Z)-tetradec-7-en-1-al+TX, (Z)-tetradec-9-en-1-ol+TX, (Z)-tetradec-9-en-1-yl acetate+TX, (7E,9Z)-dodeca-7,9-dien-1-yl acetate+TX, (9Z,11E)-tetradeca-9,11-dien-1-yl acetate+TX, (9Z,12E)-tetradeca-9,12-dien-1-yl acetate+TX, 14-methyloctadec-1-ene+TX, 4-methylnonan-5-ol with 4-methylnonan-5-one+TX, alpha-multistriatin+TX, brevicomin+TX, codlelure+TX, codlemone+TX, cuelure+TX, disparlure+TX, dodec-8-en-1-yl acetate+TX, dodec-9-en-1-yl acetate+TX, dodeca-8+TX, 10-dien-1-yl acetate+TX, dominicalure+TX, ethyl 4-methyloctanoate+TX, eugenol+TX, frontalin+TX, grandlure+TX, grandlure I+TX, grandlure II+TX, grandlure III+TX, grandlure IV+TX, hexalure+TX, ipsdienol+TX, ipsenol+TX, japonilure+TX, lineatin+TX, litlure+TX, looplure+TX, medlure+TX, megatomoic acid+TX, methyl eugenol+TX, muscalure+TX, octadeca-2,13-dien-1-yl acetate+TX, octadeca-3,13-dien-1-yl acetate+TX, orfralure+TX, oryctalure+TX, ostramone+TX, siglure+TX, sordidin+TX, sulcatol+TX, tetradec-11-en-1-yl acetate+TX, trimedlure+TX, trimedlure A+TX, trimedlure $B_1$+TX, trimedlure $B_2$+TX, trimedlure C+TX, trunc-call+TX, 2-(octylthio)ethanol+TX, butopyronoxyl+TX, butoxy(polypropylene glycol)+TX, dibutyl adipate+TX, dibutyl phthalate+TX, dibutyl succinate+TX, diethyltoluamide+TX, dimethyl carbate+TX, dimethyl phthalate+TX, ethyl hexanediol+TX, hexamide+TX, methoquin-butyl+TX, methylneodecanamide+TX, oxamate+TX, picaridin+TX, 1-dichloro-1-nitroethane+TX, 1,1-dichloro-2,2-bis(4-ethylphenyl)ethane+TX, 1,2-dichloropropane with 1,3-dichloropropene+TX, 1-bromo-2-chloroethane+TX, 2,2,2-trichloro-1-(3,4-dichlorophenyl)ethyl acetate+TX, 2,2-dichlorovinyl 2-ethylsulfinylethyl methyl phosphate+TX, 2-(1,3-dithiolan-2-yl)phenyl dimethylcarbamate+TX, 2-(2-butoxyethoxy)ethyl thiocyanate+TX, 2-(4,5-dimethyl-1,3-dioxolan-2-yl)phenyl methylcarbamate+TX, 2-(4-chloro-3,5-xylyloxy)ethanol+TX, 2-chlorovinyl diethyl phosphate+TX, 2-imidazolidone+TX, 2-isovalerylindan-1,3-dione+TX, 2-methyl(prop-2-ynyl)aminophenyl methylcarbamate+TX, 2-thiocyanatoethyl laurate+TX, 3-bromo-1-chloroprop-1-ene+TX, 3-methyl-1-phenylpyrazol-5-yl dimethylcarbamate+TX, 4-methyl(prop-2-ynyl)amino-3,5-xylyl methylcarbamate+TX, 5,5-dimethyl-3-oxocyclohex-1-enyl dimethylcarbamate+TX, acethion+TX, acrylonitrile+TX, aldrin+TX, allosamidin+TX, allyxycarb+TX, alpha-ecdysone+TX, aluminium phosphide+TX, aminocarb+TX, anabasine+TX, athidathion+TX, azamethiphos+TX, *Bacillus thuringiensis* delta endotoxins+TX, barium hexafluorosilicate+TX, barium polysulfide+TX, barthrin+TX, Bayer 22/190+TX, Bayer 22408+TX, beta-cyfluthrin+TX, beta-cypermethrin+TX, bioethanomethrin+TX, biopermethrin+TX, bis(2-chloroethyl) ether+TX, borax+TX, bromfenvinfos+TX, bromo-DDT+TX, bufencarb+TX, butacarb+TX, butathiofos+TX, butonate+TX, calcium arsenate+TX, calcium cyanide+TX, carbon disulfide+TX, carbon tetrachloride+TX, cartap hydrochloride+TX, cevadine+TX, chlorbicyclen+TX, chlordane+TX, chlordecone+TX, chloroform+TX, chloropicrin+TX, chlorphoxim+TX, chlorprazophos+TX, cis-resmethrin+TX, cismethrin+TX, clocythrin+TX, copper acetoarsenite+TX, copper arsenate+TX, copper oleate+TX, coumithoate+TX, cryolite+TX, CS 708+TX, cyanofenphos+TX, cyanophos+TX, cyclethrin+TX, cythioate+TX, d-tetramethrin+TX, DAEP+TX, dazomet+TX, decarbofuran+TX, diamidafos+TX, dicapthon+TX, dichlofenthion+TX, dicresyl+TX, dicyclanil+TX, dieldrin+TX, diethyl 5-methylpyrazol-3-yl phosphate+TX, dilor+TX, dimefluthrin+TX, dimetan+TX, dimethrin+TX, dimethylvinphos+TX, dimetilan+TX, dinoprop+TX, dinosam+TX, dinoseb+TX, diofenolan+TX, dioxabenzofos+TX, dithicrofos+TX, DSP+TX, ecdysterone+TX, EI 1642+TX, EMPC+TX, EPBP+TX, etaphos+TX, ethiofencarb+TX, ethyl formate+TX, ethylene dibromide+TX, ethylene dichloride+TX, ethylene oxide+TX, EXD+TX, fenchlorphos+TX, fenethacarb+TX, fenitrothion+TX, fenoxacrim+TX, fenpirithrin+TX, fensulfothion+TX, fenthion-ethyl+TX, flucofuron+TX, fosmethilan+TX, fospirate+TX, fosthietan+TX, furathiocarb+TX, furethrin+TX, guazatine+TX, guazatine acetates+TX, sodium tetrathiocarbonate+TX, halfenprox+TX, HCH+TX, HEOD+TX, heptachlor+TX, heterophos+TX, HHDN+TX, hydrogen cyanide+TX, hyquincarb+TX, IPSP+TX, isazofos+TX, isobenzan+TX, isodrin+TX, isofenphos+TX, isolane+TX, isoprothiolane+TX, isoxathion+TX, juvenile hormone I+TX, juvenile hormone II+TX, juvenile hormone III+TX, kelevan+TX, kinoprene+TX, lead arsenate+TX, leptophos+TX, lirimfos+TX, lythidathion+TX, m-cumenyl methylcarbamate+TX, magnesium phosphide+TX, mazidox+TX, mecarphon+TX, menazon+TX, mercurous chloride+TX, mesulfenfos+TX, metam+TX, metam-potassium+TX, metam-sodium+TX, methanesulfonyl fluoride+TX, methocrotophos+TX, methoprene+TX, methothrin+TX, methoxychlor+TX, methyl isothiocyanate+TX, methylchloroform+TX, methylene chloride+TX, metoxadiazone+TX, mirex+TX, naftalofos+TX, naphthalene+TX, NC-170+TX, nicotine+TX, nicotine sulfate+TX, nithiazine+TX, nornicotine+TX, O-5-dichloro-4-iodophenyl O-ethyl ethylphosphonothioate+TX, O,O-diethyl O-4-methyl-2-oxo-2H-chromen-7-yl phosphorothioate+TX, O,O-diethyl O-6-methyl-2-propylpyrimidin-4-yl phosphorothioate+TX, O,O,O',O'-tetrapropyl dithiopyrophosphate+TX, oleic acid+TX, para-dichlorobenzene+TX, parathion-methyl+TX, pentachlorophenol+TX, pentachlorophenyl laurate+TX, PH 60-38+TX, phenkapton+TX, phosnichlor+TX, phosphine+TX, phoxim-methyl+TX, pirimetaphos+TX, polychlorodicyclopentadiene isomers+TX, potassium arsenite+TX, potassium thiocyanate+TX, precocene I+TX, precocene II+TX, precocene III+TX, primidophos+TX, profluthrin+TX, promecarb+TX, prothiofos+TX, pyrazophos+TX, pyresmethrin+TX, quassia+TX, quinalphos-methyl+TX, quinothion+TX, rafoxanide+TX, resmethrin+TX, rotenone+TX, kadethrin+TX, ryania+TX, ryanodine+TX, sabadilla)+TX, schradan+TX, sebufos+TX, SI-0009+TX, thiapronil+TX, sodium arsenite+TX, sodium cyanide+TX, sodium fluoride+TX, sodium hexafluorosilicate+TX, sodium pentachlorophenoxide+TX, sodium selenate+TX, sodium thiocyanate+TX, sulcofuron+TX, sulcofuron-sodium+TX, sulfuryl fluoride+TX, sulprofos+TX, tar oils+TX, tazimcarb+TX, TDE+TX, tebupirimfos+TX, temephos+TX, terallethrin+TX, tetrachloroethane+TX, thicrofos+TX, thiocyclam+TX, thiocyclam hydrogen oxalate+TX, thionazin+TX, thiosultap+TX, thiosultap-sodium+TX, tralomethrin+TX, transpermethrin+TX, triazamate+TX, trichlormetaphos-3+TX, trichloronat+TX, trimethacarb+TX, tolprocarb+TX, triclopyricarb+TX, triprene+TX, veratridine+TX, veratrine+TX, XMC+TX, zetamethrin+TX, zinc phosphide+TX, zolaprofos+TX, and meperfluthrin+TX, tetramethylfluthrin+TX, bis(tributyltin) oxide+TX, bromoacetamide+TX, ferric phosphate+TX, niclosamide-olamine+TX, tributyltin oxide+TX, pyrimorph+TX, trifenmorph+TX, 1,2-dibromo-3-chloropropane+TX, 1,3-dichloropropene+TX, 3,4-dichlorotetrahydrothiophene 1,1-dioxide+TX, 3-(4-chlorophenyl)-5-methylrhodanine+TX, 5-methyl-6-thioxo-1,3,5-thiadiazinan-3-ylacetic acid+TX, 6-isopentenylaminopurine+TX, benclothiaz+TX, cytokinins+TX, DCIP+TX, furfural+TX, isamidofos+TX, kinetin+TX, *Myrothecium verrucaria* composition+TX, tetrachlorothiophene+TX, xylenols+TX, zeatin+TX, potassium ethylxanthate+TX, acibenzolar+TX, acibenzolar-S-methyl+TX, *Reynoutria sachalinensis* extract+TX, alpha-chlorohydrin+TX, antu+TX, barium carbonate+TX, bisthiosemi+TX, brodifacoum+TX, bromadiolone+TX, bromethalin+TX, chlorophacinone+TX, cholecalciferol+TX, coumachlor+TX, coumafuryl+TX, coumatetralyl+TX, crimidine+TX, difenacoum+TX, difethialone+TX, diphacinone+TX, ergocalciferol+TX, flocoumafen+TX, fluoroacetamide+TX, flupropadine+TX, flupropadine hydrochloride+TX, norbormide+TX, phosacetim+TX, phosphorus+TX, pindone+TX, pyrinuron+TX, scilliroside+TX, sodium fluoroacetate+TX, thallium sulfate+TX, warfarin+TX, 2-(2-butoxyethoxy)ethyl piperonylate+TX, 5-(1,3-benzodioxol-5-yl)-3-hexylcyclohex-2-enone+TX, farnesol with nerolidol+TX, verbutin+TX, MGK 264+TX, piperonyl butoxide+TX, piprotal+TX, propyl isomer+TX, S421+TX, sesamex+TX, sesasmolin+TX, sulfoxide+TX, anthraquinone+TX, copper naphthenate+TX, copper oxychloride+TX, dicyclopentadiene+TX, thiram+TX, zinc naphthenate+TX, ziram+TX, imanin+TX, ribavirin+TX, mercuric oxide+TX, thiophanate-methyl+TX, azaconazole+TX, bitertanol+TX, bromuconazole+TX, cyproconazole+TX, difenoconazole+TX, diniconazole+TX, epoxiconazole+TX, fenbuconazole+TX, fluquinconazole+TX, flusilazole+TX, flutriafol+TX, furametpyr+TX, hexaconazole+TX, imazalil+TX, imibenconazole+TX, ipconazole+TX, metconazole+TX, myclobutanil+TX, paclobutrazole+TX, pefurazoate+TX, penconazole+TX, prothioconazole+TX, pyrifenox+TX, prochloraz+TX, propiconazole+TX, pyrisoxazole+TX, simeconazole+TX, tebuconazole+TX, tetraconazole+TX, triadimefon+TX, triadimenol+TX, triflumizole+TX, triticonazole+TX, ancymidol+TX, fenarimol+TX, nuarimol+TX, bupirimate+TX, dimethirimol+TX, ethirimol+TX, dodemorph+TX, fenpropidine+TX, fenpropimorph+TX, spiroxamine+TX, tridemorph+TX, cyprodinil+TX, mepanipyrim+TX, pyrimethanil+TX, fenpiclonil+TX, fludioxonil+TX, benalaxyl+TX, furalaxyl+TX, metalaxyl+TX, R-metalaxyl+TX, ofurace+TX, oxadixyl+TX, carbendazim+TX, debacarb+TX, fuberidazole+TX, thiabendazole+TX, chlozolinate+TX, dichlozoline+TX, myclozoline+TX, procymidone+TX, vinclozoline+TX, boscalid+TX, carboxin+TX, fenfuram+TX, flutolanil+TX, mepronil+TX, oxycarboxin+TX, penthiopyrad+TX, thifluzamide+TX, dodine+TX, iminoctadine+TX, azoxystrobin+TX, dimoxystrobin+TX, enestroburin+TX, fenaminstrobin+TX, flufenoxystrobin+TX, fluoxastrobin+TX, kresoxim-methyl+TX, metominostrobin+TX, trifloxystrobin+TX, orysastrobin+TX, picoxystrobin+TX, pyraclostrobin+TX, pyrametostrobin+TX, pyraoxystrobin+TX, ferbam+TX, mancozeb+TX, maneb+TX, metiram+TX, propineb+TX, zineb+TX, captafol+TX, captan+TX, fluoroimide+TX, folpet+TX, tolylfluanid+TX, bordeaux mixture+TX, copper oxide+TX, mancopper+TX, oxine-copper+TX, nitrothal-isopropyl+TX, edifenphos+TX, iprobenphos+TX, phosdiphen+TX, tolclofos-methyl+TX, anilazine+TX, benthiavalicarb+TX, blasticidin-S+TX, chloroneb+TX, chlorothalonil+TX, cyflufenamid+TX, cymoxanil+TX, diclocymet+TX, diclomezine+TX, dicloran+TX, diethofencarb+TX, dimethomorph+TX, flumorph+TX, dithianon+TX, ethaboxam+TX, etridiazole+TX, famoxadone+TX, fenamidone+TX, fenoxanil+TX, ferimzone+TX, fluazinam+TX, fluopicolide+TX, flusulfamide+TX, fluxapyroxad+TX, fenhexamid+TX, fos-etyl-aluminium+TX, hymexazol+TX, iprovalicarb+TX, cyazofamid+TX, methasulfocarb+TX, metrafenone+TX, pencycuron+TX, phthalide+TX, polyoxins+TX, propamocarb+TX, pyribencarb+TX, proquinazid+TX, pyroquilon+TX, pyriofenone+TX, quinoxyfen+TX, quintozene+TX, tiadinil+TX, triazoxide+TX, tricyclazole+TX, triforine+TX, validamycin+TX, valifenalate+TX, zoxamide+TX, mandipropamid+TX, isopyrazam+TX, sedaxane+TX, benzovindiflupyr+TX, pydiflumetofen+TX, 3-difluoromethyl-1-methyl-1H-pyrazole-4-carboxylic acid (3',4',5'-trifluoro-biphenyl-2-yl)-amide+TX, isoflucypram+TX, isotianil+TX, dipymetitrone+TX, 6-ethyl-5,7-dioxo-pyrrolo[4,5][1,4]dithiino[1,2-c]isothiazole-3-carbonitrile+TX, 2-(difluoromethyl)-N-[3-ethyl-1,1-dimethyl-indan-4-yl] pyridine-3-carboxamide+TX, 4-(2,6-difluorophenyl)-6-methyl-5-phenyl-pyridazine-3-carbonitrile+TX, (R)-3-(difluoromethyl)-1-methyl-N-[1,1,3-trimethylindan-4-yl]pyrazole-4-carboxamide+TX, 4-(2-bromo-4-fluoro-phenyl)-N-(2-chloro-6-fluoro-phenyl)-2,5-dimethyl-pyrazol-3-amine+TX, 4-(2-bromo-4-fluorophenyl)-N-(2-chloro-6-fluorophenyl)-1,3-dimethyl-1H-pyrazol-5-amine+TX, fluindapyr+TX, coumethoxystrobin (jiaxiangjunzhi)+TX, Ivbenmixianan+TX, dichlobentiazox+TX, mandestrobin+TX, 3-(4,4-difluoro-3,4-dihydro-3,3-dimethylisoquinolin-1-yl)quinolone+TX, 2-[2-fluoro-6-[(8-fluoro-2-methyl-3-quinolyl)oxy]phenyl]propan-2-ol+TX, oxathiapiprolin+TX, tert-butyl N-[6-[[[(1-methyltetrazol-5-yl)-phenyl-methylene]amino]oxymethyl]-2-pyridyl]carbamate+TX, pyraziflumid+TX, inpyrfluxam+TX, trolprocarb+TX, mefentrifluconazole+TX, ipfentrifluconazole+TX, 2-(difluoromethyl)-N-[(3R)-3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine+TX, [2-[3-[2-[1-[2-[3,5-bis(difluoromethyl)pyrazol-1-yl]acetyl]-4-piperidyl] thiazol-4-yl]-4,5-dihydroisoxazol-5-yl]-3-chloro-phenyl] methanesulfonate+TX, but-3-ynyl N-[6-[[(Z)-[(1-methyltetrazol-5-yl)-phenyl-methylene]amino] oxymethyl]-2-pyridyl]carbamate+TX, methyl N-[[5-[4-(2,4-dimethylphenyl)triazol-2-yl]-2-methyl-phenyl] methyl]carbamate+TX, 3-chloro-6-methyl-5-phenyl-4-(2,4,6-trifluorophenyl)pyridazine+TX, pyridachlometyl+TX, 3-(difluoromethyl)-1-methyl-N-[1,1,3-trimethylindan-4-yl]pyrazole-4-carboxamide+TX, 1-[2-[[1-(4-chlorophenyl)pyrazol-3-yl]oxymethyl]-3-methyl-phenyl]-4-methyl-tetrazol-5-one+TX, 1-methyl-4-[3-methyl-2-[[2-methyl-4-(3,4,5-trimethylpyrazol-1-yl)phenoxy]methyl]phenyl]tetrazol-5-one+TX, aminopyrifen+TX, ametoctradin+TX, amisulbrom+TX, penflufen+TX, (Z,2E)-5-[1-(4-chlorophenyl)pyrazol-3-yl]oxy-2-methoxyimino-N,3-dimethyl-pent-3-enamide+TX, florylpicoxamid+TX, fenpicoxamid+TX, tebufloquin+TX, ipflufenoquin+TX, quinofumelin+TX, isofetamid+TX, N-[2-[2,4-dichloro-phenoxy]phenyl]-3-(difluoromethyl)-1-methyl-pyrazole-4-carboxamide+TX, N-[2-[2-chloro-4-

(trifluoromethyl)phenoxy]phenyl]-3-(difluoromethyl)-1-methyl-pyrazole-4-carboxamide+TX, benzothiostrobin+TX, phenamacril+TX, 5-amino-1,3,4-thiadiazole-2-thiol zinc salt (2:1)+TX, fluopyram+TX, flutianil+TX, fluopimomide+TX, pyrapropoyne+TX, picarbutrazox+TX, 2-(difluoromethyl)-N-(3-ethyl-1,1-dimethyl-indan-4-yl)pyridine-3-carboxamide+TX, 2-(difluoromethyl)-N-((3R)-1,1,3-trimethylindan-4-yl)pyridine-3-carboxamide+TX, 4-[[6-[2-(2,4-difluorophenyl)-1,1-difluoro-2-hydroxy-3-(1,2,4-triazol-1-yl)propyl]-3-pyridyl]oxy]benzonitrile+TX, metyltetraprole+TX, 2-(difluororethyl)-N-((3R)-1,1,3-trimethylindan-4-yl)pyridine-3-carboxamide+TX, α-(1,1-dirmethylethyl)-α-[4'-(trifluoromethoxy)[1,1'-biphenyl]-4-yi]-5-pyrimidinemethanol+TX, fluoxapiprolin+TX, enoxastrobin+TX, 4-[[6-[2-(2,4-difluorophenyl)-1,1-difluoro-2-hydroxy-3-(1,2,4-triazol-1-yl)propyl]-3-pyridyl]oxy] benzonitrile+TX, 4-[[6-[2-(2,4-difluorophenyl)-1,1-difluoro-2-hydroxy-3-(5-sulfanyl-1,2,4-triazol-1-yl)propyl]-3-pyridyl]oxy] benzonitrile+TX, 4-[[6-[2-(2,4-difluorophenyl)-1,1-difluoro-2-hydroxy-3-(5-thioxo-4H-1,2,4-triazol-1-yl)propyl]-3-pyridyl]oxy]benzonitrile+TX, trinexapac+TX, coumoxystrobin+TX, zhongshengmycin+TX, thiodiazole copper+TX, zinc thiazole+TX, amectotractin+TX, iprodione+TX, mixtures of (N-methoxy-N-[[4-[5-(trifluoromethyl)-1,2,4-oxadiazol-3-yl]phenyl]methyl]cyclopropanecarboxamide+TX, N,2-dimethoxy-N-[[4-[5-(trifluoromethyl)-1,2,4-oxadiazol-3-yl]phenyl]methyl]propanamide+TX, N-ethyl-2-methyl-N-[[4-[5-(trifluoromethyl)-1,2,4-oxadiazol-3-yl]phenyl]methyl]propanamide+TX, 1-methoxy-3-methyl-1-[[4-[5-(trifluoromethyl)-1,2,4-oxadiazol-3-yl]phenyl]methyl]urea+TX, 1,3-dimethoxy-1-[[4-[5-(trifluoromethyl)-1,2,4-oxadiazol-3-yl]phenyl]methyl]urea+TX, 3-ethyl-1-methoxy-1-[[4-[5-(trifluoromethyl)-1,2,4-oxadiazol-3-yl]phenyl]methyl]urea+TX, N-[[4-[5-(trifluoromethyl)-1,2,4-oxadiazol-3-yl]phenyl]methyl]propanamide+TX, 4,4-dimethyl-2-[[4-[5-(trifluoromethyl)-1,2,4-oxadiazol-3-yl]phenyl]methyl]isoxazolidin-3-one+TX, 5,5-dimethyl-2-[[4-[5-(trifluoromethyl)-1,2,4-oxadiazol-3-yl]phenyl]methyl]isoxazolidin-3-one+TX, ethyl 1-[[4-[5-(trifluoromethyl)-1,2,4-oxadiazol-3-yl]phenyl]methyl]pyrazole-4-carboxylate+TX, and N,N-dimethyl-1-[[4-[5-(trifluoromethyl)-1,2,4-oxadiazol-3-yl]phenyl]methyl]-1,2,4-triazol-3-amine+TX), wherein the compound in the mixture, other than TX, may be prepared from the methods described in WO 2017/055473, WO 2017/055469, WO 2017/093348 and WO 2017/118689, 2-[6-(4-chlorophenoxy)-2-(trifluoromethyl)-3-pyridyl]-1-(1,2,4-triazol-1-yl)propan-2-ol+TX (this compound may be prepared from the methods described in WO 2017/029179), 2-[6-(4-bromophenoxy)-2-(trifluoromethyl)-3-pyridyl]-1-(1,2,4-triazol-1-yl)propan-2-ol+TX (this compound may be prepared from the methods described in WO 2017/029179), 3-[2-(1-chlorocyclopropyl)-3-(2-fluorophenyl)-2-hydroxy-propyl]imidazole-4-carbonitrile+TX (this compound may be prepared from the methods described in WO 2016/156290), 3-[2-(1-chlorocyclopropyl)-3-(3-chloro-2-fluoro-phenyl)-2-hydroxy-propyl]imidazole-4-carbonitrile+TX (this compound may be prepared from the methods described in WO 2016/156290), (4-phenoxyphenyl)methyl 2-amino-6-methyl-pyridine-3-carboxylate+TX (this compound may be prepared from the methods described in WO 2014/006945), 2,6-Dimethyl-1H,5H-[1,4]dithiino[2,3-c:5,6-c']dipyrrole-1,3,5,7(2H,6H)-tetrone+TX (this compound may be prepared from the methods described in WO 2011/138281), N-methyl-4-[5-(trifluoromethyl)-1,2,4-oxadiazol-3-yl]benzenecarbothioamide+TX, N-methyl-4-[5-(trifluoromethyl)-1,2,4-oxadiazol-3-yl]benzamide+TX, (Z,2E)-5-[1-(2,4-dichlorophenyl)pyrazol-3-yl]oxy-2-methoxyimino-N,3-dimethyl-pent-3-enamide+TX (this compound may be prepared from the methods described in WO 2018/153707), N'-(2-chloro-5-methyl-4-phenoxy-phenyl)-N-ethyl-N-methyl-formamidine+TX, N'-[2-chloro-4-(2-fluorophenoxy)-5-methyl-phenyl]-N-ethyl-N-methyl-formamidine+TX (this compound may be prepared from the methods described in WO 2016/202742), and 2-(difluoromethyl)-N-[(3S)-3-ethyl-1,1-dimethyl-indan-4-yl]pyridine-3-carboxamide+TX (this compound may be prepared from the methods described in WO 2014/095675), microbials including: *Acinetobacter iwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, Azospirillum+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus* papillae (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacil-*

*lus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of Clavipacter *michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, *Schweizer Beauveria*®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain 0+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus* infirmo-miniatus+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, Cylindrocladium+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma* piliferum strain D97 (Sylvanex®)+TX, *Paecilomyces farinosus*+TX, *Paecilomyces fumosoroseus* (PFR-97®+TX, PreFeRal®)+TX, *Paecilomyces* (linacinus Biostat WP®)+TX, *Paecilomyces lilacinus* strain 251 (MeloCon WG®)+TX, *Paenibacillus polymyxa*+TX, *Pantoea agglomerans* (BlightBan $C_9$-1®)+TX, *Pantoea* spp.+TX, *Pasteuria* spp. (Econem®)+TX, *Pasteuria nishizawae*+TX, *Penicillium* aurantiogriseum+TX, *Penicillium billai* (Jumpstart®+TX, TagTeam®)+TX, *Penicillium* brevicompactum+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis* gigantean (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, Pseudozyma flocculosa strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium* periplocum+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia* minor (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomy-*

*ces violaceus*+TX, *Tilletiopsis minor*+TX, *Tilletiopsis* spp.+TX, *Trichoderma* asperellum (T34 Biocontrol®)+TX, *Trichoderma* gamsii (Tenet®)+TX, *Trichoderma* atroviride (Plantmate®)+TX, *Trichoderma hamatum* TH 382+TX, *Trichoderma harzianum* rifai (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibaclillus marismortui*+TX, *Xanthomonas campestris* pv. *Poae* (Camperico®)+TX, *Xenorhabdus bovienii*+TX, *Xenorhabdus nematophilus;*

Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, *Pedaliaceae oil* (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®);

pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, *Leafroller pheromone* (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, *Entostat powder* (extract from palm tree) (Exosex CM®)+TX, (E+TX,Z+TX,Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; Macrobials including: *Aphelinus abdominalis*+TX, *Aphidius ervi* (*Aphelinus*-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, *Andersoni*-System®)+TX, *Amblyseius californicus* (Amblyline®+TX, Spical®)+TX, *Amblyseius cucumeris* (Thripex®+TX, *Bugline cucumeris*®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus* asychis+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (*Encarsia* Max®+TX, Encarline®+TX, En-Strip®)+TX, *Eretmocerus eremicus* (Enermix®)+TX, *Encarsia guadeloupae*+TX, *Encarsia* haitiensis+TX, *Episyrphus balteatus* (Syrphidend®)+TX, *Eretmoceris siphonini*+TX, *Eretmocerus californicus*+TX, *Eretmocerus eremicus* (Ercal®+TX, *Eretline e*®)+TX, *Eretmocerus eremicus* (Bemimix®)+TX, *Eretmocerus hayati*+TX, *Eretmocerus* mundus (Bemipar®+TX, *Eretline m*®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis* megidis (Nemasys H®+TX, BioNem H®+TX, *Exhibitline hm*®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia* caesar (Natufly®)+TX, *Lysiphlebus testaceipes*+TX, *Macrolophus caliginosus* (Mirical-N®+TX, *Macroline c*®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, *Oriline i*®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus* macropilus+TX, *Phytoseiulus persimilis* (Spidex®+TX, *Phytoline p*®)+TX, *Podisus maculiventris* (*Podisus*®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, Steinernema-System®+TX, NemAttack®+TX, Nemaplus®+TX, *Exhibitline sf*®+TX, Scia-Rid®+TX, Entonem®)+TX, *Steinernema kraussei* (Nemasys L®+TX, BioNem L®+TX, *Exhibitline srb*®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, Xanthopimpla stemmator; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, *Delta traps*

(Trapline d®)+TX, *Erwinia amylovora* (Harpin) (ProAct®+TX, Ni-HIBIT Gold CST®)+TX, Ferri-phosphate (Ferramol®)+TX, *Funnel traps* (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, *Pheromone trap* (Thripline Ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, *Spider venom*+TX, *Nosema* locustae (Semaspore Organic Grasshopper Control®)+TX, *Sticky traps* (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual-A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright© 1995-2004].

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name". a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from the compounds defined in the Tables A-1 to A-92, and Table P, and with active ingredients described above comprises a compound selected from Tables A-1 to A-92, and Table P, and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from the compounds defined in the Tables A-1 to A-92, and Table P, and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of formula I of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula I. Further, it is hereby made available, a composition comprising a plant propagation material treated with a compound of formula I.

Seed treatment comprises all suitable seed treatment techniques known in the art, such as seed dressing, seed coating, seed dusting, seed soaking and seed pelleting. The seed treatment application of the compound formula I can be carried out by any known methods, such as spraying or by dusting the seeds before sowing or during the sowing/planting of the seeds.

The compounds of the invention can be distinguished from other similar compounds by virtue of greater efficacy at low application rates and/or different pest control, which can be verified by the person skilled in the art using the experimental procedures, using lower concentrations if necessary, for example 10 ppm, 5 ppm, 2 ppm, 1 ppm or 0.2 ppm; or lower application rates, such as 300, 200 or 100, mg of Al per $m^2$. The greater efficacy can be observed by an increased safety profile (against non-target organisms above and below ground (such as fish, birds and bees), improved physico-chemical properties, or increased biodegradability).

BIOLOGICAL EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 24 ppm, 12.5 ppm, 6 ppm, 3 ppm, 1.5 ppm, 0.8 ppm or 0.2 ppm.

Example B1: *Diabrotica balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:

P2, P3, P4, P5, P6, P7, P8, P14, P15, P16, P17, P18, P19, P20, P21, P22, P23, P24, P25, P27, P28, P29, P30, P31, P32, P33, P34, P35

Example B2: *Euschistus heros* (Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm:

P1, P2, P3, P7, P11, P12, P16, P17, P18, P22, P25, P29, P32, P33, P37, P38

Example B3: *Frankliniella occidentalis* (Western Flower *Thrips*):Feeding/Contact Activity Sunflower leaf discs were placed on agar in 24-well microtiter plates and sprayed with aqueous test solutions prepared from 10'000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm:

P1, P4, P12, P16, P28, P37

Example B4: *Chilo suppressalis* (Striped Rice Stemborer)

24-well microtiter plates with artificial diet were treated with aqueous test solutions prepared from 10'000 ppm DMSO stock solutions by pipetting. After drying, the plates were infested with L2 larvae (6-8 per well). The samples were assessed for mortality, anti-feeding effect, and growth inhibition in comparison to untreated samples 6 days after infestation. Control of *Chilo suppressalis* by a test sample is given when at least one of the categories mortality, anti-feedant effect, and growth inhibition is higher than the untreated sample.

The following compounds resulted in at least 80% control in at least one of the categories (mortality, anti-feedant effect, or growth inhibition) at an application rate of 200 ppm:

P1, P3, P4, P8, P11, P12, P14, P19, P21, P25, P27, P28, P29, P30, P31, P32, P33, P34, P35, P36, P37

Example B5: *Plutella xylostella* (Diamond Back Moth)

24-well microtiter plates with artificial diet were treated with aqueous test solutions prepared from 10'000 ppm DMSO stock solutions by pipetting. After drying, *Plutella* eggs were pipetted through a plastic stencil onto a gel blotting paper and the plate was closed with it. The samples were assessed for mortality and growth inhibition in comparison to untreated samples 8 days after infestation.

The following compounds gave an effect of at least 80% in at least one of the two categories (mortality or growth inhibition) at an application rate of 200 ppm:

P1, P2, P3, P4, P5, P7, P8, P9, P14, P15, P16, P17, P18, P21, P22, P23, P24, P25, P27, P28, P29, P30, P31, P32, P33, P34, P35, P36

Example B6: *Myzus persicae* (Green Peach Aphid): Feeding/Contact Activity

Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm:

P3, P4, P7, P11, P12, P16, P17, P18, P21, P22

Example B7: *Myzus persicae* (Green Peach Aphid): Systemic Activity

Roots of pea seedlings infested with an aphid population of mixed ages were placed directly into aqueous test solutions prepared from 10'000 DMSO stock solutions. The samples were assessed for mortality 6 days after placing seedlings into test solutions.

The following compounds resulted in at least 80% mortality at a test rate of 24 ppm:

P2, P12, P16, P17, P21

Example B8: *Myzus persicae* (Green Peach Aphid): Intrinsic Activity

Test compounds prepared from 10'000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compounds resulted in at least 80% mortality at a test rate of 12 ppm:

P2, P3, P4, P7, P11, P12, P16, P17, P18, P21, P22, P28, P30, P31, P32, P34, P36, P37, P38

Example B9: *Spodoptera littoralis* (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control in at least one of the categories (mortality, anti-feedant effect, or growth inhibition) at an application rate of 200 ppm:

P2, P3, P4, P5, P7, P15, P16, P17, P18, P20, P21, P22, P23, P24, P25, P27, P28, P29, P30, P31, P32, P33, P34, P35, P36

Example B10: *Spodoptera littoralis* (Egyptian Cotton Leaf Worm)

Test compounds were applied by pipette from 10'000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm:

P3, P15, P32

Example B11: *Tetranychus urticae* (Two-Spotted Spider Mite): Feeding/Contact Activity Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:

P36

Example B12: *Thrips tabaci* (Onion *thrips*): Feeding/Contact Activity

Sunflower leaf discs were placed on agar in 24-well microtiter plates and sprayed with aqueous test solutions prepared from 10'000 ppm DMSO stock solutions. After drying the leaf discs were infested with a *thrips* population of mixed ages. The samples were assessed for mortality 6 days after infestation.

The following compounds resulted in at least 80% mortality at an application rate of 200 ppm:

P5, P7, P17, P18, P22

Example B13: *Myzus persicae* (Green Peach Aphid)

Test compounds prepared from 10'000 ppm DMSO stock solutions were applied by a liquid handling robot into 96-well microtiter plates and mixed with a sucrose solution. Parafilm was stretched over the 96-well microtiter plate and a plastic stencil with 96 holes was placed onto the plate. Aphids were sieved into the wells directly onto the Parafilm. The infested plates were closed with a gel blotting card and a second plastic stencil and then turned upside down. The samples were assessed for mortality 5 days after infestation.

The following compounds resulted in at least 80% mortality at an application rate of 50 ppm:

P2, P3, P5, P7, P11, P12, P14, P15, P16, P17, P18, P21, P22, P30, P32, P33, P37, P38

Example B14: *Plutella xylostella* (Diamondback Moth)

96-well microtiter plates containing artificial diet were treated with aqueous test solutions, prepared from 10'000 ppm DMSO stock solutions, by a liquid handling robot. After drying, eggs (~30 per well) were infested onto a netted lid which was suspended above the diet. The eggs hatch and L1 larvae move down to the diet. The samples were assessed for mortality 9 days after infestation.

The following compounds gave an effect of at least 80% average mortality at an application rate of 500 ppm:

P2, P3, P5, P6, P7, P9, P15, P16, P17, P18, P20, P22, P24, P25, P30, P31, P32, P33, P38.

The invention claimed is:

1. A compound of the formula I

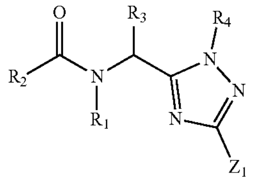

I wherein:

$R_1$ is hydrogen, $C_1$-$C_6$alkyl, $C_1$-$C_6$cyanoalkyl, aminocarbonyl$C_1$-$C_6$alkyl, hydroxycarbonyl$C_1$-$C_6$alkyl, $C_1$-$C_6$nitroalkyl, trimethylsilane$C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl; $C_3$-$C_4$cycloalkyl$C_1$-$C_2$alkyl- wherein the $C_3$-$C_4$cycloalkyl is optionally substituted with 1 or 2 halo atoms; oxetan-3-yl-$CH_2$—; or benzyl optionally substituted with halo or $C_1$-$C_6$haloalkyl;

$R_2$ is phenyl, pyridine, pyrimidine, pyrazine or pyridazine, wherein the phenyl, pyridine, pyrimidine, pyrazine or pyridazine is optionally substituted with one to three substituents, provided the substituent(s) are not on either carbon adjacent to the carbon C═O is attached, and each substituent is independently selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, halogen, $NO_2$, $SF_5$, CN, $CONH_2$, COOH and $C(S)NH_2$;

$R_3$ is $C_1$-$C_3$alkyl or $C_1$-$C_3$haloalkyl;

$R_4$ is pyridine, pyrimidine, pyrazine or pyridazine, wherein the pyridine, pyrimidine, pyrazine or pyridazine is optionally substituted with one substituent selected from $C_1$-$C_3$alkyl, $C_1$-$C_3$haloalkyl, $C_1$-$C_3$alkoxy, $C_3$-$C_4$cycloalkyl, halogen or hydroxy;

$Z_1$ is halogen, CN, $NH_2C(O)$, amino, ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, $C_1$-$C_3$alkoxy-$C_1$-$C_3$alkoxy, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), $(C_1$-$C_3alkyl)_2NC(O)$, ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, ($C_1$-$C_3$alkyl)C(O), HC(O), diphenylmethanimine, $C_1$-$C_3$haloalkoxy, phenyl or a 5-membered heteroaromatic ring wherein the phenyl or the 5-membered heteroaromatic ring is optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxy; or a stereoisomer, an enantiomer, a tautomer, an N-oxide, or an agrochemically acceptable salt thereof.

2. The compound according to claim 1, wherein $R_3$ is methyl.

3. The compound according to claim 1, wherein $R_1$ is hydrogen; $C_1$-$C_6$alkyl optionally substituted with one substituent selected from: CN, $CONH_2$, COOH, $NO_2$, and $-Si(CH_3)_3$; $C_1$-$C_6$aloalkyl; $C_2$-$C_6$alkenyl; $C_2$-$C_6$alkynyl; $C_2$-$C_6$haloalkynyl; $C_3$-$C_4$cycloalkyl-$C_1$-$C_2$alkyl- wherein the $C_3$-$C_4$cycloalkyl- is optionally substituted with 1 or 2 halo atoms; oxetan-3-yl-$CH_2$—; or benzyl optionally substituted with halo or $C_1$-$C_3$haloalkyl.

4. The compound according to claim 1, wherein $R_2$ is one of $Y_1$ to $Y_{21}$ $Y_1$

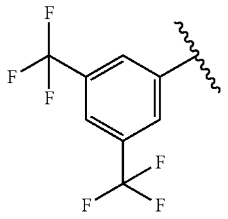

$Y_2$

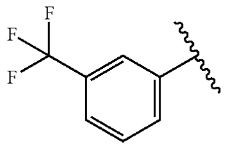

$Y_3$

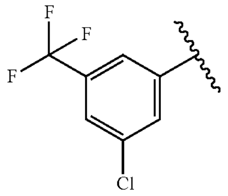

$Y_4$

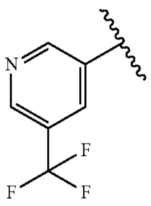

$Y_5$

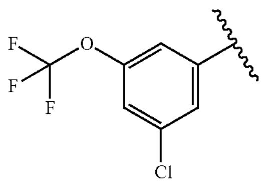

-continued $Y_6$

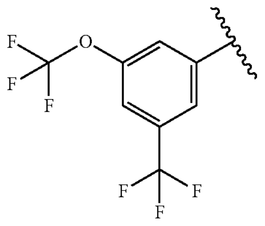

$Y_7$

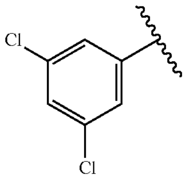

$Y_8$

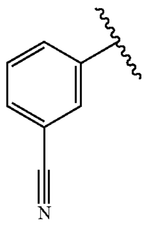

$Y_9$

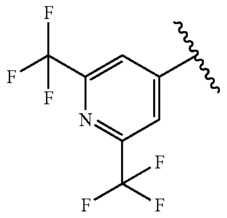

$Y_{10}$

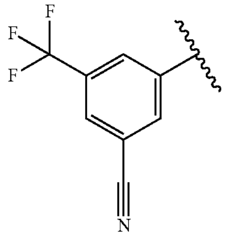

$Y_{11}$

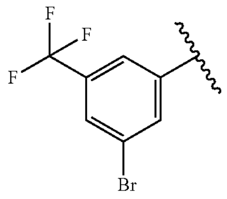

$Y_{12}$

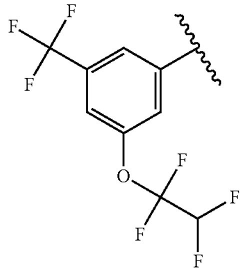

-continued
$Y_{13}$
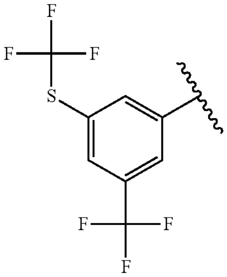
$Y_{14}$
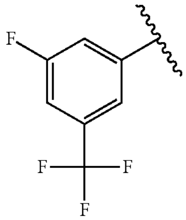
$Y_{15}$
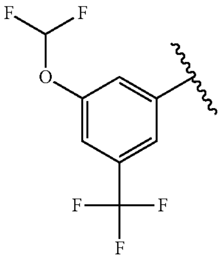
$Y_{16}$
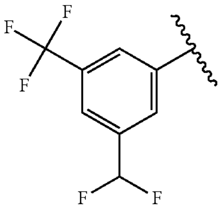
$Y_{17}$
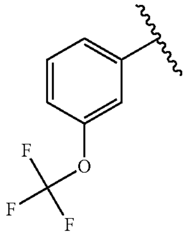
$Y_{18}$
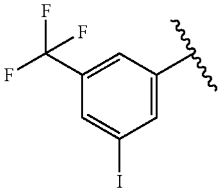
-continued
$Y_{19}$
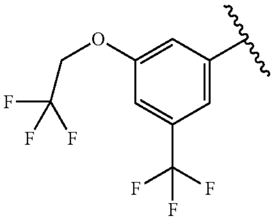
$Y_{20}$
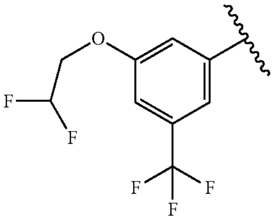
$Y_{21}$
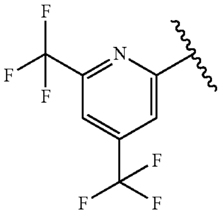
.
5. The compound according to claim 1, wherein $R_4$ is selected from $J_1$ to $J_8$
$J_1$
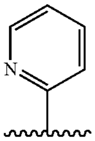
$J_2$
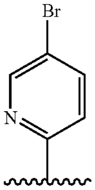
$J_3$
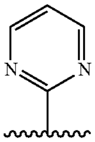
$J_4$
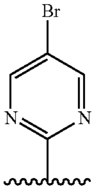

-continued

J5

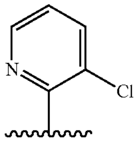

J6

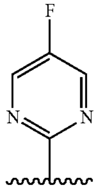

J7

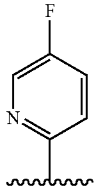

J8

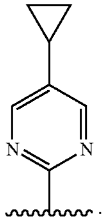

6. The compound according to claim 5, wherein $R_4$ is selected from $J_1$, $J_2$, $J_3$, $J_4$, $J_6$, $J_7$, and $J_8$.

7. The compound according to claim 4, wherein $R_1$ is cyclopropyl-$CH_2$—, $CH{\equiv}CCH_2$—, $CH_2{=}CHCH_2$—, hydrogen, or methyl; and $R_3$ is methyl.

8. The compound according to claim 1, wherein $Z_1$ is halogen, CN, amino, ($C_1$-$C_3$alkyl)amino, di($C_1$-$C_3$alkyl)amino, hydroxyl, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)amino, ($C_1$-$C_3$alkyl)NHC(O), ($C_1$-$C_3$alkyl)$_2$NC(O), $NH_2$C(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, $C_1$-$C_3$haloalkoxy, ($C_1$-$C_3$alkyl)C(O), $C_1$-$C_3$alkoxy-$C_1$-$C_3$alkoxy, HC(O), or diphenylmethanimine.

9. The compound according to claim 4, wherein $Z_1$ is halogen, CN, amino, di($C_1$-$C_3$alkyl)amino, hydroxyl, $C_3$-$C_4$halocycloalkyl, $C_3$-$C_4$cyanocycloalkyl, ($C_1$-$C_3$alkyl)NHC(O), ($C_1$-$C_3$alkyl)$_2$NC(O), $NH_2$C(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, $C_1$-$C_3$haloalkoxy, ($C_1$-$C_3$alkyl)C(O), $C_1$-$C_3$alkoxy-$C_1$-$C_3$alkoxy, HC(O), or diphenylmethanimine.

10. A composition comprising a compound as defined in claim 1, one or more auxiliaries and diluent, and optionally one more other active ingredient.

11. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound as defined in claim 1.

12. A plant propagation material, comprising, or treated with or adhered thereto, a compound as defined in claim 1.

13. The compound according to 5, wherein $Z_1$ is halogen, CN, amino, di($C_1$-$C_3$alkyl)amino, hydroxyl, $C_3$-$C_4$halocycloalkyl, $C_3$-$C_4$cyanocycloalkyl, ($C_1$-$C_3$alkyl)NHC(O), ($C_1$-$C_3$alkyl)$_2$NC(O), $NH_2$C(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, $C_1$-$C_3$haloalkoxy, ($C_1$-$C_3$alkyl)C(O), $C_1$-$C_3$alkoxy-$C_1$-$C_3$alkoxy, HC(O), or diphenylmethanimine.

14. The compound according to 5, wherein $R_1$ is cyclopropyl-$CH_2$—, $CH{\equiv}CCH_2$—, $CH_2{=}CHCH_2$—, hydrogen, or methyl; and $Z_1$ is halogen, CN, amino, di($C_1$-$C_3$alkyl)amino, hydroxyl, $C_3$-$C_4$halocycloalkyl, $C_3$-$C_4$cyanocycloalkyl, ($C_1$-$C_3$alkyl)NHC(O), ($C_1$-$C_3$alkyl)$_2$ NC(O), $NH_2$C(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, $C_1$-$C_3$haloalkoxy, ($C_1$-$C_3$alkyl)C(O), $C_1$-$C_3$alkoxy-$C_1$-$C_3$alkoxy, HC(O), or diphenylmethanimine.

* * * * *